United States Patent [19]
Sanderson et al.

[11] Patent Number: 5,866,573
[45] Date of Patent: Feb. 2, 1999

[54] PYRAZINONE THROMBIN INHIBITORS

[75] Inventors: Philip E.. Sanderson, Philadelphia; Terry A.. Lyle, Lederach; Bruce D. Dorsey, Maple Glen, all of Pa.; Richard J. Varsolona, Scotch Plains, N.J.

[73] Assignee: Merck & Co., Inc., Rahway, N.J.

[21] Appl. No.: 837,682

[22] Filed: Apr. 21, 1997

Related U.S. Application Data

[60] Provisional application No. 60/016,041, Apr. 23, 1996.
[51] Int. Cl.⁶ .................... A61K 31/495; C07D 401/12; C07D 403/12; C07D 413/12
[52] U.S. Cl. .................. 514/235.8; 514/252; 514/253; 514/255; 544/120; 544/405; 544/408
[58] Field of Search ..................... 544/405, 408, 544/120; 514/252, 253, 235.8, 255

[56] References Cited

U.S. PATENT DOCUMENTS 5,459,142 10/1995 Tone et al. ............... 514/252

FOREIGN PATENT DOCUMENTS 0 262 096  9/1987  European Pat. Off. .

*Primary Examiner*—Emily Bernhardt
*Attorney, Agent, or Firm*—Richard S. Parr; Melvin Winokur

[57] ABSTRACT

Compounds of the invention are useful in inhibiting thrombin and associated thrombotic occlusions having the following structure:

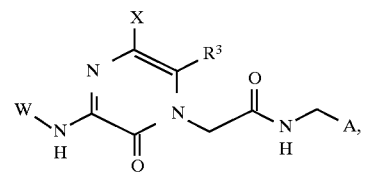

for example:

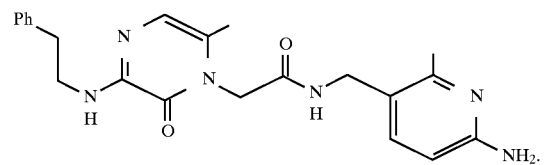

18 Claims, No Drawings

PYRAZINONE THROMBIN INHIBITORS

CROSS-REFERENCE TO RELATED APPLICATIONS

This patent application is a non-provisional patent application claiming priority to U.S. provisional application 60/016,041, filed Apr. 23, 1996.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

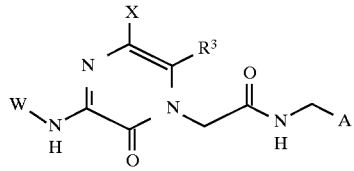

wherein
W is
  hydrogen,
  $R^1$,
  $R^1OCO$,
  $R^1CO$,
  $R^1(CH_2)_nNHCO$, or
  $(R^1)_2CH(CH_2)_nNHCO$,
  wherein n is 0–4;
$R^1$ is
  $R^2$,
  $R^2(CH_2)_mC(R^{12})_2$, where m is 0–3, and each $R^{12}$ can be the same or different,
  $(R^2)(OR^2)CH(CH_2)_p$, where p is 1–4,
  $R^2C(R^{12})_2(CH_2)_m$, wherein m is 0–3, and each R $^{12}$ can be the same or different, wherein $(R^{12})_2$ can also form a ring with C represented by $C_{3-7}$ cycloalkyl,
  $R^2CH_2C(R^{12})_2(CH_2)_q$, wherein m is 0–2, and each $R^{12}$ can be the same or different, wherein $(R^{12})_2$ can also form a ring with C represented by $C_{3-7}$ cycloalkyl,
  $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5-to 7-membered mono- or bicyclic heterocyclic ring which can be saturated or unsaturated, and which contains from one to three heteroatoms selected from the group consisting of N, O and S,
  $R^2O(CH_2)_p$, wherein p is 1–4, or
  $R^2(COOR^3)(CH_2)_r$, where r is 1–4;
$R^2$ and $R^{14}$ are independently
  phenyl, unsubstituted or substituted with one or more of $C_{1-4}$ alkyl, $C_{1-4}$ alkoxy, halogen, hydroxy, COOH, $CONH_2$, or $SO_2NH_2$,
  naphthyl,
  biphenyl,
  a 5-to 7-membered mono- or a 9-to 10-membered bicyclic heterocyclic ring or non-heterocyclic ring which can be saturated or unsaturated, wherein the heterocyclic ring contains from one to four heteroatoms selected from the group consisting of N, O, and S, and wherein the heterocyclic or non-heterocyclic ring is unsubstituted or substituted with halogen or hydroxy,
  $C_{1-7}$ alkyl, unsubstituted or substituted with one or more of
  hydroxy,
  COOH,
  amino,
  aryl,
  $C_{3-7}$ cycloalkyl,
  $CF_3$,
  $N(CH_3)_2$,
  $—C_{1-3}$alkylaryl,
  heteroaryl, or
  heterocycloalkyl, CF$_3$
C$_{3-7}$ cycloalkyl, unsubstituted or substituted with aryl,
C$_{7-12}$ bicyclic alkyl, or
C$_{10-16}$ tricyclic alkyl;
R$^3$ is
  hydrogen,
  C$_{1-4}$ alkyl,
  C$_{3-7}$ cycloalkyl, or
  trifluoromethyl;
X is
  hydrogen, or
  halogen;
A is chosen from one of the following radicals:

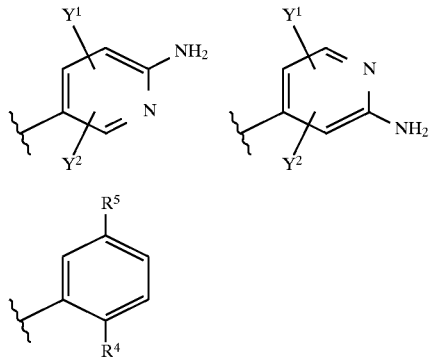

wherein Y$^1$ and Y$^2$ are independently
  hydrogen,
  C$_{1-4}$ alkyl,
  C$_{1-4}$ alkoxy,
  C$_{3-7}$ cycloalkyl,
  halogen, or
  trifluoromethyl;
R$^4$ is
  hydrogen,
  C$_{1-4}$ alkyl,
  C$_{1-4}$ alkoxy,
  halogen,
  —OCH$_2$CF$_3$,
  —OCH$_2$CN,
  —COOH,
  —OH,
  —COOR$^6$, where R$^6$ is C$_{1-4}$alkyl,
  —CONR$^7$R$^8$, where R$^7$ and R$^8$ are independently hydrogen or C$_{1-4}$alkyl,
  —(CH$_2$)$_{1-4}$OH,
  —CH$_2$NHC(O)CH$_3$,
  —CH$_2$NHC(O)CF$_3$,
  —CH$_2$NHSO$_2$CH$_3$,
  —SO$_2$NH$_2$,
  —(CH$_2$)$_{1-4}$SO$_2$NR$^7$R$^8$,
  —(CH$_2$)$_{1-4}$SO$_2$R$^6$,
  a 5- to 7-membered mono- or a 9-to 10-membered bicyclic heterocyclic ring which can be saturated or unsaturated, and which contains from one to four heteroatoms selected from the group consisting of N, O, and S,
  —ZCH$_2$CO$_2$H,
  —ZCH$_2$CO$_2$CH$_3$,
  —ZCH$_2$R$^{14}$,
  —ZCH$_2$CO$_2$(CH$_2$)$_{1-3}$CH$_3$,
  —Z(CHR$^9$)$_{1-3}$C(O)NR$^{10}$R$^{11}$, wherein
    R$^9$ is H or C$_{1-4}$ alkyl,
    R$^{10}$ and R$^{11}$ are independently
      hydrogen,
      C$_{3-7}$ cycloalkyl,
      aryl,
      heteroaryl,
      heterocycloalkyl,
      —(CH$_2$)$_{1-2}$NCH$_2$CH$_3$,
      C$_{1-4}$ alkyl unsubstituted or substituted with one or more of:
        hydroxy,
        COOH,
        amino,
        aryl,
        heteroaryl, or
        heterocycloalkyl, or
      R$^{10}$ and R$^{11}$ are joined to form a four to seven membered cycloalkyl ring unsubstituted or substituted with hydroxy, amino or aryl,
    wherein Z is O, S or CH$_2$;
R$^5$ is
  hydrogen,
  halogen,
  C$_{1-4}$ alkyl,
  C$_{1-4}$ alkoxy,
  CF$_3$,
  CN, or
  CO$_2$NH$_2$; and
R$^{12}$ is
  hydrogen,
  phenyl, unsubstituted or substituted with one or more of C$_{1-4}$ alkyl, C$_{1-4}$ alkoxy, halogen, hydroxy, COOH, CONH$_2$,
  naphthyl,
  biphenyl,
  a 5-to 7-membered mono- or a 9-to 10-membered bicyclic heterocyclic ring which can be saturated or unsaturated, and which contains from one to four heteroatoms selected from the group consisting of N, O, and S,
  C$_{1-4}$ alkyl, unsubstituted or substituted with one or more of
    hydroxy,
    COOH,
    amino,
    aryl,
    heteroaryl, or
    heterocycloalkyl,
  CF$_3$
  C$_{3-7}$ cycloalkyl,
  C$_{7-12}$ bicyclic alkyl, or
  C$_{10-16}$ tricyclic alkyl;
and pharmaceutically acceptable salts thereof.

In one class of compounds and pharmaceutically acceptable salts thereof, R$^3$ is C$_{1-4}$ alkyl.

In a subclass of this class of compounds and pharmaceutically acceptable salts thereof, A is chosen from one of the following radicals:

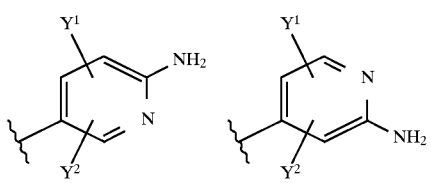

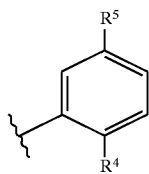

wherein $Y^1$ and $Y^2$ are independently hydrogen or $C_{1-4}$ alkyl;
$R^4$ is
  hydrogen,
  halogen,
  —$OCH_2CN$,
  —OH,
  —$ZCH_2CO_2H$, or
  —$Z(CHR^9)_{1-3}C(O)NR^{10}R^{11}$, wherein
    $R^9$ is H or $C_{1-4}$ alkyl, and
    $R^{10}$ and $R^{11}$ are independently
      hydrogen,
      $C_{3-7}$ cycloalkyl,
      —$(CH_2)_{1-2}NCH_2CH_3$, or
      $C_{1-4}$ alkyl,
    wherein Z is O, S or $CH_2$;
$R^5$ is
  hydrogen,
  halogen, or
  $CF_3$.

In a group of this subclass of compounds and pharmaceutically acceptable salts thereof, W is H or $R^1$.

In a subgroup of this group of compounds and pharmaceutically acceptable salts thereof, $R^1$ is $R^2$,
$R^2(CH_2)_mC(R^{12})_2$, where m is 0–3, and each $R^{12}$ can be the same or different,
$R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,
$(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5-to 7-membered mono- or bicyclic heterocyclic ring which can be saturated or unsaturated, and which contains from one to three heteroatoms selected from the group consisting of N, O, and S, or
$R^2O(CH_2)_p$, wherein p is 1–4;
$R^2$ and $R^{14}$ are independently phenyl, unsubstituted or substituted with one or more of $C_{1-4}$ alkyl, $C_{1-4}$ alkoxy, halogen, hydroxy, or $SO_2NH_2$,
  a 5-to 7-membered mono- or a 9-to 10-membered bicyclic heterocyclic ring or non-heterocyclic ring which can be saturated or unsaturated, wherein the heterocyclic ring contains from one to four heteroatoms selected from the group consisting of N, O, and S, and wherein the heterocyclic or non-heterocyclic ring is unsubstituted or substituted with halogen or hydroxy,
  $C_{1-7}$ alkyl, unsubstituted or substituted with one or more of
    hydroxy,
    COOH,
    $C_{3-7}$ cycloalkyl,
    $CF_3$,
    $N(CH_3)_2$,
    —$C_{1-3}$alkylaryl,
    heteroaryl, or
    heterocycloalkyl,
    $CF_3$, or
    $C_{3-7}$ cycloalkyl, unsubstituted or substituted with aryl; and
$R^{12}$ is
  hydrogen,
  $C_{1-4}$ alkyl, unsubstituted or substituted with one or more of
    hydroxy,
    COOH,
    amino,
    aryl,
    heteroaryl, or
    heterocycloalkyl.

In a family of this subgroup of compounds and pharmaceutically acceptable salts thereof,
A is i)

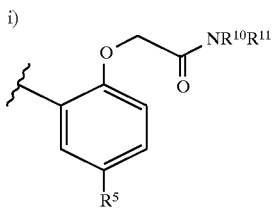

wherein
$R^5$ is H, fluoro, chloro, and
$R^{10}$ and $R^{11}$ are independently selected from
  H,
  $C_2H_5$,
  $C_3H_5$,
  $(CH_2)_2N(CH_3)_2$,
  $C_3$ cycloalkyl, ii)

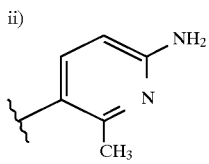

iii)

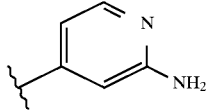

iv)

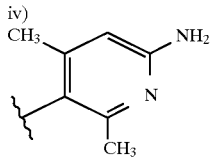

v)

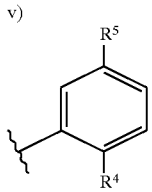

wherein $R^4$ is OH, chloro, H, —$OCH_2CN$, fluoro, —$OCH_2COOH$, and $R^5$ is chloro or $CF_3$, vi) 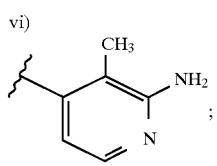
R³ is CH₃, or CH₂CH₃;
X is H or chloro; and
W is
  PhCH₂CH₂,
  (CH₃)₃C—,
  HOOCCH₂,
  CF₃CH₂,
  (CH₃)₂N(CH₂)₂,
  PhCH₂O(CH₂)₂,
  PhCH(CH₃),
  PhCH₂CH(COOH),
  CH₃(CH₂)₅,
  PhCH₂,
  H,
  CH₃(CH₂)₄,
  CH₃CH₂CH(CH₃)CH₂,
  (Ph)₂CHCH₂,
  PhCH₂CH(CH₃),
  PhCH₂C(CH₃)₂,
  PhCH(CH₃)CH₂,
  (CH₃)₂CH,
  PhCH(OH)CH₂,
  PhC(CH₃)₂CH₂,
  (Ph)₂CHCH₂,
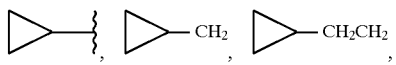
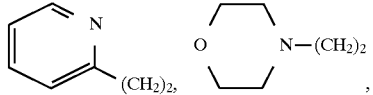
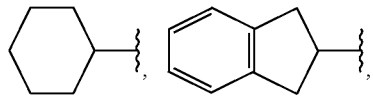
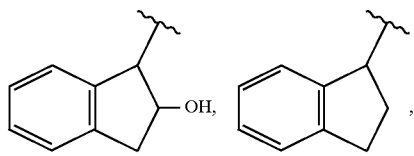
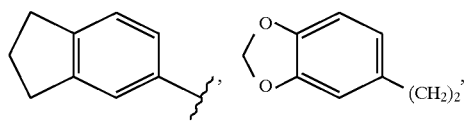
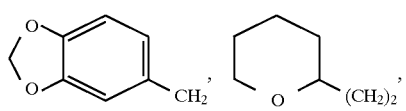
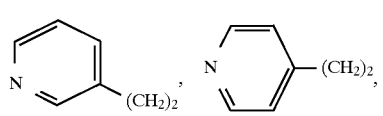
-continued
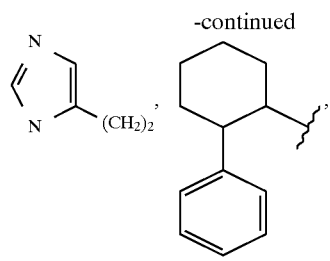
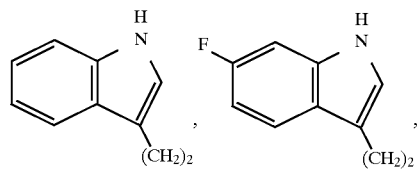
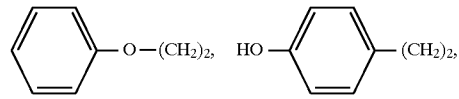
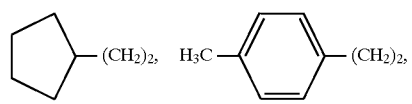
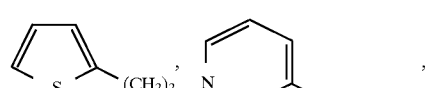
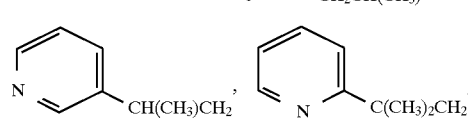
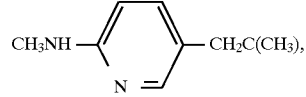
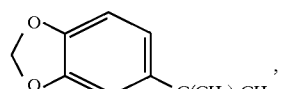
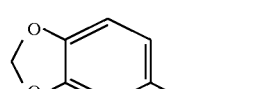
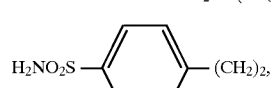
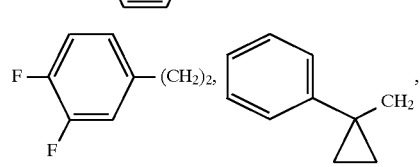
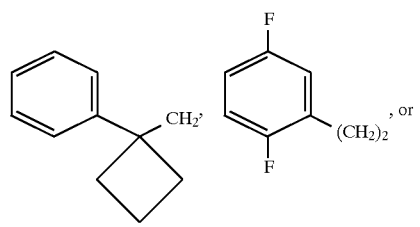

-continued
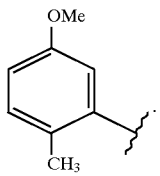
Examples of this family are listed in and following tables 1–4, and include (note that the methyl group is conventionally indicated as a single bond attached to a ring):
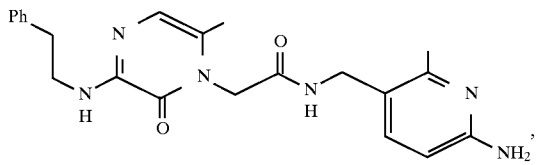
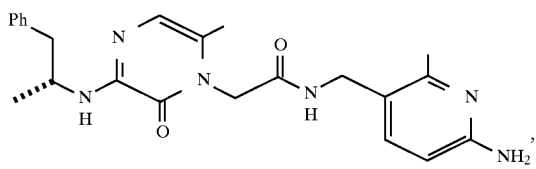
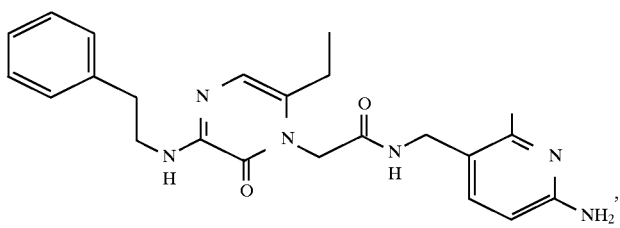
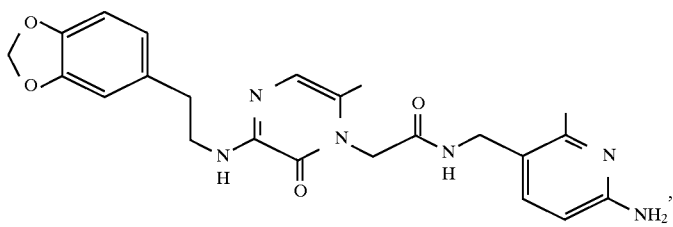
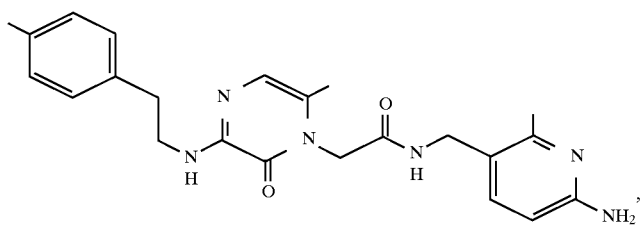
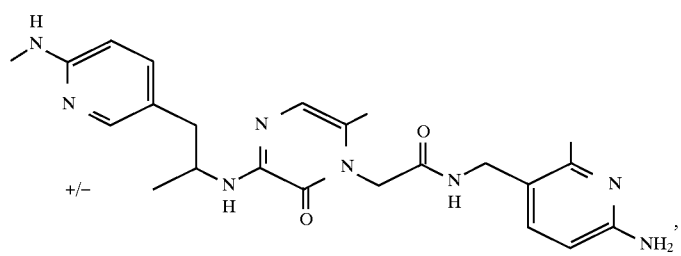

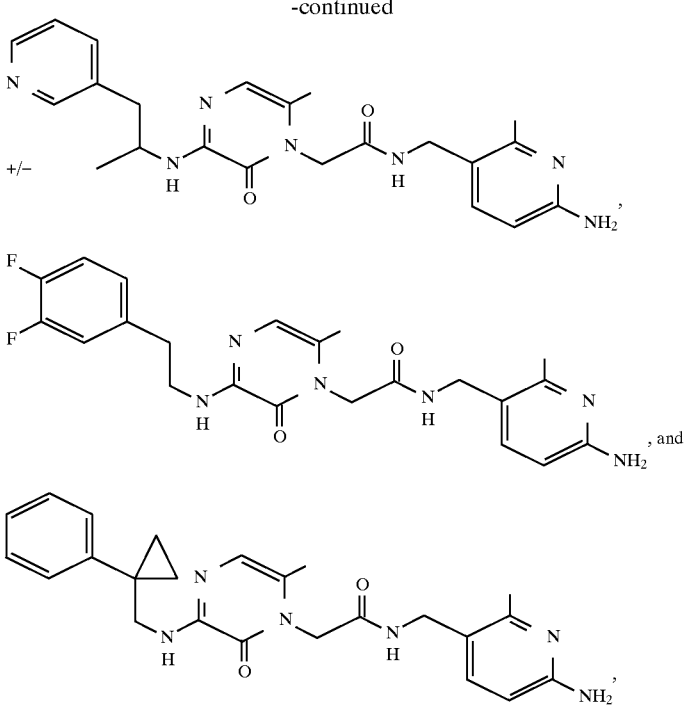

One particular example is the compound 3-(2-Phenethylamino)-6-methyl-1-(2-amino-6-methyl-5-methylcarboxamidomethylpyridinyl)-pyrazinone and pharmaceutically acceptable salts thereof. One particular salt of this compound is 3-(2-Phenethylamino)-6-methyl-1-(2-amino-6-methyl-5-methylcarboxamidomethylpyridinyl)-pyrazinone dihydrochloride. This salt can be prepared in one of two crystalline polymorphic forms, designated below as "Type A" and "Type B" (see example V).

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris- |

| ABBREVIATIONS | |
|---|---|
| | (dimethylamino)phosphonium hexafluorophosphate |
| BOP—Cl | bis(2-oxo-3-oxazolidinyl)phosphinic chloride |
| EDC | 1-ethyl-3-(3-dimethylaminopropyl) carbodiimide hydrochloride |
| | Other |
| (BOC)$_2$O(BOC$_2$O) | di-t-butyl dicarbonate |
| n-Bu$_4$N + F- | tetrabutyl ammonium fluoride |
| nBuLi(n-Buli) | n-butyllithium |
| DMF | dimethylformamide |
| Et$_3$N (TBA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6-to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino. The term "heteroaryl" refers to a 5-to 7-membered unsaturated ring containing 1 or 2 heteroatoms selected from O, N, or S.

The term "heterocycle" or "heterocyclic ring", as used herein except where noted, represents a stable 5-to 7-membered mono- or bicyclic or stable 7-to 10-membered bicyclic heterocyclic ring system any ring of which may be saturated or unsaturated, and which consists of carbon atoms and from one to four heteroatoms selected from the group consisting of N, O, and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow—Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical tablet cores suitable for administration of thrombin inhibitors are comprised of, but not limited to, the following amounts of standard ingredients:

| Suggested Ranges of Composition for Excipients in Uncoated Tablet Cores | | | |
|---|---|---|---|
| Excipient | General Range (%) | Preferred Range (%) | Most Preferred Range (%) |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following synthetic methods can be used to prepare the compounds of the present invention:

The following examples are illustrative of the invention as contemplated by the inventors and should not be construed as being limits on the scope or spirit of the instant invention.

METHOD 1 (Exemplified by Example I)

Starting allylamine is condensed with acetaldehyde and cyanide in Step A to afford the aminonitrile. This is reacted in Step B with oxalyl chloride according to the method of Hoomaert [*J. Heterocyclic Chem.*, 20, 919, (1983)] to give the pyrazinone. The olefin is oxidatively cleaved with ruthenium tetraoxide and the resulting aldehyde is converted to the acid by an oxidising agent such as chromic acid in Step C. The 3-chloro group is then displaced by an ammonia equivalent, in this case p-methoxybenzylamine in Step D. The remaining chlorine is removed by reduction with Raney nickel in Step E and in Step F the p-methoxybenzyl group is removed by treatment with a strong acid such as TFA. Finally, in Step G, the acid is coupled to the appropriate amine, in this case ethyl-2-aminomethyl-4-chlorophenoxyacetamide to give the final product (a method for the preparation of this amine is given below).

METHOD 1 (Exemplified By Example I)

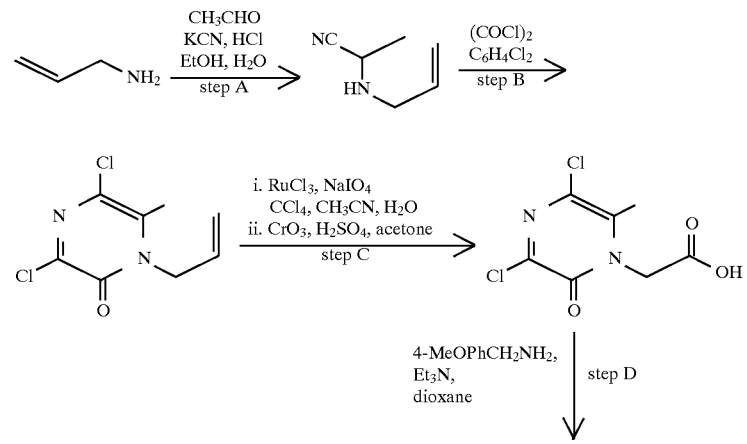

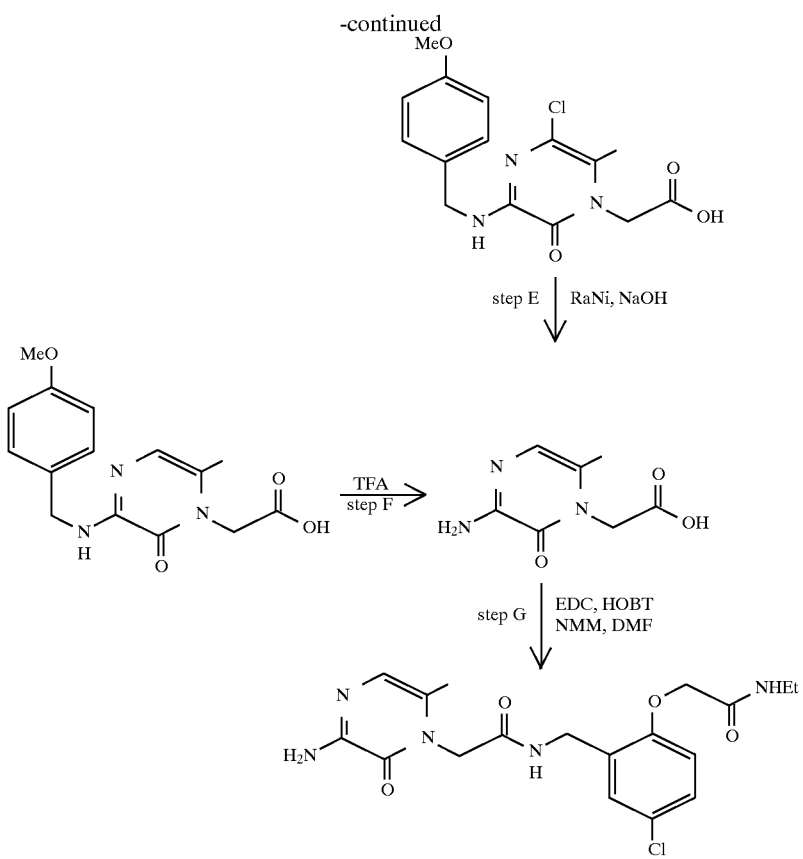

Amide couplings, e.g., Step G, to form the compounds of this invention can be performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. An appropriate choice of the amine in Step G will allow the different operable values of A to be achieved. Obvious variations and modifications of the method to produce similar and obvious variants thereof, will be apparent to one skilled in the art.

Method For Making Ethyl-2-Aminomethyl-4-Chlorophenoxyacetamide

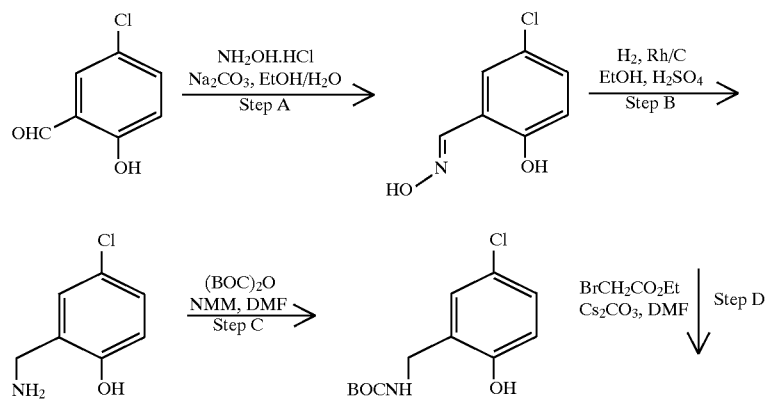

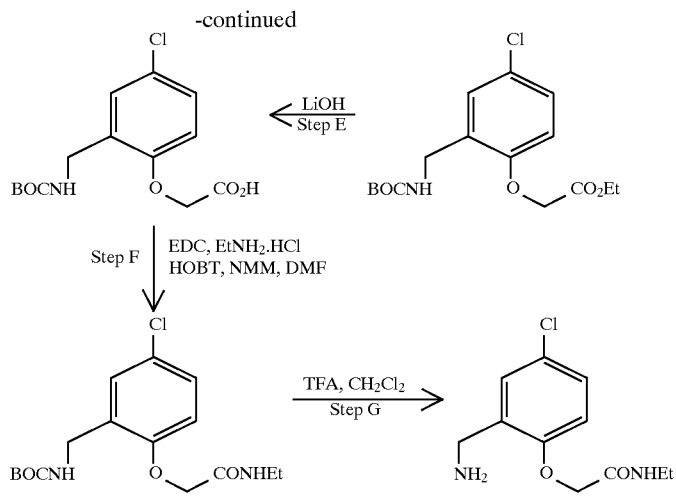

Modifications of this method will allow different $R^4$ and $R^5$ groups contemplated by the scope of the broad claim below to be present by the use of an appropriate reagent or appropriately substituted starting material in the indicated synthetic step. For example, appropriate choice of the amine in Step F will allow different values of $R^{10}$ and $R^{11}$ to be achieved. Obvious variations and modifications of the method to produce similar and obvious variants thereof, will be apparent to one skilled in the art.

Step A: 4-Chlorosalicaldehyde Oxime

A solution of hydroxylamine hydrochloride (16.7 g, 0.24 mol) and sodium carbonate (12.7 g, 0.12 mol) in water (120 ml) was added to a stirred solution of 4-chlorosalicaldehyde (25.0 g, 0.16 mol) in ethanol (160 ml) and the resulting solution was heated to reflux. After 1 h the reaction was cooled, water (320 ml) was added and the resulting crystalline precipitate was isolated by filtration. A second crop was similarly collected and the combined solids were dried to give the title compound:

$^1$H NMR (400 Mz, CDCl$_3$) d 6.92 (d, J=8.8 Hz, 1 H), 7.15 (d, J=2.6 Hz, 1H), 7.23 (dd, J=2.6 and 8.8 Hz, 1H), 7.26 (s, 1H), 8.16 (s, 1H), 9.71 (s, 1H).

Step B: 2-Hydroxy-5-Chlorobenzylamine

A mixture of 4-chlorosalicaldehyde oxime (10 g, 58.3 mmol) and 5% Rh/C (2.0 g) in ethanol (100 ml) containing concentrated sulfuric acid (10 ml) was shaken in a Parr apparatus under H$_2$ (60 psi) for 24 h. Water (100 ml) was added and the mixture was filtered through celite. The filtrate was concentrated until the product had crystallized out of solution. The solid was collected by filtration and the filtrate was further concentrated, adding water to give a second crop which was combined with the first to give, after drying the title compound, the sulfate salt:

$^1$H NMR (400 Mz, CD$_3$OD) d 4.07 (s, 2 H), 6.88 (d, J=8.6 Hz, 1 H), 7.25 (dd, J=2.6 and 8.6 Hz, 1H), 7.31 (d, J=2.6 Hz, 1 H).

Step C: N-t-Butoxycarbonyl-2-Hydroxy-5-Chlorobenzylamine

A mixture of 2-hydroxy-5-chlorobenzylamine (1.22 g, 4.77 mmol assuming the bisulfate salt), (BOC)$_2$O (1.56 g, 7.16 mmol) and N-methylmorpholine (1.05 ml, 9.54 mmol) in DMF (10 ml) was stirred for 5 h at r.t. The reaction was partitioned between water and ethyl acetate and the organic layer was washed with 5% KHSO$_4$ solution (2 times), sodium hydrogen carbonate solution and brine, dried (Na$_2$SO$_4$) and evaporated in vacuo to a solid. The crude product was recrystallized from ethyl acetate/hexanes (1:5, 12 ml) to give the title compound:

$^1$H NMR (400 Mz, CDCl$_3$) d 1.44 (s, 9 H, t-Bu), 4.17 (d, J=6.8 Hz, 2H, CH$_2$), 5.22 (br t, 1H, NH), 6.87 (d, J=8.6 Hz, 1H, H-3), 7.03 (d, J=2.6 Hz, 1H, H-6), 7.15 (dd, J=2.6 and 8.6 Hz, 1H, H-4).

Step D: Ethyl-2-t-Butoxycarbonylaminomethyl-4-Chlorophenoxyacetate

A mixture of N-t-butoxycarbonyl-2-hydroxy-5-chlorobenzylamine (730 mg, 2.83 mmol), Cs$_2$CO$_3$ (923 mg, 2.83 mmol) and ethylbromoacetate (0.314 ml, 2.83 mmol) in DMF (5 ml) was stirred for 2 h. The crude reaction mixture was partitioned between ethyl acetate and water and the organic layer was washed with brine, dried (Na$_2$SO$_4$) and evaporated in vacuo to an oil which was used for the next step.

Step E: 2-t-Butoxycarbonylaminomethyl-4-Chlorophenoxyacetic Acid

The product from Step D was suspended in 1:1:1 methanol/THF/water (9 ml) and lithium hydroxide hydrate (126 mg, 3.0 mmol) was added. After 16 h the volatiles were removed in vacuo and the solution was diluted with water and was washed with ethyl acetate, adding sufficient brine to disperse the emulsion. The aqueous layer was acidified with 5% KHSO$_4$ solution and was extracted with methylene chloride which was then dried (Na$_2$SO$_4$) and evaporated in vacuo to give the title compound as a solid:

$^1$H NMR (400 Mz, CDCl$_3$) d 1.44 (s, 9H, t-Bu), 4.35 (br s, 2H, NCH$_2$), 4.62 (s, 2H, OCH$_2$), 5.04 (br s, 1H, NH), 6.74 (d, J=7.9 Hz, 1H, H-3), 7.20 (d, J=2.6 Hz, 1H, H-6), 7.24 (d obscured, 1H, H-4).

Step F: Ethyl-2-t-Butoxycarbonylaminomethyl-4-Chlorophenoxyacetamide

EDC Hydrochloride (249 mg, 1.3 mmol) was added to a stirred mixture of 2-t-butoxycarbonylaminomethyl-4-chlorophenoxyacetic acid (316 mg, 1.0 mmol), HOBT (176 mg, 1.3 mmol), ethylamine hydrochloride (106 mg, 1.3 mmol) and N-methylmorpholine (0.396 ml, 3.6 mmol) in DMF (4 ml) and the mixture was stirred for 16 h. The reaction was partitioned between ethylacetate and 5% KHSO$_4$ solution and the organic layer was washed with 5% KHSO$_4$ solution, water, NaHCO$_3$ solution and brine, dried (Na$_2$SO$_4$) and evaporated in vacuo to a solid (333 mg) which was used for the next step.

Step G: Ethyl-2-Aminomethyl-4-Chlorophenoxyacetamide

Ethyl-2-t-butoxycarbonylaminomethyl-4-chlorophenoxyacetamide from Step F was dissolved in 2:1 methylene chloride/TFA (3 ml) and after 15 min the solvent was evaporated in vacuo. The residue was dissolved in water and the solution was washed with methylene chloride (twice). The aqueous layer was then basified with saturated sodium carbonate solution and NaCl was added to saturation. The mixture was extracted with ethyl acetate, and the organic layer was dried ($Na_2SO_4$) and evaporated in vacuo to give the title compound as a crystalline solid:

$^1$H NMR (300 MHz, $CDCl_3$) d 1.12 (t, J=7.3 Hz, 3H, Me), 1.54 (s, 9H, t-Bu), 3.31 (quintet, J=7.3 Hz, 2H, $CH_2Me$), 3.90 (s, 2H, $NCH_2$), 4.58 (s, 2H, $OCH_2$), 6.80 (d, J=8.3 Hz, 1H, H-3), 7.19–7.23 (m, 2H, H-4, H-6), 8.01 (br s, 1H, CONH).

METHOD 2 (Exemplified By Example II)

An alternative method for preparing compounds of the present invention is exemplified by Example II.

The acid from METHOD I, Step C is coupled to the appropriate amine, in this case 2-t-butoxycarbonylamino-5-aminomethyl-6-methylpyridine (a method for the preparation of this amine is shown below) in Step A. The 3-chloro group is then displaced by the appropriate amine, in this case phenethylamine in Step B and the BOC group is then removed in Step C to give the final product.

METHOD 2 (Exemplified By Example II)

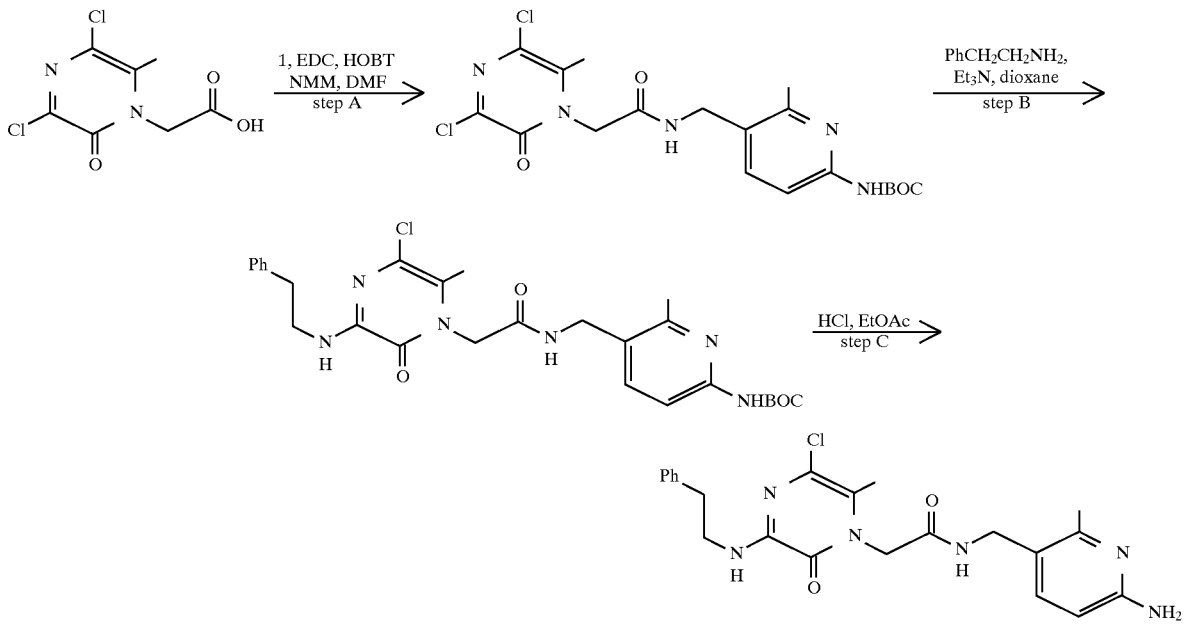

Modifications of the method will allow different W, $R^3$, X and A groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

Method for Making 2-t-Butoxycarbonylamino-5-Aminomethyl-6-Methylpyridine

Preparation of 2-Amino-5-cyano-6-methylpyridine

A mixture of 6-amino-3-bromo-2-methylpyridine (20.0 g, 0.107 mol)(Maybridge) and copper (I) cyanide 11.0 g, 0.123 mol) in DMF (25 ml) was heated to reflux for 4 h. The DMF was evaporated in vacuo and the residue was partitioned between ethyl acetate and 10% sodium cyanide solution. The organic layer was washed with 10% sodium cyanide solution and brine, dried ($Na_2SO_4$) and evaporated in vacuo to a brown solid. This was dissolved in a minimum amount of ethyl acetate and the product was precipitated by adding hexanes. The mixture was filtered to give the title compound as a brown powder:

$^1$H NMR ($CDCl_3$) d 2.56 (s, 3 H), 4.97 (br s, 2 H), 6.33 (d, J=8.6 Hz, 1 H), 7.54 (d, J=8.6 Hz, 1 H).

Preparation of 2-t-Butoxycarbonylamino-5-cyano-6-methylpyridine

A mixture of 2-amino-5-cyano-6-methylpyridine (10.0 g, 75.1 mmol), $(BOC)_2O$ (16.39 g, 75.1 mmol), triethylamine (11.5 ml, 82.6 mmol) and DMAP (0.92 g, 7.5 mmol) in methylene chloride (200 ml) was stirred for 3 h. More triethylamine (4.22 ml) and $(BOC_2)O$ (1.64 g) were added and after 16 h the reaction was diluted with ethyl acetate and was washed with 1M AcOH (3 times), dried ($Na_2SO_4$) and evaporated in vacuo to give dark brown solid. The crude product was purified by flash column chromatography (10% ethylacetate/hexanes) to give the title compound as a white solid:

$^1$H NMR ($CDCl_3$) d 1.52 (s, 9 H), 2.62 (s, 3 H), 7.46 (br s, 1 H), 7.80 (d, J=8.8 Hz, 1 H), 7.88 (d, J=8.8 Hz, 1 H).

Preparation of 2-t-Butoxycarbonylamino-5-aminomethyl-6-methylpyridine

A mixture of 2-t-butoxycarbonylamino-5-cyano-6-methylpyridine (14.68 g, 62.9 mmol) and 10% Pd/C (1.5 g) in glacial acetic acid (150 ml) was shaken on a Parr apparatus at 60 psi for 88 h. The reaction was filtered through celite and was evaporated in vacuo. The residue was dissolved in water and the solution was washed with methylene chloride (2 times), then was basified with sodium carbonate and extracted with ethyl acetate (2 times). The combined ethyl acetate layers were dried ($Na_2SO_4$) and evaporated in vacuo to a solid. The crude product was recrystallized (ethyl acetate/hexanes) to give the title compound:

$^1$H NMR ($CDCl_3$) d 1.50 (s, 9 H), 2.43 (s, 3 H), 3.81 (s, 2 H), 7.23 (br s, 1 H), 7.57 (d, J=8.3 Hz, 1 H), 7.70 (d, J=8.3 Hz, 1 H).

Modifications of this method will allow different $Y^1$ and $Y^2$ groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 3 (Exemplified by Example V)

An ester of glycine, in this case the benzyl ester, is condensed with acetaldehyde and cyanide in Step A to afford the aminonitrile. This is reacted in Step B with oxalyl chloride to give the pyrazinone. The 3-chloro group is then displaced by the appropriate amine, in this case phenethylamine, in Step C. The ester is hydrolysed in Step D and the remaining chlorine is then removed by hydrogenolysis in Step E. The acid is then coupled in Step F with the appropriate amine, in this case 2-amino-5-aminomethyl-6-methylpyridine (a method for the preparation of this amine is shown below) to afford the final product.

$^1$H NMR (CD$_3$OD): d 2.58 (s, 3 H), 4.12 (s, 2 H), 6.92 (d, J=9.2 Hz, 1 H), 7.93 (d, J=9.2 Hz, 1 H).

Obvious variations and modifications of the method to produce similar and obvious variants thereof, will be apparent to one skilled in the art.

METHOD 4

The product of Step E, Method 3 is coupled with the appropriate protected amine, for example 2-t-butoxycarbonylamino-5-aminomethyl-6-methylpyridine, and then deprotected to afford the final product. Obvious variations and modifications of the method to produce similar and obvious variants thereof, will be apparent to one skilled in the art.

METHOD 5 (Exemplified by Example LXXXII)

Starting allylamine is condensed with acetaldehyde and cyanide in Step A to afford the aminonitrile. This is reacted

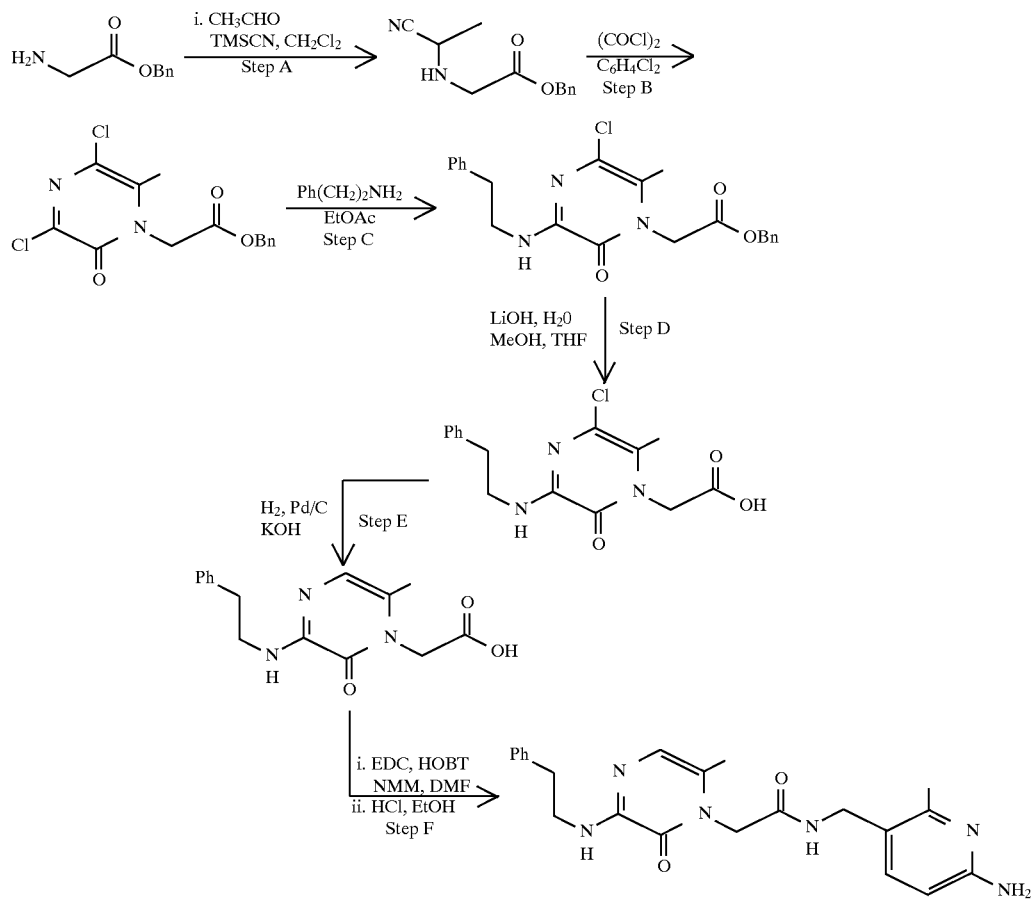

Preparation of 2-Amino-5-aminomethyl-6-methylpyridine dihydrochloride

A mixture of 2-amino-5-cyano-6-methylpyridine (4.0 g, 30.0 mmol) and 10% Pd/C (3.08 g) in ethanol (80 mL), methanol (30 mL), concentrated HCl (6 mL) and water (10 mL) was shaken on a Parr apparatus at 60 psi for 25 h. The reaction was filtered through celite, rinsing with 1:1 ethanol/methanol and was evaporated in vacuo to a solid, which was triturated with 5:1 ethyl acetate/ethanol to give the title compound (5.95 g, 94%):

in Step B with oxalyl chloride according to the method of Hoornaert [J. Heterocyclic Chem., 20, 919, (1983)] to give the pyrazinone. The olefin is oxidatively cleaved with ruthenium tetraoxide and the resulting aldehyde is converted to the acid by an oxidising agent such as chromic acid in Step C. The 3-chloro group is then displaced by the appropriate amine, in this case phenethylamine, in Step D and the remaining chlorine is then removed by reduction with Raney nickel in Step E. The acid is then coupled in Step F with the appropriate amine, in this case 3-aminomethyl-6-BOCamino-2-methylpyridine and the BOC group is removed using a strong acid such as HCl gas in step G to afford the final product.

METHOD 5 (CONT'D)

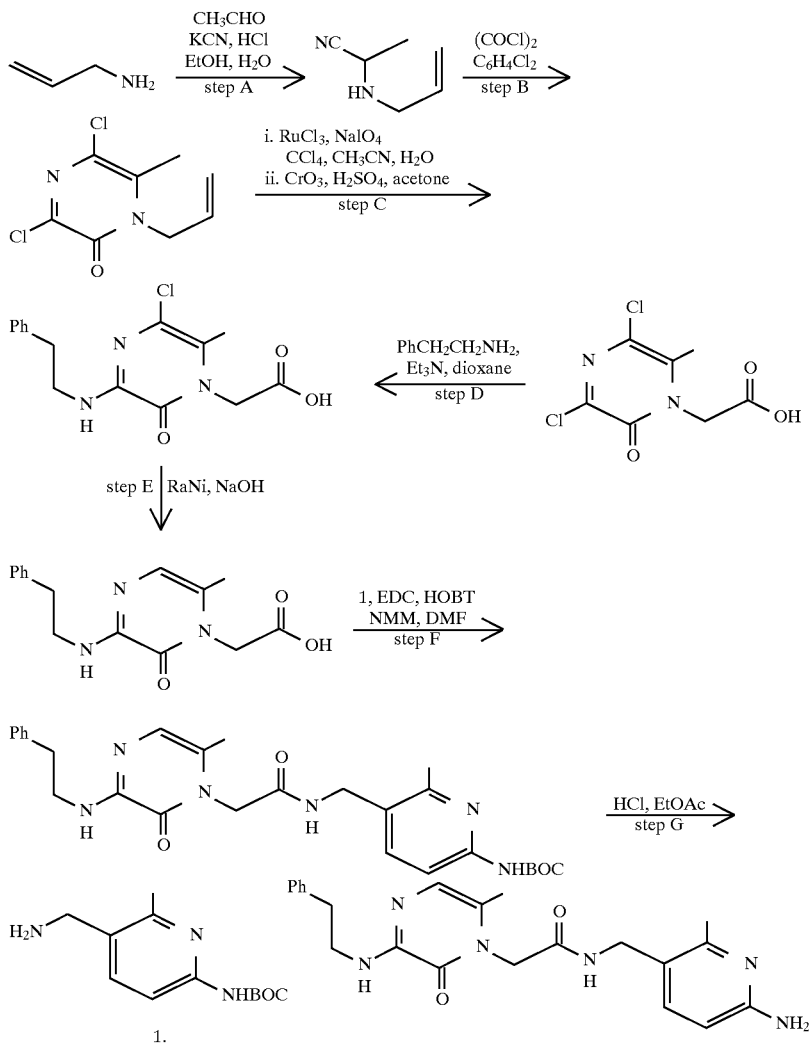

Amide couplings, e.g., Step F, to form the compounds of this invention can be performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. An appropriate choice of the amine in Step F will allow the different operable values of A to be achieved. Thus, as exemplified by Example VI, the product of Step E is coupled to derivatives of 2-hydroxybenzylamine, in this case ethyl-(2-aminomethyl-4-chlorophenoxy)-acetamide to give the final product. Obvious variations and modifications of the method to produce similar and obvious variants thereof, will be apparent to one skilled in the art.

The following examples are illustrative of the invention as contemplated by the inventors and should not be construed as being limits on the scope or spirit of the instant invention.

EXAMPLE I

Preparation of 3-Amino-6-Methyl-1-[Ethyl-(2-Methyl-carboxamidomethyl-4-Chlorophenoxy)-Acetamido]-2-Pyrazinone

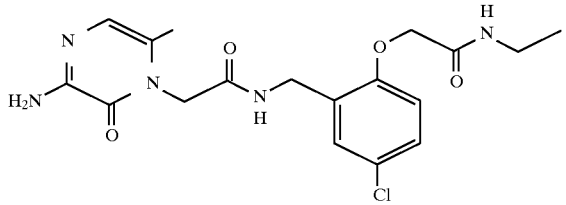

Step A: α-(Allylamino)-propionitrile hydrochloride

Concentrated HCl (20 ml, 0.24 mol)) was added to a stirred solution of allylamine (36 ml, 0.48 mol) in water (100 ml) and ethanol (60 ml) at 0° C. Potassium cyanide (15 g, 0.23 mol) and acetaldehyde (11.2 ml, 0.20 mol) were then added and the mixture was heated to reflux. After 15 h the volatiles were removed in vacuo and the residual solution was saturated with NaCi and was extracted with methylene chloride (3 times). The combined extracts were dried ($Na_2SO_4$) and evaporated in vacuo to an oil which was dissolved in 1M HCl (200 ml). The solution was evaporated in vacuo, azeotroping with 1:1 toluene/methanol to give a solid which was heated to reflux in ethyl acetate (200 ml), cooled, filtered and dried to give the title compound as the HCl salt:

$^1$H NMR (400 MHz, $CD_3OD$) d 1.72 (d, J=7.0 Hz, 3H, $CH_3$), 3.78–3.90 (m, 2H, $CH_2$), 4.63 (q, J=7.0 Hz, a-CH), 5.56–5.66 (m, 2H, CHC$\underline{H}_2$), 5.91–6.02 (m, 1H, C$\underline{H}$CH$_2$).

Step B: 1-Allyl-3,5-dichloro-6-methylpyrazinone

A stirred mixture of oxalyl chloride (30.5 ml, 0.35 mol) and α-(allylamino)-propionitrile hydrochloride (10.26 g, 70 mmol) in o-dichlorobenzene (100 ml) was heated to 100° C. for 15 h. The solvent was evaporated in vacuo and the residual black oil was purified by flash column chromatography on silica (eluting with 30% ethyl acetate hexanes) to give the title compound as a tan crystalline solid:

$^1$H NMR (400 Mz, $CDCl_3$) d 2.48 (s, 3H, $CH_3$), 4.75 (m, 2H, $NCH_2$), 5.18 (m, 1H, CHC$\underline{H}_AH_B$), 5.33 (m, 1H, CHCH$_A$$\underline{H}_B$), 5.85–5.92 (m, 1H, C$\underline{H}$CH$_A$H$_B$).

Step C: 3,5-Dichloro-6-methyl-1-carboxymethylpyrazinone

Ruthenium trichloride hydrate (114 mg, 0.547 mmol) was added to a stirred mixture of 1-allyl-3,5-dichloro-6-methylpyrazinone (5.45 g, 24.98 mmol) and sodium periodate (21.82 g, 0.102 mol) in water (75 ml), acetonitrile (50 ml) and carbon tetrachloride (50 ml). After 3 h the reaction mixture was extracted with methylene chloride (4 times) and the combined extracts were dried ($Na_2SO_4$) and evaporated in vacuo to a syrup. The 1H NMR ($CDCl_3$) of this material showed it to be a 1:1 mixture of the acid and the aldehyde. The crude mixture was dissolved in acetone (50 ml) and Jones Reagent (2.7M) was added until the reaction remained orange. The reaction was then extracted into ethyl acetate which was then washed with brine, dried ($Na_2SO_4$) and evaporated in vacuo to give the title compound as a tan solid:

$^1$H NMR (400 Mz, DMSO) d 2.41 (s, 3H, Me), 4.86 (s, 2H, $CH_2$).

Step D: 3-(4-Methoxybenzylamino)-5-chloro-6-methyl-1-carboxymethylpyrazinone

4-Methoxybenzylamine (0.83 ml, 6.33 mmol) was added to a stirred solution of 3,5-dichloro-6-methyl-1-carboxymethylpyrazinone (0.50 g, 2.11 mmol) in dioxane (6 ml) and the resulting mixture was warmed to 60° C. After 16 h the reaction mixture was partitioned between chloroform and 10% citric acid solution and the organic layer was dried ($Na_2SO_4$) and evaporated in vacuo. The crude product was purified by flash column chromatography (eluting with 2% methanol/chloroform/2% acetic acid) to give after azeotroping dry with toluene/methanol the title compound as a white solid:

$^1$H NMR (300 Mz, $CD_3OD$) d 2.27 (s, 3H, $CCH_3$), 3.76 (s, 3H, $OCH_3$), 4.46 (s, 2H, $CH_2$), 4.87 (s, 2H, $CH_2$), 6.85 (d, J=8.8 Hz, 1H, aryl H's), 7.27 (d, J=8.8 Hz, 1H, aryl H's).

Step E: 3-(4-Methoxybenzylamino)-6-methyl-1-carboxymethylpyrazinone

Raney nickel alloy (2 g) was added to a stirred solution of 3-(4-methoxybenzylamino)-5-chloro-6-methyl-1-carboxymethylpyrazinone (448 mg, 1.33 mmol) in 1:1 methanol/1$\underline{M}$ NaOH (50 ml). After 2 h the reaction mixture was filtered through celite, washing with 1:1 methanol/water and the filtrate was evaporated in vacuo to a white solid. The inorganic salts were removed by preparative HPLC (C18, water/acetonitrile/0.1% TFA gradient) to give the TFA salt of the title compound as a foam:

$^1$H NMR (300 Mz, $CDCl_3$) d 2.15 (s, 3H, $CCH_3$), 3.81 (s, 3H, $OCH_3$), 4.63 (s, 4H, 2×$CH_2$), 6.57 (s, 1H, pyrazinone H), 6.91(d, J=8.7 Hz, 1H, aryl H's), 7.30 (d, J=8.7 Hz, 1H, aryl H's).

Step F: 3-Amino-6-methyl-1-carboxymethylpyrazinone

A stirred solution of 3-(4-methoxybenzylamino)-6-methyl-1-carboxymethylpyrazinone (387 mg, 0.927 mmol) in TFA (8 ml) was heated to reflux for 6 h. The reaction was evaporated in vacuo azeotroping with methylene chloride and ethyl acetate. Methanol was added to the crude product and the resulting solids were filtered and dried to give the TFA salt of the title compound:

$^1$H NMR (400 Mz, $CD_3OD$) d 2.21 (s, 3H, $CH_3$), 4.81 (s, 2H, $CH_2$), 6.56 (s, 1H, pyrazinone H).

Step G: 3-Amino-6-Methyl-1-[Ethyl-(2-Methylcarboxamidomethyl-4-Chlorophenoxy)-Acetamido]-2-Pyrazinone EDC Hydrochloride (67 mg, 0.35 mmol) was added to a stirred mixture of 3-amino-6-methyl-1-carboxymethylpyrazinone (80 mg, 0.27 mmol), HOBT (47 mg, 0.35 mmol), ethyl-(2-aminomethyl-4-chlorophenoxy)-acetamide (85 mg, 0.35 mmol) and N-methylmorpholine (0.11 ml, 0.97 mmol) in DMF (1 ml) and the mixture was stirred for 16 h. Water was added to the reaction and the precipitated solid was collected by filtration and dried in vacuo. The crude product was suspended in ethyl acetate which was then heated to reflux, cooled and filtered, to give after drying the title compound as a white crystalline solid, m.p. >200° C.:

$^1$H NMR (300 Mz, DMSO) d 0.97 (t, J=7.2 Hz, 3H, $CH_2$C$\underline{H}_3$), 2.02 (s, 3H, $CH_3$), 3.09 (quintet, J=6.8 Hz, 2H, C$\underline{H}_2CH_3$), 4.37 (d, J=5.6 Hz, 2H, CONHC$\underline{H}_2$), 4.47 (s, 2H, $CH_2CO$), 4.63 (s, 2H, $CH_2CO$), 6.30 (br s, 2H, $NH_2$), 6.51 (s, 1H, pyrazinone H-5), 6.94 (d, J=9.3 Hz, 1H, phenoxy H-6), 7.28 (m, 2H, remainder), 7.98 (br t, 1 H, NH), 8.67 (br t, 1 H, NH); MS (FAB) 408 (M+1)$^+$.

EXAMPLE II

Preparation of 3-Amino-6-methyl-1-(2-amino-6-methyl-5-methylcarboxamidomethylpyridinyl)-pyrazinone

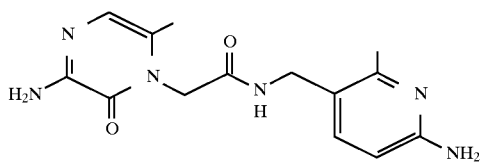

The title compound was prepared as the HCl salt from 3-amino-6-methyl-1-carboxymethylpyrazinone and 2-amino-5-aminomethyl-6-methylpyridine dihydrochloride using the procedure of EXAMPLE 1, Step G, m.p.>200° C.: MS (FAB) 303 (M+1)$^+$.

EXAMPLE III

Preparation of 3-(2-Phenethylamino)-5-chloro-6-methyl-1-(2-amino-6-methyl-5-methylcarboxamidomethylpyridinyl)-pyrazinone

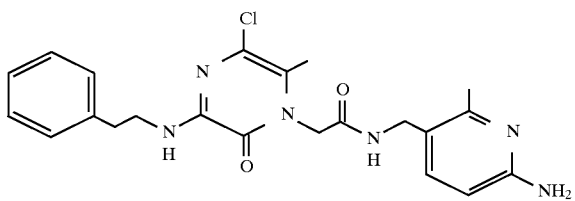

Step A: 3,5-Dichloro-6-methyl-1-(2-t-butoxycarbonylamino-6-methyl-5-methylcarboxamidomethylpyridinyl)-pyrazinone EDC Hydrochloride (249 mg, 1.3 mmol) was added to a stirred mixture of 3,5-dichloro-6-methyl-1-carboxymethylpyrazinone (237 mg, 1.0 mmol), HOBT (176 mg, 1.3 mmol), 5-aminomethyl-2-t-butoxycarbonylamino-6-methylpyridine (237 mg, 1.0 mmol) and N-methylmorpholine (0.25 ml, 2.3 mmol) in DMF (4 ml) and the mixture was stirred for 2 h. The reaction was diluted with ethyl acetate and was washed with 10% citric acid solution, water, sodium hydrogen carbonate solution and brine, dried (Na$_2$SO$_4$) and evaporated in vacuo to give the title compound as a foam:

$^1$H NMR (400 Mz, CDCl$_3$) d 1.51 (s, 9H, t-Bu), 2.39 (s, 3H, CH$_3$), 2.59 (s, 3H, CH$_3$), 4.37 (d, J=5.5 Hz, NHCH$_2$), 4.71 (s, 2H, CH$_2$CO), 6.76 (br t, 1H, NHCH$_2$), 7.14 (s, 1H, NHBOC), 7.44 (d, J=8.3 Hz, pyridine H-3), 7.66 (d, J=8.3 Hz, pyridine H-3).

Step B: 3-(2-Phenethylamino)-5-chloro-6-methyl-1-(2-t-butoxycarbonylamino-6-methyl-5-methylcarboxamidomethylpyridinyl)-pyrazinone Phenethylamine (0.10 ml, 0.80 mmol) was added to a stirred solution of 3,5-dichloro-6-methyl-1-(2-t-butoxycarbonylamino-6-methyl-5-methylenecarboxamidomethylpyridinyl)-pyrazinone (182 mg, 0.40 mmol) in dioxane (0.8 ml) and the resulting solution was warmed to 60° C. After 16 h the reaction mixture was partitioned between water and chloroform. The organic layer was dried (Na$_2$SO$_4$) and evaporated in vacuo. The crude product was purified by flash column chromatography on silica (ethyl acetate/hexanes gradient, 40–75% ethylacetate) to give the title compound.

$^1$H NMR (300 Mz, CDCl$_3$) d 1.51 (s, 9H, t-Bu), 2.36 (s, 3H, CH$_3$), 2.41 (s, 3H, CH$_3$), 2.92 (t, J=7.1 Hz, PhCH$_2$), 3.66 (q, J=7.1 Hz, PhCH$_2$CH$_2$), 4.35 (d, J=5.4 Hz, 2H, CONHCH$_2$), 4.63 (s, 2H, CH$_2$CO), 6.05 (br t, 1 H, NH), 6.54 (br t, 1 H, NH), 7.14 (s, 1 H, NHBOC), 7.21–7.31 (m, 5H, Ph), 7.43 (d, J=8.3 Hz, 1H, pyridine H-3), 7.69 (d, J=8.3 Hz, 1H, pyridine H-4).

Step C: 3-(2-Phenethylamino)-5-chloro-6-methyl-1-(2-amino-6-methyl-5-methylcarboxamidomethylpyridinyl)-pyrazinone HCl gas was bubbled through a solution of 3-(2-phenethylamino)-5-chloro-6-methyl-1-(2-t-butoxycarbonylamino-6-methyl-5-methylenecarboxamidomethylpyridinyl)-pyrazinone (83 mg, 0.153 mmol) in ethyl acetate (10 ml) at 0° C. for 10 min. The reaction was warmed to r.t. and after 1 h the solution was degassed with argon to give a white precipitate which was collected by filtration and dried to give the title compound as the HCl salt.

$^1$H NMR (400 Mz, CD$_3$OD) d 2.26 (s, 3H, CH$_3$), 2.50 (s, 3H, CH$_3$), 2.91 (t, J=7.0 Hz, PhCH$_2$), 3.60 (t, J=7.0 Hz, PhCH$_2$CH$_2$), 4.29 (s, 2H, CONHCH$_2$), 4.74 (s, 2H, CH$_2$CO), 6.82 (d, J=9.0 Hz, 1H, pyridine H-3), 7.18–7.29 (m, 5H, Ph), 7.83 (d, J=9.0 Hz, 1 H, pyridine H-4); MS (FAB) 441 (M+1)$^+$.

EXAMPLE IV

Preparation of 3-Benzylamino-5-chloro-6-methyl-1-(2-amino-6-methyl-5-methylcarboxamidomethylpyridinyl)-pyrazinone

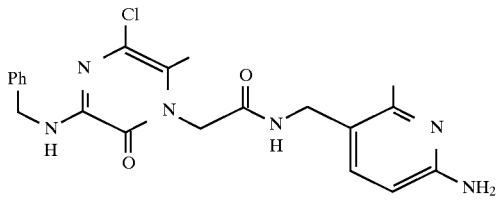

The title compound was prepared as the TFA salt from 3,5-dichloro-6-methyl-1-(2-t-butoxycarbonylamino-6-methyl-5-methylenecarboxamidomethylpyridinyl)-pyrazinone and benzylamine using the procedure of EXAMPLE III, Steps B and C: MS (FAB) 428 (M+1)$^+$.

EXAMPLE V

Preparation of 3-(2-Phenethylamino)-6-methyl-1-(2-amino-6-methyl-5-methylcarboxamidomethylpyridinyl)-pyrazinone

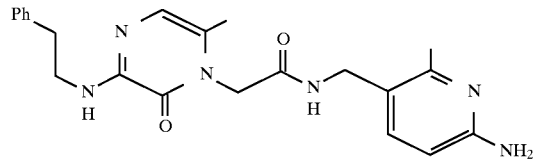

Step A: Benzyl-N-(1-cyanoethyl)glycine hydrochloride

TMSCN (18.8 mL, 141 mmol) was added cautiously (the reaction is exothermic) to a stirred solution of benzylglycine free base (23.3 g, 141 mmol—from the HCl salt by partition between EtOAc and brine basified with saturated Na$_2$CO$_3$ solution) and acetaldehyde (7.88 mL, 141 mmol) in methylene chloride (50 mL). After 4 h the volatiles were removed in vacuo and the residue was taken up in EtOAc and was washed with brine, dried (Na$_2$SO$_4$) and evaporated in vacuo to an oil. The oil was redissolved in EtOAc and 9.9M HCl in EtOH (15.25 mL, 151 mmol) was added to give a crystalline precipitate which was isolated by filtration, washing with EtOAc and Et$_2$O to give the title compound:

$^1$H NMR (CD$_3$OD): d 1.70 (d, J=7.0 Hz, 3H, CH$_3$), 4.16 (d, J=16.8 Hz, 1H, CH$_A$H$_B$), 4.21 (d, J=16.8 Hz, 1H, CH$_A$H$_B$), 4.64 (q, J=7.0 Hz, a-CH), 5.31 (s, 2H, CH$_2$O), 7.35–7.44 (m, 5H, Ph).

Step B: 1-Benzyloxycarbonylmethyl-3,5-dichloro-6-methylpyrazinone

A stirred mixture of oxalyl chloride (40.4 mL, 463 mmol) and benzyl-N-(1-cyanoethyl)glycine hydrochloride (29.51 g, 116 mmol) in 1,2-dichlorobenzene 110 mL) was heated to 100° C. for 15 h. The volatiles were evaporated in vacuo and the residue was purified by flash column chromatography on silica (eluting with hexanes followed by 30% ethyl acetate/hexanes) to give a solid which was heated to reflux in 2:5 EtOAc/hexanes (140 mL), cooled, and collected by filtration to give the title compound as a pale green crystalline solid:

$^1$H NMR (CDCl$_3$): d 2.35 (s, 3H, CH$_3$), 4.88 (s, 2H, CH$_2$), 5.24 (s, 2H, CH$_2$), 7.38 (m, 5H, Ph).

Step C: 3-(2-Phenethylamino)-5-chloro-6-methyl-1-(benzyloxycarbonylmethyl)-pyrazinone Phenethylamine (15.07 mL, 120 mmol) was added to a stirred mixture of 1-benzyloxycarbonylmethyl-3,5-dichloro-6-methylpyrazinone (13.09 g, 40 mmol) in EtOAc (80 mL) and the resulting mixture was heated to reflux under argon. After 2 h the reaction was cooled, diluted with chloroform (500 mL) and washed with 5% citric acid solution and brine, dried (Na$_2$SO$_4$) and evaporated in vacuo to give the title compound as a crystalline solid:

$^1$H NMR (CDCl$_3$): d 2.21 (s, 3H, CH$_3$), 2.93 (t, J=7.1 Hz, 2H, PhCH$_2$), 3.67 (q, J=6.7 Hz, 2H, CH$_2$NH), 4.79 (s, 2H, CH$_2$), 5.21 (s, 2H, CH$_2$), 6.10 (br t, 1H, NH), 7.20–7.39 (m, 10H, 2Ph).

Step D: 3-(2-Phenethylamino)-5-chloro-6-methyl-1-carboxymethylpyrazinone

LiOH.H$_2$O (3.36 g, 80 mmol) was added to a stirred suspension of the product from Step C in 3:3:1 THF/MeOH/H$_2$O (280 mL) at 0° C. and the mixture was warmed to RT. After 16 h the volatiles were evaporated in vacuo and the solution was diluted with water (500 mL) and was washed with EtOAc. The aqueous layer was saturated with NaCl and acidified with 20% KHSO$_4$ solution (20 mL) to give a precipitate which was extracted into 1:1 ethyl acetate/THF (400 mL). The organic layer was dried (Na$_2$SO$_4$) and evaporated in vacuo to a solid which was heated to reflux in 1:1 ethyl acetate/hexanes, cooled and collected by filtration to give the title compound as a crystalline solid:

$^1$H NMR (DMSO-d$_6$): d 2.21 (s, 3H, Me), 2.86 (t, J=7.4 Hz, 2H, PhCH$_2$), 3.47 (dt, J=5.9 and 7.4 Hz, 2H, CH$_2$NH), 4.72 (s, 2H, CH$_2$CO$_2$), 7.18–7.31 (m, 5H, Ph), 7.46 (t, J=5.9 Hz, 1H, NH), 13.30 (br s, 1H, COOH).

Step E: 3-(2-Phenethylamino)-6-methyl-1-carboxymethylpyrazinone 3-(2-Phenethylamino)-5-chloro-6-methyl-1-carboxymethylpyrazinone (11.66 g, 36.2 mmol) was added to a stirred solution of potassium hydroxide (86% by weight, 6.10 g, 93.5 mmol) in water (400 mL). After degassing the resulting solution with argon, 10% Pd/C (3.48 g) was added and the mixture was stirred under a hydrogen filled balloon. After 16 h, the mixture was degassed with nitrogen, more 10% Pd/C (3.0 g) was added and the mixture was stirred under a hydrogen filled balloon for a further 7 h, filtered through celite, washing the cake with water (200 mL). The filtrate was acidified with a solution of KHSO$_4$ (7.8 g, 57.3 mmol) in water (35 mL) and the resulting precipitate was collected by filtration, washing with water (200 mL), and was dried for 16 h in vacuo to give the title compound as a crystalline solid:

$^1$H NMR (DMSO-d$_6$): d 2.07 (d, J=0.7 Hz, 3H, Me), 2.84 (t, J=7.4 Hz, 2H, PhCH$_2$), 3.47 (dt, J=5.9 and 7.4 Hz, 2H, CH$_2$NH), 4.66 (s, 2H, CH$_2$CO$_2$), 6.67 (s, 1H, pyrazinone H-5), 6.88 (br t, J=5.9 Hz, 1H, NH), 7.17–7.32 (m, 5H, Ph).

Step F: 3-(2-Phenethylamino)-6-methyl-1-(2-amino-6-methyl-5-methylcarboxamidomethylpyridinyl)-pyrazinone EDC.HCl (0.962 g, 5.02 mmol) was added to a stirred mixture of 3-(2-phenethylamino)-6-methyl-1-carboxymethylpyrazinone (1.20 g, 4.18 mmol), 2-amino-5-aminomethyl-6-methylpyridine dihydrochloride (0.874 g, 4.16 mmol), HOBT.H$_2$O (0.678 g, 5.02 mmol) and N-methylmorpholine (2.30 mL, 20.9 mmol) in dry DMF (10 mL). After 16 h, the volatiles were evaporated in vacuo and the residue was partitioned between ethyl acetate and 1M HCl solution. The aqueous layer was adjusted to pH 10 with saturated sodium carbonate solution and the precipitate was collected by filtration, washing with water and ethanol to give the title compound as the free base.

The free base material was used as a starting material to form 3-(2-Phenethylamino)-6-methyl-1-(2-amino-6-methyl-5-methylcarboxamidomethylpyridinyl)-pyrazinone dihydrochloride (Step G1), 3-(2-Phenethylamino)-6-methyl-1-(2-amino-6-methyl-5-methylcarboxamidomethylpyridinyl)-pyrazinone dihydrochloride Type A monohydrate (Step G2, also referred to as "polymorphic crystalline form Type A monohydrate") or 3-(2-Phenethylamino)-6-methyl-1-(2-amino-6-methyl-5-methylcarboxamidomethylpyridinyl)-pyrazinone dihydrochloride Type B monohydrate (Step G3, also referred to as "polymorphic crystalline form Type B monohydrate").

In general, production of 3-(2-Phenethylamino)-6-methyl-1-(2-amino-6-methyl-5-methylcarboxamidomethylpyridinyl)-pyrazinone dihydrochloride Type A monohydrate comprises the steps of a) dissolving 3-(2-Phenethylamino)-6-methyl-1-(2-amino-6-methyl-5-methylcarboxamidomethylpyridinyl)-pyrazinone in acetic acid solvent and adding aqueous HCl; b) recovering the resultant solid phase; and c) removing the solvent therefrom. In one aspect of this process, the amount of aqueous HCl added in step a) is such that the final water content in the acetic acid is between 1 and 5 weight %.

In general, production of 3-(2-Phenethylamino)-6-methyl-1-(2-amino-6-methyl-5-methylcarboxamidomethylpyridinyl)-pyrazinone dihydrochloride Type B monohydrate comprises the steps of a) dissolving 3-(2-Phenethylamino)-6-methyl-1-(2-amino-6-methyl-5-methylcarboxamidomethylpyridinyl)-pyrazinone in hydrochloric acid solvent; b) recovering the resultant solid phase; and c) removing the solvent therefrom.

Step G1 3-(2-Phenethylamino)-6-methyl-1-(2-amino-6-methyl-5-methylcarboxamidomethylpyridinyl)-pyrazinone dihydrochloride 3-(2-Phenethylamino)-6-methyl-1-(2-amino-6-methyl-5-methylcarboxamidomethylpyridinyl)-pyrazinone free base was suspended in ethanol (20 mL) and ethanolic HCl (9.9M, 8.36 mmol) was added with stirring at 0° C. The bis-HCl salt rapidly crystallizes from the mixture and after 30 min it was collected by filtration, washing with ethanol, and was dried for 16 h at 0.5 mm Hg to give the title compound;

$^1$H NMR (DMSO-d$_6$): d 2.10 (s, 3H, CH$_3$), 2.45 (s, 3H, CH$_3$), 2.91 (t, J=7.6 Hz, PhCH$_2$), 3.63 (br q, CH$_2$NH), 4.17 (d, J=5.5 Hz, 2H, CONHCH$_2$), 4.62 (s, 2H, CH$_2$CO), 6.68

(s, 1H, pyrazinone H-5), 6.81 (d, J=9.0 Hz, 1H, pyridine H-3), 7.21–7.31 (m, 5H, Ph), 7.76 (obscured d, 1H, pyridine H-4), 7.77 (br s, 2H, NH$_2$), 8.81 (br t, J=5.5 Hz, 1H, CONH).

Step G2 3-(2-Phenethylamino)-6-methyl-1-(2-amino-6-methyl-5-methylcarboxamidomethylpyridinyl)-pyrazinone dihydrochloride Type A monohydrate 3-(2-phenethyl-amino)-6-methyl-1-(2-amino-6-methyl-5-methylene-carboxamidomethylpyridinyl)-pyrazinone free base (680 g) was dissolved in 6.0 L of acetic acid and the mixture was stirred with warming to 60° C. to obtain a solution. The mixture was filtered and the filter flushed with 7.6 L of acetic acid and aqueous HCl (734 mL 5N HCl and 147 mL water) was added to the cooled solution at 28° C. The mixture was seeded and warmed to 73° C. to give a fine seed bed, then cooled to 20° C. over several h and filtered and the filter cake washed with acetic acid followed by 190 proof ethanol and dried at 60° C. in the vacuum oven with a nitrogen purge to give the title compound.

The Type A compound is characterized by a differential scanning calorimetry (DSC) curve, at a heating rate of 5° C./min in an open cup under flowing nitrogen bubbled through water at 5° C. exhibiting an endotherm with an extrapolated onset temperature of about 102° C., a peak temperature of about 112° C. and an associated heat of about 115 J/gm followed by an endotherm with an extrapolated onset temperature of about 171° C., a peak temperature of about 194° C. and an associated heat of about 83 J/gm. The low temperature endotherm is due to the loss of the water of hydration and the high temperature endotherm is due to melting with decomposition of the remaining anhydrous phase. The x-ray powder diffraction pattern is characterized by d-spacings of 13.06, 12.16, 7.40, 5.71, 4.92, 4.48, 4.40, 3.63, 3.07, 2.98, 2.86 and 2.62 Å.

Step G3 3-(2-Phenethylamino)-6-methyl-1-(2-amino-6-methyl-5-methylcarboxamidomethylpyridinyl)-pyrazinone dihydrochloride Type B monohydrate A 100 liter vessel was charged with 8.12 liters of 2N hydrochloric acid (HCl), followed by the addition of 1.62 liters of DI water, at ambient temperature. To the vessel was added 3-(2-phenethyl-amino)-6-methyl-1-(2-amino-6-methyl-5-methylene-carboxamidomethylpyridinyl)-pyrazinone free base (3.30 kg) and the contents were heated to 82° C. After aging for 15 minutes, Solka flok (24 g) was added and the resulting solution was filtered via residual vacuum through consecutive line filters (20 and 5 micron). The original vessel was rinsed with 3.25 liters of DI water (ambient temperature), which was combined with the original filtrate and reheated to 72° C. The solution was cooled to 53° C., seeded, and the cooling continued to 25° C. over 3 hours. Concentrated hydrochloric acid (1.30 liters) was added dropwise over 30 minutes to the slurry. The slurry was cooled to 20° C. and the solids isolated via vacuum filtration. The cake was washed with 6.48 liters of 1N HCl. The cake was then washed with ethanol (190 proof; 3×6.48 liters). The wet cake was dried in vacuo at ambient temperauture to give the title compound.

The Type B compound is characterized by a differential scanning calorimetry (DSC) curve, at a heating rate of 5° C./min in an open cup under flowing nitrogen bubbled through water at 5° C. exhibiting an endotherm with an extrapolated onset temperature of about 120° C., a peak temperature of about 132° C., and an associated heat of about 123 J/gm followed by an endotherm with an extrapolated onset temperature of about 160° C., a peak temperature of about 191° C. and an associated heat of about 78 J/gm. The low temperature endotherm is due to the loss of the water of hydration and the high temperature endotherm is due to melting with decomposition of the remaining anhydrous phase. The x-ray powder diffraction pattern is characterized by d-spacings of 12.98, 11.91, 7.24, 5.98, 4.90, 4.46, 4.23, 3.99, 3.75, 3.61, 3.41, 2.94, 2.85 and 2.61 Å.

EXAMPLE VI 3-(2-Phenethylamino)-6-Methyl-1-[Ethyl-(2-Methylcarboxamidomethyl-4-Chlorophenoxy)-Acetamido]-2-Pyrazinone

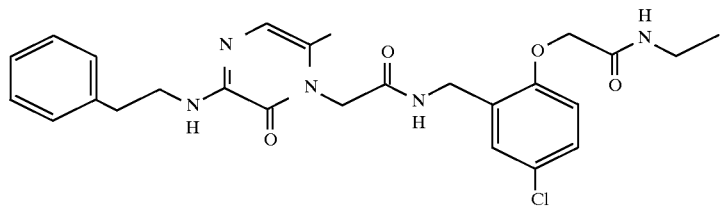

EDC Hydrochloride (56 mg, 0.29 mmol) was added to a stirred mixture of 3-(2-phenethylamino)-6-methyl-1-carboxymethylpyrazinone (91 mg, 0.23 mmol), HOBT (40 mg, 0.29 mmol), ethyl-(2-aminomethyl-4-chlorophenoxy)-acetamide hydrochloride (82 mg, 0.29 mmol) and N-methylmorpholine (0.13 ml, 1.17 mmol) in DMF (1 ml) and the mixture was stirred for 16 h. The reaction was partitioned between ethyl acetate and water, adding sufficient brine to disperse the emulsion. The cloudy organic layer was collected and the solids dissolved by adding chloroform and methanol, and the solution was dried and evaporated to a solid. The crude product was suspended in ethyl acetate and filtered, washing with water followed by ethyl acetate to give after drying the title compound as a white crystalline solid, m.p.>200° C.:

$^1$H NMR (400 Mz, DMSO) d 0.97 (t, J=7.2 Hz, 3H, CH$_2$CH$_3$), 2.03 (s, 3H, CH$_3$), 2.83 (t, J=7.4 Hz, 2H, PhCH$_2$), 3.09 (quintet, J=6.7 Hz, 2H, CH$_2$CH$_3$), 3.47 (q, J=6.9 Hz, 2H, PhCH$_2$CH$_2$), 4.37 (d, J=5.7 Hz, 2H, CONHCH$_2$), 4.64 (s, 2H, CH$_2$CO), 6.63 (s, 1H, pyrazinone H-5), 6.77 (br t, 1H, NH), 6.94 (d, J=8.4 Hz, 1H, phenoxy H-6), 7.16–7.30 (m, 7H, remainder), 7.98 (br t, 1H, NH), 8.67 (br t, 1H, NH); MS (FAB) 512 (M+1)$^+$.

EXAMPLE VII

Preparation of [R]-3-(1-Phenyl-2-propylamino)-6-methyl-1-(2-amino-6-methyl-5-methylcarboxamidomethylpyridinyl)-pyrazinone

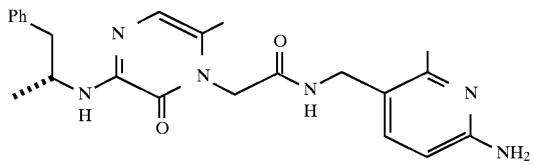

The title compound was prepared as the HCl salt from 1-benzyloxycarbonylmethyl-3,5-dichloro-6-methylpyrazinone and [R]-1-phenyl-2-propylamine using the procedure of EXAMPLE V, Steps C–F: MS (FAB) 421 (M+1)$^+$.

EXAMPLE VIII

Preparation of [S]-3-(1-Phenyl-2-propylamino)-6-methyl-1-(2-amino-6-methyl-5-methylcarboxamidomethylpyridinyl)-pyrazinone

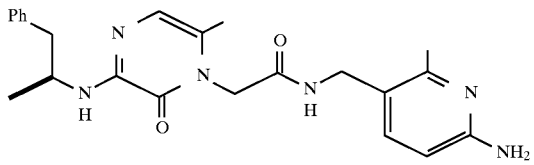

The title compound was prepared as the HCl salt from 1-benzyloxycarbonylmethyl-3,5-dichloro-6-methylpyrazinone and [S]-1-phenyl-2-propylamine using the procedure of EXAMPLE V, Steps C–F: MS (FAB) 421 (M+1)$^+$.

EXAMPLE IX

Preparation of 3-(1-Phenyl-2-methyl-2-propylamino)-6-methyl-1-(2-amino-6-methyl-5-methylcarboxamidomethylpyridinyl)-pyrazinone

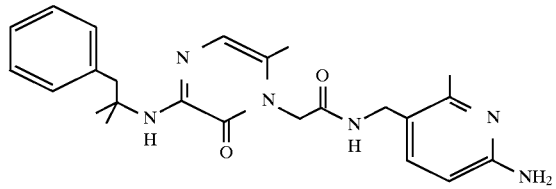

The title compound was prepared as the HCl salt from 1-benzyloxycarbonylmethyl-3,5-dichloro-6-methylpyrazinone and 1-phenyl-2-methyl-2-propylamine using the procedure of EXAMPLE V, Steps C–F: MS (FAB) 435 (M+1)$^+$.

EXAMPLE X

Preparation of 3-(2-Methyl-2-propylamino)-6-methyl-1-(2-amino-6-methyl-5-methylcarboxamidomethylpyridinyl)-pyrazinone

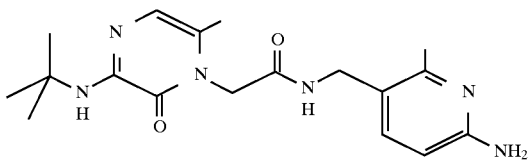

The title compound was prepared as the HCl salt from 1-benzyloxycarbonylmethyl-3,5-dichloro-6-methylpyrazinone and 2-methyl-2-propylamine using the procedure of EXAMPLE V, Steps C–F: MS (FAB) 358 (M+1)$^+$.

EXAMPLE XI

Preparation of 3-(2-Phenethylamino)-6-methyl-1-(2-amino-4,6-dimethyl-5-methylcarboxamidomethylpyridinyl)-pyrazinone

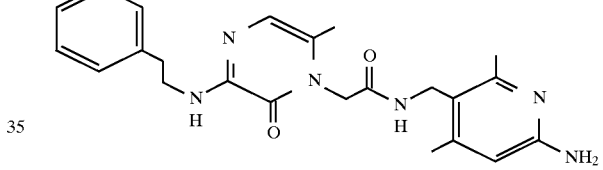

The title compound was prepared as the HCl salt from 3-(2-phenethylamino)-6-methyl-1-methylcarboxypyrazinone and 2-amino-5-aminomethyl-4,6-dimethylpyridine dihydrochloride using the procedure of EXAMPLE V, Step F, m.p.>200° C.: MS (FAB) 421 (M+1)$^+$.

EXAMPLE XII

Preparation of [R,S]-3-(2-Phenyl-1-propylamino)-6-methyl-1-(2-amino-6-methyl-5-methylcarboxamidomethylpyridinyl)-pyrazinone

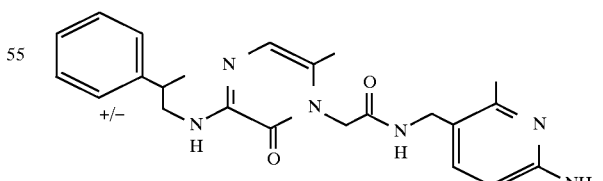

The title compound was prepared as the HCl salt from 1-benzyloxycarbonylmethyl-3,5-dichloro-6-methylpyrazinone and rac-2-phenyl-1-propylamine using the procedure of EXAMPLE V, Steps C–F, m.p.>200° C.: MS (FAB) 421 (M+1)$^+$.

EXAMPLE XIII
Preparation of 3-(2-Propylamino)-6-methyl-1-(2-amino-6-methyl-5-methylcarboxamidomethylpyridinyli)-pyrazinone

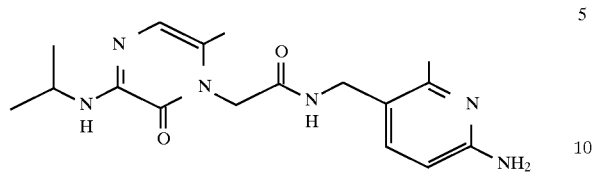

The title compound was prepared as the HCl salt from 1-benzyloxycarbonylmethyl-3,5-dichloro-6-methylpyrazinone and 2-propylamine using the procedure of EXAMPLE V, Steps C–F, m.p.>200° C.: MS (FAB) 345 (M+1)$^+$.

EXAMPLE XIV
Preparation of 3-(2-Phenoxyethylamino)-6-methyl-1-(2-amino-6-methyl-5-methylcarboxamidomethylpyyridinyl)-pyrazinone

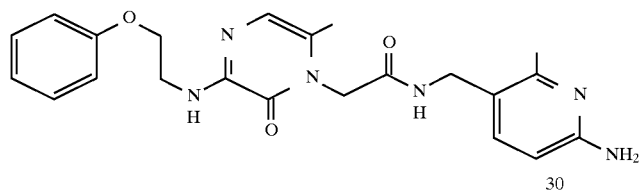

The title compound was prepared as the HCl salt from 1-benzyloxycarbonylmethyl-3,5-dichloro-6-methylpyrazinone and 2-phenoxyethylamine using the procedure of EXAMPLE V, Steps C–F, m.p.>200° C.: MS (FAB) 423 (M+1)$^+$.

EXAMPLE XV
Preparation of 3-[2-(4-Hydroxyphenyl)-ethyl-amino]-6-methyl-1-(2-amino-6-methyl-5-methylcarboxamidomethylpyridinyl)-pyrazinone

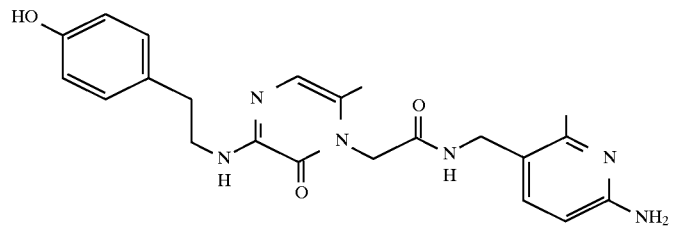

The title compound was prepared as the HCl salt from 1-benzyloxycarbonylmethyl-3,5-dichloro-6-methylpyrazinone and 2-(4-hydroxyphenyl)-ethylamine using the procedure of EXAMPLE V, Steps C–F, m.p. 195°–199° C.: MS (FAB) 423 (M+1)$^+$.

EXAMPLE XVI

Preparation of 3-Cyclopropylamino-6-methyl-1-(2-amino-6-methyl-5-methylcarboxamidomethylpyridinyl)-pyrazinone

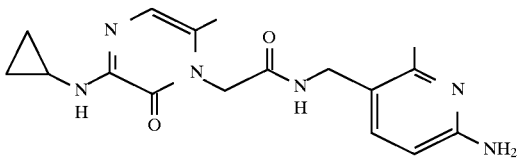

The title compound was prepared as the TFA salt from 1-benzyloxycarbonylmethyl-3,5-dichloro-6-methylpyrazinone and cyclopropylamine using the procedure of EXAMPLE V, Steps C–F: MS (FAB) 343 (M+1)$^+$.

EXAMPLE XVII

Preparation of 3-Cyclopropylmethylamino-6-methyl-1-(2-amino-6-methyl-5-methylcarboxamidomethylpyridinyl)-pyrazinone

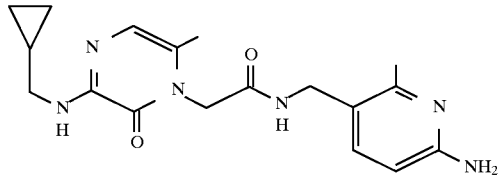

The title compound was prepared as the HCl salt from 1-benzyloxycarbonylmethyl-3,5-dichloro-6-methylpyrazinone and cyclopropylmethylamine using the procedure of EXAMPLE V, Steps C–F, m.p.>200° C.: MS (FAB) 357 (M+1)$^+$.

Preparation of [S]-3-(2-Hydroxy-2-phenethylamino)-6-methyl-1-(2-amino-6-methyl-5-methylcarboxamidomethylpyridinyl)-pyrazinone

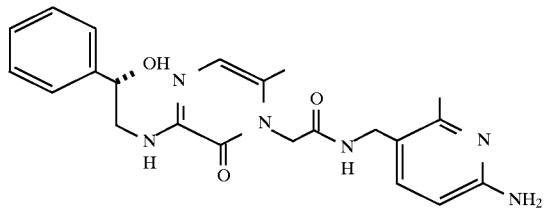

The title compound was prepared as the HCl salt from 1-benzyloxycarbonylmethyl-3,5-dichloro-6-methylpyrazinone and [S]-2-hydroxyphenethylamine using the procedure of EXAMPLE V, Steps C–F, m.p.>200° C.: MS (FAB) 423 (M+1)$^+$.

EXAMPLE XIX

Preparation of [R]-3-(2-Hydroxy-2-phenethylamino)-6-methyl-1-(2-amino-6-methyl-5-methylcarboxamidomethylpyridinyl)-pyrazinone

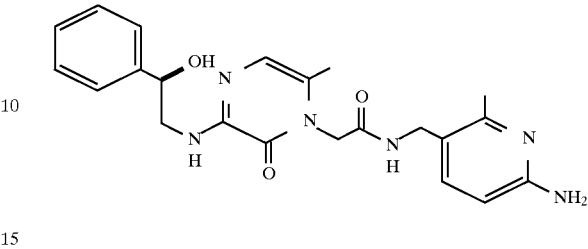

The title compound was prepared as the HCl salt from 1-benzyloxycarbonylmethyl-3,5-dichloro-6-methylpyrazinone and [R]-2-hydroxyphenethylamine using the procedure of EXAMPLE V, Steps C–F: MS (FAB) 423 (M+1)$^+$.

EXAMPLE XX

Preparation of 3-(2-Cyclopropylethylamino)-6-methyl-1-(2-amino-6-methyl-5-methylcarboxamidomethylpyridinyl)-pyrazinone

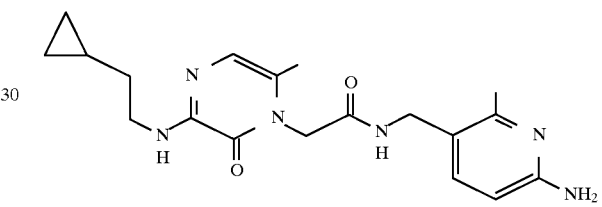

Step A: 4-Phthalimido-1-butene

A mixture of 4-bromo-1-butene (1.01 mL, 10.0 mmol) and potassium phthalimide (1.85 g, 10.0 mmol) in DMF (10 mL) was stirred at 100° C. for 3 h. The resulting mixture was cooled and partitioned between ethyl acetate and water. The organic layer was washed with water and brine, dried (Na$_2$SO$_4$) and evaporated in vacuo to a crystalline solid. The crude product was purified by flash column chromatography on silica (eluting with 20% ethyl acetate/hexanes) to give the title compound as a crystalline solid:

$^1$H NMR (300 Mz, CDCl$_3$) d 2.45 (q, J=7.0 Hz, 2H), 3.78 (t, J=7.0 Hz, 2H), 5.04 (m, 2H), 5.76 (m, 1H), 7.71 (m, 2H), 7.84 (m, 2H).

Step B: 2-Phthalimidoethylcyclopropane

4-Phthalimido-1-butene was cyclopropanated using the procedure of Suda (Synthesis, 1981, 714) to give the title compound as a crystalline solid:

$^1$H NMR (400 Mz, CDCl$_3$) d 0.05 (m, 2H), 0.42 (m, 2H), 0.69 (m, 1H), 1.58 (q, J=7.1 Hz, 2H), 3.77 (t, J=7.1 Hz, 2H), 7.71 (m, 2H), 7.84 (m, 2H).

Step C: 2-Cyclopropylethylamine

A mixture of 2-phthalimidoethylcyclopropane (1.40 g, 6.50 mmol) and hydrazine hydrate (0.32 mL, 6.50 mmol) in ethanol (10 mL) was stirred at reflux for 1 h. The mixture was cooled and cHCl (0.54 mL, 6.50 mmol) was added to give a thick precipitate. The mixture was evaporated in vacuo and the residue was suspended in 1M HCl solution (10 mL) and warmed to 50° C. for 5 min, cooled and filtered. The filtrate was washed with methylene chloride and then was evaporated in vacuo, azeotroping with toluene/ethanol to give the HCl salt of the title compound as a crystalline solid:

$^1$H NMR (400 Mz, CD$_3$OD) d 0.15 (m, 2H), 0.54 (m, 2H), 0.74 (m, 1H), 1.55 (q, J=7.3 Hz, 2H), 3.01 (t, J=7.3 Hz, 2H).

Step D: 3-(2-Cyclopropylethylamino)-5-chloro-6-methyl-1-(benzyloxycarbonylmethyl)-pyrazinone A mixture of 2-cyclopropylethylamine hydrochloride (73 mg, 0.60 mmol), 1-benzyloxycarbonylmethyl-3,5-dichloro-6-methylpyrazinone (164 mg, 0.50 mmol) and sodium hydrogen carbonate (101 mg, 1.20 mmol) in toluene (1 mL) and water (0.5 mL) was stirred at 80° C. for 3 h. The reaction was then cooled and partitioned between methylene chloride and 10% citric acid solution. The organic layer was dried (Na$_2$SO$_4$) and evaporated in vacuo to give the title compound as a crystalline solid:

$^1$H NMR (400 MHz, CDCl$_3$): d 0.10 (m, 2H), 0.47 (m, 2H), 0.74 (m, 1H), 1.53 (q, J=7.0 Hz, 2H), 2.21 (s, 3H, CH$_3$), 3.49 (q, J=6.6 Hz, 2H), 4.80 (s, 2H), 5.22 (s, 2H), 6.18 (br t, 1H), 7.33–7.40 (m, 5H).

Step E: 3-(2-Cyclopropylethylamino)-6-methyl-1-(2-amino-6-methyl-5-methylcarboxamidomethylpyridinyl)-pyrazinone The title compound was from 3-(2-cyclopropylethylamino)-5-chloro-6-methyl-1-(benzyloxycarbonylmethyl)-pyrazinone using the procedure of EXAMPLE V, Steps D–F, m.p.>200° C.: MS (FAB) 371 (M+1)$^+$.

EXAMPLE XXI

Preparation of 3-(2-Phenethylamino)-6-ethyl-1-(2-amino-6-methyl-5-methylcarboxamidomethylpyridinyl)-pyrazinone

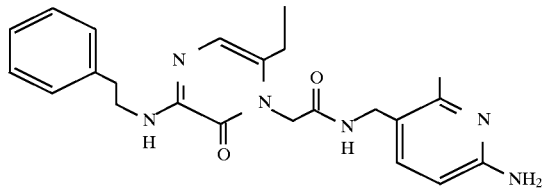

The title compound was prepared as the HCl salt from propionaldehyde using the procedure of EXAMPLE V: MS (FAB) 421 (M+1)$^+$.

EXAMPLE XXII

Preparation of 3-(2-Phenethylamino)-6-methyl-1-(2-amino-5-methylcarboxamidomethylpyridinyl)-pyrazinone

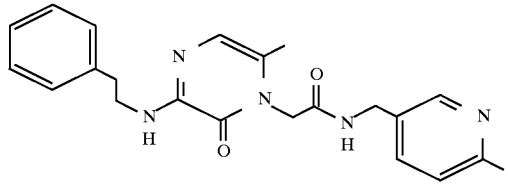

The title compound was prepared as the HCl salt from 3-(2-phenethylamino)-6-methyl-1-carboxymethylpyrazinone and 2-amino-5-aminomethylpyridine using the procedure of EXAMPLE V, Step F, m.p.>220° C.: MS (FAB) 393 (M+1)$^+$.

EXAMPLE XXIII

Preparation of 3-(5-Indanylmethylamino)-6-methyl-1-(2-amino-6-methyl-5-methylcarboxamidomethylpyridinyl)-pyrazinone

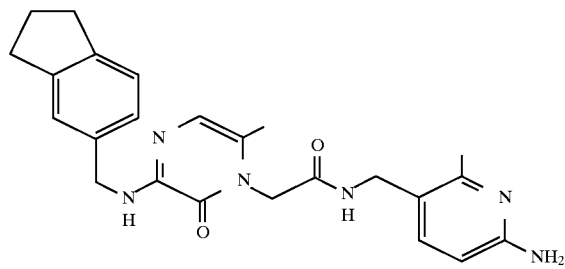

The title compound was prepared as the TFA salt from 1-benzyloxycarbonylmethyl-3,5-dichloro-6-methylpyrazinone and 5-indanylmethylamine using the procedure of EXAMPLE V, Steps C–F: MS (FAB) 434 (M+1)$^+$.

EXAMPLE XXIV

Preparation of 3-(2-Phenethylamino)-6-methyl-1-[Ethyl-(2-Methylcarboxamidomethylphenoxy)-Acetamido]-pyrazinone

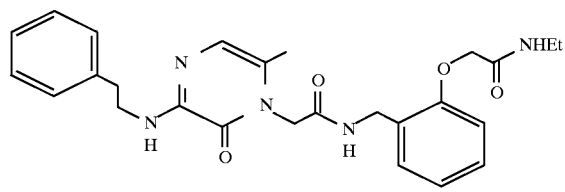

The title compound was prepared from 3-(2-phenethylamino)-6-methyl-1-carboxymethylpyrazinone and ethyl-2-aminomethylphenoxyacetamide using the procedure of EXAMPLE VI: MS (FAB) 478 (M+1)$^+$.

EXAMPLE XXV

Preparation of 3-(4-Methoxybenzylamino)-6-methyl-1-[Ethyl-(2-Methylcarboxamidomethyl-4-chlorophenoxy)-Acetamido]-pyrazinone

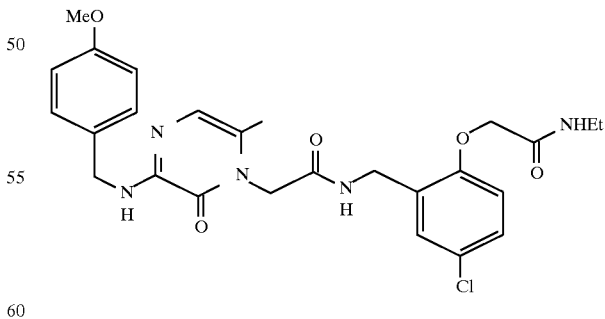

The title compound was prepared from 1-benzyloxycarbonylmethyl-3,5-dichloro-6-methylpyrazinone and 4-methoxybenzylamine using the procedure of EXAMPLE V, Steps C–E, followed by the procedure of EXAMPLE VI, m.p.>200° C.: MS (FAB) 528 (M+1)$^+$.

EXAMPLE XXVI

Preparation of 3-(2-Phenethylamino)-6-methyl-1-(Methylcarboxamido-methyl-2-hydroxy-5-chlorophenyl)-pyrazinone

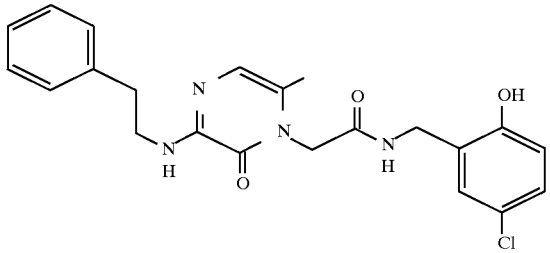

The title compound was prepared from 3-(2-phenethylamino)-6-methyl-1-carboxymethylpyrazinone and 2-aminomethyl-4-chlorophenol using the procedure of EXAMPLE VI: MS (FAB) 427 (M+1)⁺.

EXAMPLE XXVII

Preparation of 3-(2-Phenethylamino)-6-methyl-1-[Ethyl-(2-Methylcarboxamidomethyl-4-chlorophenoxy)-Acetyl]-pyrazinone

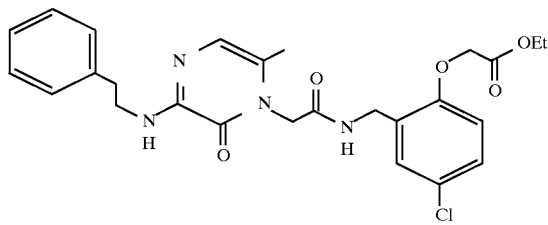

The title compound was prepared from 3-(2-phenethylamino)-6-methyl-1-carboxymethylpyrazinone and ethyl-2-aminomethylmethyl-4-chlorophenoxyacetate using the procedure of EXAMPLE VI: MS (FAB) 513 (M+1)⁺.

EXAMPLE XXVIII

Preparation of 3-(2-Methyl-2-propylamino)-6-methyl-1-[Ethyl-(2-Methylcarboxamidomethyl-4-chlorophenoxy)-Acetamido]-pyrazinone

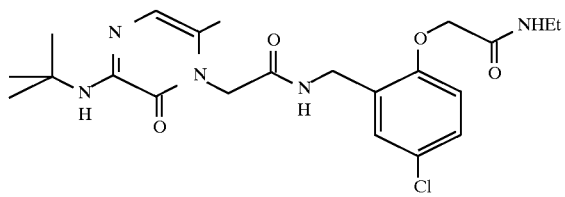

The title compound was prepared as the TFA salt from 3-(2-methyl-2-propylamino)-6-methyl-1-carboxymethylpyrazinone using the procedure of EXAMPLE VI, m.p. 64°–70° C.: MS (FAB) 464 (M+1)⁺.

EXAMPLE XXIX

Preparation of rac-trans-3-(2-Phenylcyclohexylamino)-6-methyl-1-(2-amino-6-methyl-5-methylcarboxamidomethylpyridinyl)-pyrazinone

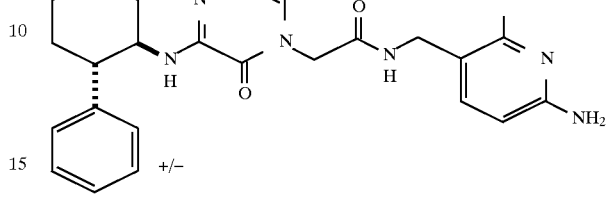

The title compound was prepared as the HCl salt from 1-benzyloxycarbonylmethyl-3,5-dichloro-6-methylpyrazinone and rac-trans-2-phenylcyclohexylamine using the procedure of EXAMPLE V, Steps C–E, followed by the procedures of METHOD 4: MS (FAB) 461 (M+1)⁺.

EXAMPLE XXX

Preparation of rac-cis-3-(2-Phenylcyclohexylamino)-6-methyl-1-(2-amino-6-methyl-5-methylcarboxamidomethylpyridinyl)-pyrazinone

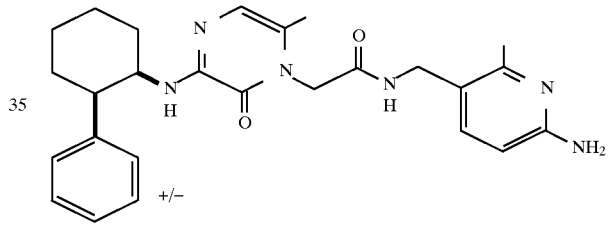

The title compound was prepared as the HCl salt from 1-benzyloxycarbonylmethyl-3,5-dichloro-6-methylpyrazinone and rac-cis-2-phenylcyclohexylamine using the procedure of EXAMPLE V, Steps C–E, followed by the procedures of METHOD 4: MS (FAB) 461 (M+1)⁺.

EXAMPLE XXXI

Preparation of 3-(2-Phenethylamino)-6-methyl-1-(2-amino-4-methylcarboxamidomethylpyridinyl)-pyrazinone

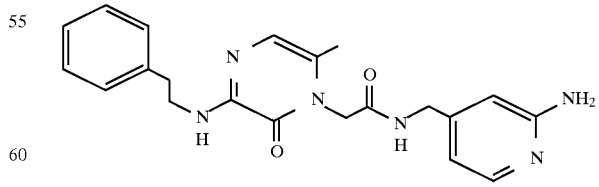

The title compound was prepared as the HCl salt from 3-(2-phenethylamino)-6-methyl- -methylcarboxypyrazinone and 2-amino-4-aminomethylpyridine using the procedure of EXAMPLE V, Step F: MS (FAB) 393 (M+1)⁺.

EXAMPLE XXXII

Preparation of 3-(2-Phenethylamino)-6-methyl-1-(2-amino-3-methyl-4-methylcarboxamidomethylpyridinyl)-pyrazinone

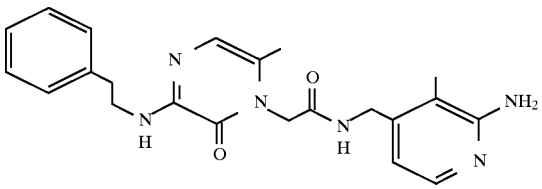

Step A: 2-t-Butyloxycarbonylamino-3-methylpyridine-N-oxide

To a 0° C. solution of 1.0 g (4.8 mmol) of 2-t-butyloxycarbonylamino-3-methylpyridine in 25 mL of CH$_2$Cl$_2$, was added 25 mL of 5% NaHCO$_3$. Five portions of 1.73 g (5 mmol) of 3-chloroperoxybenzoic acid were added over a 20 min period to the rapidly stirred mixture. The cold bath was allowed to expire overnight, and the reaction mixture quenched with 10% Na$_2$SO$_3$. After stirring for 5 min, the aqueous layer was extracted with CH$_2$Cl$_2$, dried over Na$_2$SO4, treated with activated carbon and the solvents removed to give an oil that was chromatographed on 50 g fine SiO2 using 98:2 to 96:4 CHCl$_3$—OH$_3$OH to give the title compound as an off-white solid:

$^1$H NMR (CDCl$_3$) δ 8.23 (s, 1H), 8.12 (d, 1H, 6.6 Hz), 7.15 (d, 1H, 6.8 Hz), 6.98 (t, 1H, 6.3 Hz), 2.36 (s, 3H), 1.52 (s, 9H).

Step B: 2-t-Butyloxycarbonylamino-3-methyl-1-methoxy-pyridinium methyl sulfate

To a stirred solution of 620 mg (0.29 mmol) of 2-t-butyloxycarbonylamino-3-methylpyridine-N-oxide in 8 mL of CH$_2$Cl$_2$ under Ar was added 262 μL (0.3 mmol) of dimethyl sulfate. The CH$_2$Cl$_2$ was allowed to evaporate under a slow stream of Ar overnight to give the title compound as a light tan solid:

$^1$H NMR (DMSO-d$_6$) δ 10.8 (s, 1H), 9.32 (d, 1H, 6.6 Hz), 8.50 (d, 1H, 7.8 Hz), 7.98 (t, 1H, 7.1 Hz), 4.28 (s, 3H), 3.37 (s, 3H), ), 2.41 (s, 3H), 1.49 (s, 9H).

Step C: 2-t-Butyloxycarbonylamino-4-cyano-3-methylpyridine

The product from the previous reaction was heated with 651 mg (10 mmol) potassium cyanide in 4.5 mL of water at 50° C. overnight. The reaction was diluted with water and 10% Na$_2$CO$_3$, extracted with 3×CHCl$_3$, the combined organic layers were washed with brine, dried over Na$_2$SO$_4$ and the solvents removed to give a dark oil that was dissolved in CHCl3 and applied to a column of 20 g fine SiO$_2$. The column was eluted with 1:4–1:3 EtOAc-hexane to give the title compound as a colorless solid:

$^1$H NMR (CDCl$_3$) δ 7.64 (d, 1H, 7.7 Hz), 7.44 (d, 1H, 7.7 Hz), 6.80 (s, 1H), 2.38 (s, 3H), 1.52 (s, 9H).

Step D: 4-Aminomethyl-2-t-butyloxycarbonylamino-3-methylpyridine

A solution of 175 mg (0.75 mmol) of 2-t-butyloxycarbonylamino-4-cyano-3-methylpyridine and 88 μL (1.5 mmol) of acetic acid in 10 mL of MeOH was hydrogenated over 75 mg of 10% Pd-C at 55 psi overnight on a Parr apparatus. The catalyst was removed by filtration, concentrated at reduced pressure, and the residue partitioned between CHCl$_3$ and 10% Na$_2$CO$_3$. The aqueous layer was extracted with CHCl$_3$ and the combined organic layers were dried over Na2SO4 and concentrated to give 150 mg of the title compound as a colorless oil:

$^1$H NMR (CDCl$_3$) δ 7.48 (d, 1H, 7.7 Hz), 7.02 (d, 1H, 7.7 Hz), 6.69 (s, 1H), 3.88 (s, 2H), 2.28 (s, 3H), 1.51 (s, 9H).

Step E: 3-(2-Phenethylamino)-6-methyl-1-(2-amino-3-methyl-4-methylcarboxamidomethylpyridinyl)-pyrazinone The title compound was prepared as the TFA salt from 3-(2-phenethylamino)-6-methyl-1-carboxymethylpyrazinone and 4-aminomethyl-2-t-butyloxycarbonylamino-3-methylpyridine using the procedure of METHOD 4: MS (FAB) 407 (M+1)$^+$.

EXAMPLE XXXIII

Preparation of 3-[2-(2-Pyridyl)ethylamino]-6-methyl-1-(2-amino-6-methyl-5methylcarboxamidomethylpyridinyl)-pyrainzone

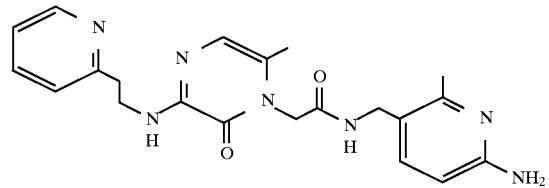

The title compound was prepared as the HCl salt from 3,5-dichloro-6-methyl-1-carboxymethylpyrazinone and 2-(2-pyridylethyl)amine using the procedure of EXAMPLE I, Step D, followed by the procedure of EXAMPLE V, Steps E and F, mp 209.5°–212° C.: MS (FAB) 408 (M+1)$^+$.

EXAMPLE XXXIV

Preparation of 3-(1-Pentylamino)-5-chloro-6-methyl-1-(2-amino-6-methyl-5-methylcarboxamidomethyl pyridinyl)-pyrazinone

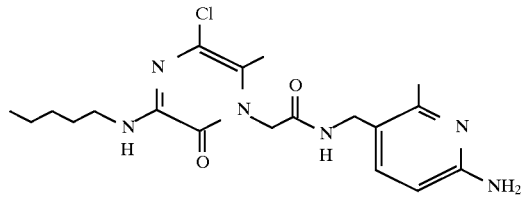

The title compound was prepared from 3,5-dichloro-6-methyl-1-carboxymethylpyrazinone and pentylamine using the procedure of EXAMPLE I, Step D, followed by the procedure of EXAMPLE V, Step F: MS (FAB) 407 (M+1)$^+$.

EXAMPLE XXXV

Preparation of 3-[2-(4-Morpholino)ethylamino]-6-methyl-1-(2-amino-6-methyl-5-methylcarboxamidomethylpyridinyl)-pyrazinone

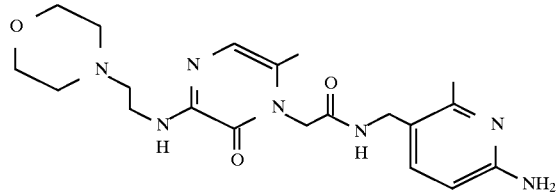

The title compound was prepared as the HCl salt from 3,5-dichloro-6-methyl-1-carboxymethylpyrazinone and 2-(4-morpholinoethyl)amine using the procedure of EXAMPLE I, Step D, followed by the procedure of EXAMPLE V, Step E and the procedure of METHOD 4: Analysis for C20H29N7O3.3.7HCl.3.05 H$_2$O; calc. C 39.69 H 6.46 N 16.20 found C 39.69 H 6.46 N 15.95

EXAMPLE XXXVI

Preparation of 3-[2(S)-Methyl-1-butylamino]-6-methyl-1-(2-amino-6-methyl-5-methylcarboxamidomethylpyridinyl)-pyrazinone

The title compound was prepared from 3,5-dichloro-6-methyl-1-carboxymethylpyrazinone and 2(S)-Methyl-1-butylamine using the procedure of EXAMPLE I, Step D, followed by the procedure of EXAMPLE V, Steps E and F, mp 188.5°–193.5° C.

EXAMPLE XXXVII

Preparation of 3-(1-Pentylamino)-6-methyl-1-(2-amino-6-methyl-5-methycarboxamidomethylpyridinyl)-pyrazinone

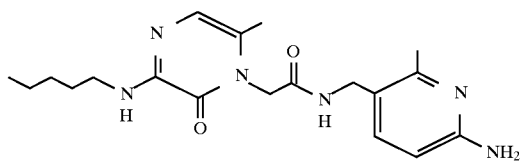

The title compound was prepared from 3,5-dichloro-6-methyl-1-carboxymethylpyrazinone and 1-pentylamine using the procedure of EXAMPLE I, Step D, followed by the procedure of EXAMPLE V, Steps E and F, mp 115°–118° C.

EXAMPLE XXXVIII

Preparation of 3-(2,2-Diphenethylamino)-6-methyl-1-(2-amino-6-methyl-5-methylcarboxamidomethylpyridinyl)-pyrazinone

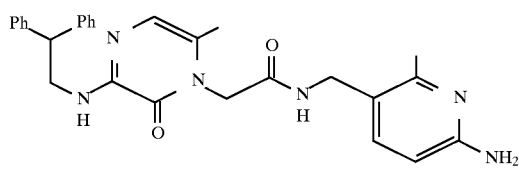

The title compound was prepared as the HCl salt from 3,5-dichloro-6-methyl-1-carboxymethylpyrazinone and 2,2-diphenethylamine using the procedure of EXAMPLE I, Step D, followed by the procedure of EXAMPLE V, Step E and the procedure of METHOD 4: Analysis for C28H30N6O2.2.0HCl.0.50H$_2$O; calc. C 59.56 H 5.89 N 14.89 found C 59.53 H 5.72 N 14.59

EXAMPLE XXXIX

Preparation of 3-Cyclohexylamino-6-methyl-1-(2-amino-6-methyl-5-methylcarboxamidomethylpYridinyl)-pyrazinone

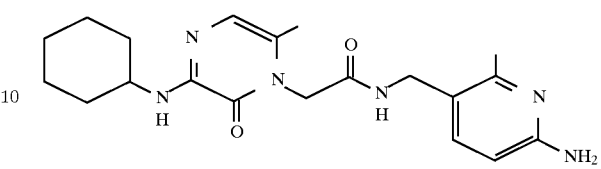

The title compound was prepared as the HCl salt from 3,5-dichloro-6-methyl-1-carboxymethylpyrazinone and cyclohexylamine using the procedure of EXAMPLE I, Step D, followed by the procedure of EXAMPLE V, Step E and the procedure of METHOD 4, mp 221°–227° C.

EXAMPLE XL

Preparation of 3-(2-Indanylamino)-6-methyl-1-(2-amino-6-methyl-5-methylcarboxamidomethylpyridinyl)-pyrazinone

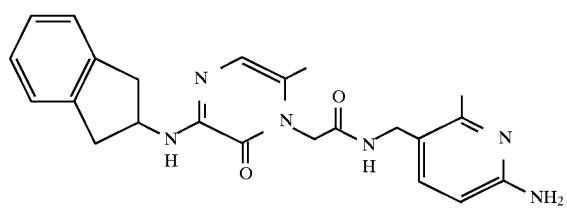

The title compound was prepared as the HCl salt from 3,5-dichloro-6-methyl-1-carboxymethylpyrazinone and 2-aminoindan using the procedure of EXAMPLE I, Step D, followed by the procedure of EXAMPLE V, Step E and the procedure of METHOD 4: Analysis for C23H26N6O2.2.0HCl.1.0H$_2$O.0.35EtOAc; calc. C 54.25 H 6.12 N 15.56 found C 54.20 H 5.85 N 15.54

EXAMPLE XLI

Preparation of 3-[2(R)-Hydroxy-1(S)-indanylamino]-6-methyl-1-(2-amino-6-methyl-5-methylcarboxamidomethylpyridinyl)-pyrazinone

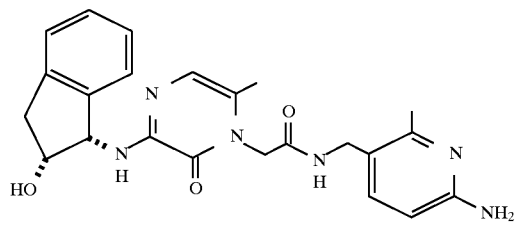

The title compound was prepared from 3,5-dichloro-6-methyl-1-carboxymethylpyrazinone and 2(R)-hydroxy-1(S)-aminoindan using the procedure of EXAMPLE I, Step D, followed by the procedure of EXAMPLE V, Step E and the procedure of METHOD 4, mp 280°–283° C.

EXAMPLE XLII

Preparation of 3-[2-(3,4-Methylenedioxyphenethylamino)]-6-methyl-1-(2-amino-6-methyl-5-methylcarboxamidomethylpyridinyl)-pyrazinone

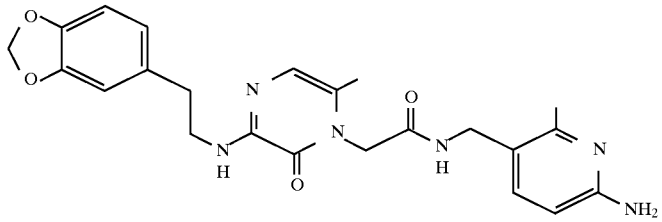

The title compound was prepared as the HCl salt from 3,5-dichloro-6-methyl-1-carboxymethylpyrazinone and 2-(3,4-methylenedioxyphenyl)-ethylamine using the procedure of EXAMPLE I, Step D, followed by the procedure of EXAMPLE V, Step E and the procedure of METHOD 4: Analysis for C23H26N 6O4.3.0HCl.0.30EtOAc; calc. C 49.57 H 5.40 N 14.33 found C 49.94 H 5.25 N 14.48

EXAMPLE XLIII

Preparation of 3-[2-(4-Fluorophenethylamino)]-6-methyl-1-(2-amino-6-methyl-5-methylcarboxamidomethylpyridinyl)-pyrazinone

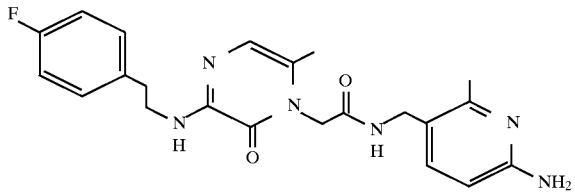

The title compound was prepared as the TFA salt from 3,5-dichloro-6-methyl-1-carboxymethylpyrazinone and 2-(4-fluorophenyl)-ethylamine using the procedure of EXAMPLE I, Step D, followed by the procedure of EXAMPLE V, Step E and the procedure of METHOD 4: MS (FAB) 425 (M+1)$^+$.

EXAMPLE XLIV

Preparation of 3-[2-(4-Pyridyl)-ethylamino]-6-methyl-1-(2-amino-6-methyl-5-methylcarboxarnidomethylpyridinyl)-pyrazinone

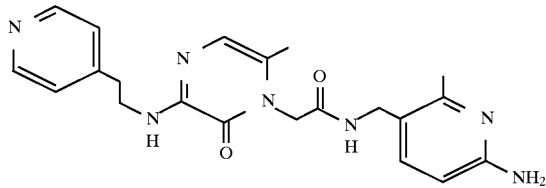

The title compound was prepared as the HCl salt from 3,5-dichloro-6-methyl-1-carboxymethylpyrazinone and 2-(4-pyridyl)-ethylamine using the procedure of EXAMPLE 1, Step D, followed by the procedure of EXAMPLE V, Step E and the procedure of METHOD 4, mp 220°–226° C.: MS (FAB) 408 (M+1)$^+$.

EXAMPLE XLV

Preparation of rac 3-(1-Indanylamino)-6-methyl-1-(2-amino-6-methyl-5-methylcarboxamidomethylpyridinyl)-pyrazinone

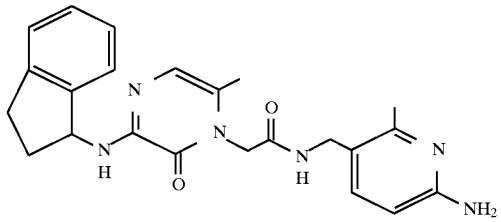

The title compound was prepared as the HCl salt from 3,5-dichloro-6-methyl-1-carboxymethylpyrazinone and rac 1-aminoindan using the procedure of EXAMPLE I, Step D, followed by the procedure of EXAMPLE V, Step E and the procedure of METHOD 4: Analysis for C23H26N6O2.2.0HCl.1.0H$_2$O; calc. C 54.22 H 5.94 N 16.50 found C 54.12 H 5.65 N 16.45

EXAMPLE XLVI

Preparation of rac 3-[2-(2-Tetrahydropyranyl)-ethylamino]-6-methyl-1-(2-amino-6-methyl-5-methylcarboxamidomethylpyridinyl)-pyrazinone

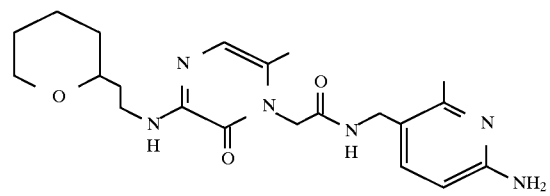

Step A: rac 2-Cyanomethylpyran

A mixture of rac 2-bromomethylpyran (3.0 g, 16 mmol) and sodium cyanide (1.6 g, 33 mmol) in DMF (50 ml) was heated at 100° C. overnight. The solvent was then removed in vacuo and the residue partitioned between methylene chloride and water. The organic phase was dried over sodium sulfate. Removal of the solvent and chromatography of the residue (4:1 hexane /ethyl acetate) gave the title compound:

$^1$H NMR (CDCl$_3$) d 1.35–1.91 (m, 6 H), 2.50 (d, J=6.0 Hz, 2 H), 3.59 (m,2 H),4.01 (m, 1 H).

Step B: rac 2-Aminoethylpyran

A mixture of rac 2-cyanomethylpyran (4.2 g) and 10% Pd/C (4.0 g) in 1:1 ethanol:acetic acid (150 ml) was hydrogenated at 55 psi overnight. The reaction mixture was filtered through Celite and the solvents were then removed in vacuo. The residue was partitioned between chloroform and 10% sodium carbonate solution. The organic phase was dried over sodium sulfate. Removal of the solvent gave the title compound:

$^1$H NMR (CDCl$_3$) d 1.32–1.84 (m, 6 H), 3.06 (m, 2 H), 3.44 (m, 2 H), 3.98 (m, 1 H).

Step C: rac 3-[2-(2-Tetrahydropyranyl)-ethylamino]-6-methyl-1-(2-amino-6-methyl-5-methylcarboxamidomethylpyridinyl)-pyrazinone The title compound was prepared as the TFA salt from 1-benzyloxycarbonylmethyl-3,5-dichloro-6-methylpyrazinone and 2-(2-tetrahydropyranyl)-ethylamine using the procedure of EXAMPLE V, Steps C–E, followed by the procedure of METHOD 4: MS (FAB) 415 (M+1)$^+$.

EXAMPLE XLVII

Preparation of 3-[2-(3-Pyridyl)-ethylamino]-6-methyl-1-(2-amino-6-methyl-5-methylcarboxamidomethylpyridinyl)-pyrazinone

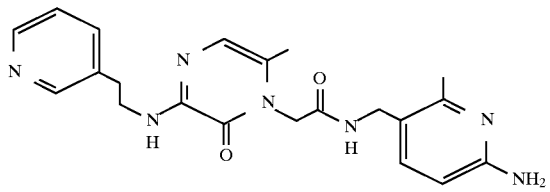

The title compound was prepared as the HCl salt from 3,5-dichloro-6-methyl-1-carboxymethylpyrazinone and 2-(3-pyridyl)-ethylamine using the procedure of EXAMPLE I, Step D, followed by the procedure of EXAMPLE V, Step E and the procedure of METHOD 4, mp >250° C.: MS (FAB) 408 (M+1)$^+$.

EXAMPLE XLVIII

Preparation of 3-[2-(4-Imidazolyl)-ethylamino]-6-methyl-1-(2-amino-6-methyl-5-methylcarboxamidomethylpyridinyl)-pyrazinone

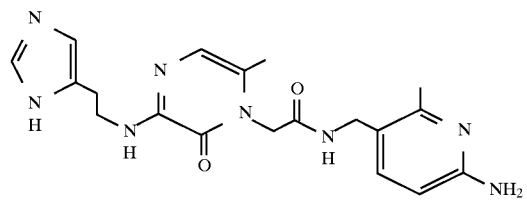

The title compound was prepared as the HCl salt from 1-benzyloxycarbonylmethyl-3,5-dichloro-6-methylpyrazinone and histamine using the procedure of EXAMPLE V, Steps C–E and the procedure of METHOD 4: MS (FAB) 397 (M+1)$^+$.

EXAMPLE IL

Preparation of 3-[2-(3-Indolyl)-ethylamino]-6-methyl-1-(2-amino-6-methyl-5-methylcarboxamidomethylpyridinyl)-pyrazinone

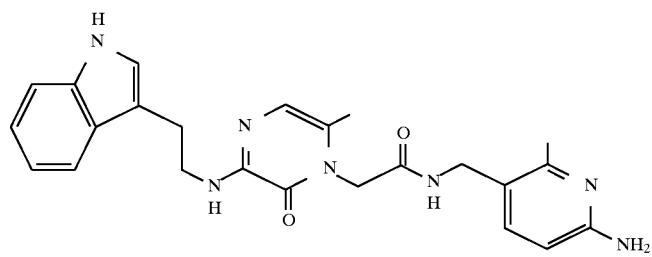

The title compound was prepared from 1benzyloxycarbonylmethyl-3,5-dichloro-6-methylpyrazinone and tryptamine using the procedure of EXAMPLE V, Steps C–E and the procedure of METHOD 4, mp 195°–197° C.: MS (FAB) 446 (M+1)$^+$.

EXAMPLE L

Preparation of 3-{2-[3-(6-Fluoro)-indolyl]-ethylamino}-6-methyl-1-(2-amino-6-methyl-5-methylcarboxamidomethylpyridinyl)-pyrazinone

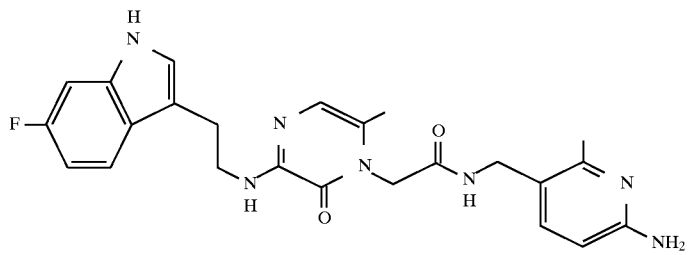
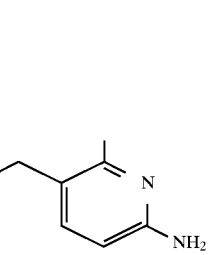

The title compound was prepared as the TFA salt from 1-benzyloxycarbonylmethyl-3,5-dichloro-6-methylpyrazinone and 6-fluorotryptamine using the procedure of EXAMPLE V, Steps C–E and the procedure of METHOD 4: MS (FAB) 464 (M+1)$^+$.

EXAMPLE LI

Preparation of 3-(2-Cyclopentylethylamino)-6-methyl-1-(2-amino-6-methyl-5-methylcarboxamidomethylpyridinyl)-pyrazinone

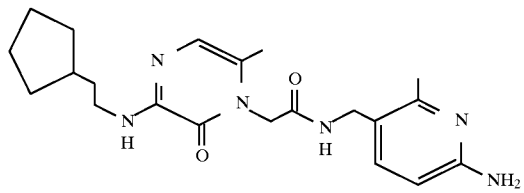

The title compound was prepared as the HCl salt from 1-benzyloxycarbonylmethyl-3,5-dichloro-6-methylpyrazinone and 2-cyclopentylethylamine using the procedure of EXAMPLE V, Steps C–E and the procedure of METHOD 4: MS (FAB) 399 (M+1)$^+$.

EXAMPLE LII

Preparation of 3-[2-(4-methylphenyl)-ethylamino]-6-methyl-1-(2-amino-6-methyl-5-methylcarboxamidomethylpyridinyl)-pyrazinone

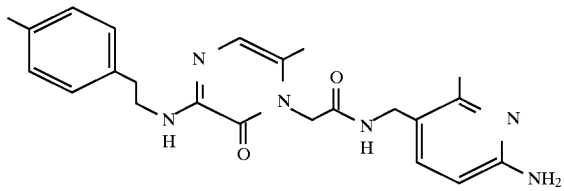

The title compound was prepared from 1-benzyloxycarbonylmethyl-3,5-dichloro-6-methylpyrazinone and 2-(4-methylphenyl)ethylamine using the procedure of EXAMPLE V, Steps C–F, mp 254.5°–260° C.: MS (FAB) 421 (M+1)$^+$.

EXAMPLE LIII

Preparation of 3-[2-(2-thienyl)-ethylamino]-6-methyl-1-(2-amino-6-methyl-5-methylcarboxamidomethylpyridinyl)-pyrazinone

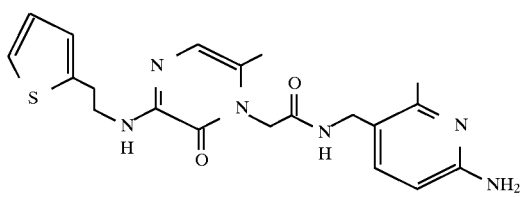

The title compound was prepared from 3,5-dichloro-6-methyl-1-carboxymethylpyrazinone and 2-(2-thienyl)ethylamine using the procedure of EXAMPLE I, Step D, followed by the procedure of EXAMPLE V, Step E and the procedure of METHOD 4, mp 245.5°–249.5° C.: MS (FAB) 413 (M+1)$^+$.

EXAMPLE LIV

Preparation of rac 3-[1-(3-pyridyl)-2-propylamino]-6-methyl-1-(2-amino-6-methyl-5-methylcarboxamidomethylpyridinyl)-pyrazinone

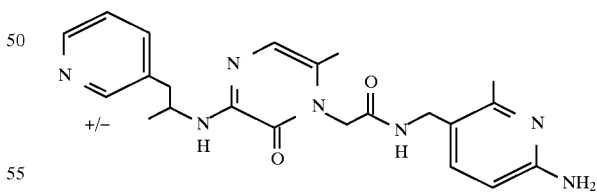

The title compound was prepared as the HCl salt from 1-benzyloxycarbonylmethyl-3,5-dichloro-6-methylpyrazinone and 1-(3-pyridyl)-2-propylamine (which was prepared following the procedure of Burger et al.; J. Org. Chem. 1957, 22, 143) using the procedure of EXAMPLE V, Steps C–E followed by the procedure of METHOD 4: MS (FAB) 422 (M+1)$^+$; Analysis for C22H27N7O2.4.1HCl.1.0 EtOAc; calc. C 47.38 H 5.98 N 14.88 found C 47.37 H 6.11 N 14.88

EXAMPLE LV

Preparation of rac 3-[2-(3-pyridyl)-1-propylamino]-6-methyl-1-(2-amino-6-methyl-5-methylcarboxamidomethylpyridinyl)-pyrazinone

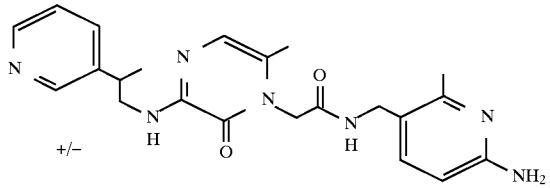

Step A: 2-(3-Pyridyl)-1-nitropropane

To a solution of anhydrous $CeCl_3$ (8.63 g, 35.0 mmol) in 200 mL of anhydrous THF, cooled to 0° C. was added MeMgBr (1.0M in ether, 11.7 mL, 35.0 mmol) dropwise. After stirring for 1.5 h the solution was cooled to −40° C. and a solution of 3-(2-nitroethenyl)pyridine (available from TCI-USA) (1.50 g, 10.0 mmol) in 5 mL of THF was added dropwise over 15 minutes. After 5 min the reaction was quenched with glacial AcOH (1 mL) and concentrated in vacuo. The residue was dissolved in methylene chloride (200 mL) and washed with NaOH (1×50 mL, 1N) and water (1×50 mL), dried over $Na_2SO_4$, filtered and concentrated in vacuo, the residue was purified by flash column chromatography (30×150 mm column of $SiO_2$, EtOAc/$CH_2Cl_2$ (1:3)) to give the title compound as an oil:

$^1$H NMR (400 MHz, $CDCl_3$) d 1.40 (d, J=6.9 Hz, 3H), 3.62–3.71 (m, 1H), 4.53–4.62 (m, 2H), 7.26–7.36 (m, 1H), 7.54–7.59 (m, 1H), 8.48–8.53 (m, 2H).

Step B: 2-(3-Pyridyl)-1-propylamine

To a solution of 2-(3-pyridyl)-1-nitropropane (0.91 g, 5.48 mmol) in 20 mL of ethanol and 0.1 mL of 12N HCl was added 10% Pd/C (1.00 g) under argon. The solution was evacuated and flushed with hydrogen several times, place under an atmosphere of hydrogen and vigorously stirred. After 14 h the mixture was evacuated and flushed with argon several times, filtered through celite and washed with 200 mL of ethanol. The volatiles were removed in vacuo to provide a residue which was partitioned between methylene chloride (100 mL) and NaOH (50 mL, 10%) and the aqueous layer was extracted with methylene chloride (2×100 mL). The combined organic layers were dried over $MgSO_4$, filtered, concentrated in vacuo and the residue was purified by flash column chromatography (20×150 mm column of $SiO_2$, $CH_2Cl_2$/$CH_2Cl_2$ saturated with $NH_3$/MeOH 60:39:1) to give the title compound as an oil:

$^1$H NMR (400 MHz, $CDCl_3$) d 1.28 (d, J=6.8 Hz, 3H), 2.74–2.85 (m, 1H), 2.87–2.92 (m, 2H), 7.23–7.26 (m, 1H), 7.51–7.54 (m, 1H), 8.47–8.49 (m, 2H).

Step C: rac 3-[2-(3-Pyridyl)-1-propylamino]-6-methyl-1-(2-amino-6-methyl-5-methylcarboxamidomethylpyridinyl)-pyrazinone The title compound was prepared from 1-benzyloxycarbonylmethyl-3,5-dichloro-6-methylpyrazinone and 2-(3-pyridyl)-1-propylamine using the procedure of EXAMPLE V, Steps C–F: Analysis for C22H27N7O2.0.1 H$_2$O; calc. C 62.42 H 6.48 N 23.10 found C 62.08 H 6.28 N 23.55

EXAMPLE LVI

Preparation of 3-[2-Methyl-2-(2-pyridyl)-1-propylamino]-6-methyl-1-(2-amino-6-methyl-5-methylcarboxamidomethylpyridinyl)-pyrazinone

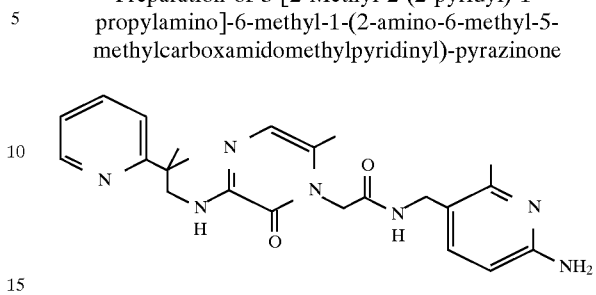

Step A: 2-Methyl-2-(2-pyridyl)-propionitrile

To a solution of 2-pyridylacetonitrile (1.00 g, 8.44 mmol) in anhydrous DMF (20 mL) cooled to 0° C. was added NaH (0.743 g, 18.58 mmol, 60% by wt dispersion in mineral oil) portionwise. After 10 minutes, iodomethane (1.31 mL, 21.11 mmol) was added via syringe over a 15 minute period. After 1 h the reaction was diluted into ethyl acetate (200 mL) and washed with water (5×20 mL) and brine (1×20 mL) and dried over $MgSO_4$. The solution was filtered, the volatiles were removed in vacuo and the oil was purified by flash column chromatography (30×150 mm column of $SiO_2$, EtOAc/Hex gradient elution 1:4 to 1:3) to give the title compound as a colorless oil:

$^1$H NMR (400 MHz, $CDCl_3$) d 1.77 (s, 6H), 7.22–7.27 (m, 1H), 7.59 (dd, J=7.8 and 0.9 Hz, 1H), 7.71–7.75 (m, 1H), 8.59–8.61 (m, 1H).

Step B: 2-Methyl-2-(2-pyridyl)-1-propylamine

To a solution of 2-methyl-2-(2-pyridyl)-propionitrile (1.018 g, 6.97 mmol) in 25 mL of anhydrous diethyl ether under a blanket of Argon was added $LiAlH_4$ (0.538 g, 14.17 mmol) portionwise. After 1 h the reaction was quenched with the addition of water (1 mL), NaOH (1.0 mL, 1N), water (8 mL) then diethyl ether (20 mL) and let stir for 10 h. The solution was filtered through a plug of celite and washed with diethyl ether:MeOH (1:1) (200 mL). The filtrate was concentrated in vacuo and the residue was purified by flash column chromatography (30×150 mm column of $SiO_2$, $CH_2Cl_2$/$CH_2Cl_2$ saturated with $NH_3$/MeOH gradient elution 60:39:1 to 60:38:2 to 60:37:3) to give the title compound as a resin:

$^1$H NMR (400 MHz, $CDCl_3$) d 1.21 (br s, 2H), 1.38 (s, 6H), 2.98 (s, 2H), 7.05–7.14 (m, 1H), 7.34–7.38 (m, 1H), 7.60–7.64 (m, 1H), 8.59–8.61 (m, 1H).

Step C: 3-(2-methyl-2-(2-pyridyl)-1-propylamino)-6-methyl-1-(2-amino-6-methyl-5-methylcarboxamidomethylpyridinyl)-pyrazinone The title compound was prepared as the HCl salt from 1-benzyloxycarbonylmethyl-3,5-dichloro-6-methylpyrazinone and 2-methyl-2-(2-pyridyl)-1-propylamine using the procedure of EXAMPLE V, Steps C–E followed by the procedure of METHOD 4: MS (FAB) 436 (M+1)$^+$; Analysis for C23H29N7O2.3.0 HCl.0.3 EtOAc; calc. C 50.87 H 6.07 N 17.16 found C 50.52 H 5.76 N 16.88

EXAMPLE LVII

Preparation of rac 3-{ 1-[5-(2-Methylaminopyridyl)]-2-propylamino}-6-methyl-1-(2-amino-6-methyl-5-methylcarboxamidomethylpyridinyl)-pyrazinone

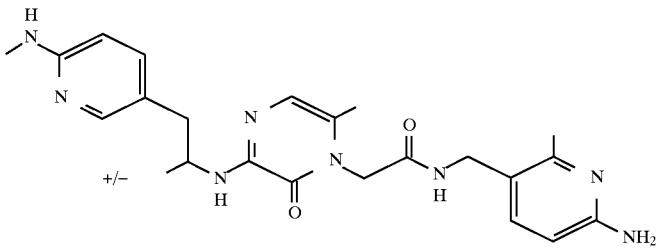

Step A: Methyl-6-(t-butoxycarbonylamino)-nicotinate

To a solution of 6-aminonicotinic acid (2.00 g, 14.48 mmol) dissolved in chloroform/MeOH (90 mL: 30 mL) was added (trimethylsilyl)diazomethane (2.0M in hexanes, 25 mL). After 15 minutes acetic acid (0.1 mL) was added and the solution was concentrated in vacuo to a residue. Trituration with EtOAc/Hex (2:1) provided methyl-6-aminonicotinate as a pale yellow solid after filtration. This material was used directly in the next step. To a solution of methyl-6-aminonicotinate (1.86 g, 12.22 mmol) dissolved in methylene chloride (90 mL) was added di-t-butyl dicarbonate (2.69 g, 12.34 mmol), 4-dimethylaminopyridine (0.15 g, 1.22 mmol) and triethylamine (2.00 mL, 14.66 mmol). After 14 h the reaction was diluted with EtOAc (400 mL) and washed with citric acid (1×50 mL, 10%), water (1×50 mL) and brine (1×50 mL) and was dried over $MgSO_4$, filtered, and concentrated in vacuo. The residue was purified by flash column chromatography (40×150 mm column of $SiO_2$, EtOAc/Hex gradient elution 1:6, 1:5, 1:3) to to give the title compound as a white solid:

$^1$H NMR (400 MHz, $CDCl_3$) d 1.56 (s, 9H), 3.91 (s, 3H), 8.06 (d, J=8.2 Hz, 1H), 8.24–8.27 (m, 1H), 8.57 (br s, 1H), 8.93 (dd, J=0.7 and 2.4 Hz, 1H).

Step B: 2-(t-Butoxycarbonylamino)-5-pyridinecarboxaldehyde

To a solution of methyl-6-(tert-butoxycarbonylamino)-nicotinate (2.20 g, 8.72 mmol) in anhydrous THF (50 mL), cooled to −30° C. was added DIBAL-H (1.0M in hexane, 34.8 mL, 34.8 mmol) dropwise. After 1 h, 40 mL of a saturated solution of Rochelle salts was added and stirred vigorously for 10 h. The volatiles were removed in vacuo and the aqueous layer was extracted with methylene chloride (3×50 mL). The organic layer was washed with water (1×50 mL) and brine (1×50 mL), dried over $MgSO_4$, filtered, and concentrated in vacuo. The residue was used directly in the next step. To a solution of oxalyl chloride (4.12 g, 32.46 mmol) in methylene chloride (30 mL), cooled to −78° C., was added DMSO (2.54 g, 32.46 mmol) dissolved in methylene chloride (9 mL) dropwise. After 20 minutes, the crude alcohol (1.82 g, 8.11 mmol) dissolved in 35 mL of methylene chloride was added followed by triethylamine (4.92 g, 48.66 mmoL). The ice bath was removed and the reaction stirred for 1 hr at rt, then water (30 mL) was added. The layers were separated and the aqueous layer was extracted with methylene chloride (2×50 mL). The organic layer was washed with water (1×50 mL) and brine (1×50 mL), dried over $MgSO_4$, filtered, and concentrated in vacuo. The residue was purified by flash column chromatography (30×150 mm column of $SiO_2$, EtOAc/methylene chloride 1:11) to give the title compound as a colorless solid:

$^1$H NMR (400 MHz, $CDCl_3$) d 1.55 (s, 9H), 7.79 (br s, 1H), 8.13–8.14 (m, 2H), 8.71 (dd, J=1.1 and 1.8 Hz, 1H), 9.96 (s, 1H).

Step C: 2-(t-Butoxycarbonylamino)-5-[1-(2-nitropropenyl)]-pyridine

To a solution of 2-(t-butoxycarbonylamino)-5-pyridinecarboxaldehyde (1.20 g, 5.40 mmol) dissolved in N-methylmorpholine (40 mL) was added nitroethane (2.20 g, 27.0 mmol), potassium fluoride (0.144 g, 2.49 mmol), and 18-crown-6 (0.036 g). Acetic anhydride (2.20 g, 21.6 mmol) and a catalytic amount of 4-dimethylaminopyridine (0.05 g) was added after 1 hr. The reaction was quenched after 12 h by pouring into 200 mL of ice. The aqueous layer was extracted with methylene chloride (3×75 mL) and the combined organic layer was washed with water (2×50 mL) and brine (1×50 mL), dried over $MgSO_4$, filtered, and concentrated in vacuo. The residue was triturated with methylene chloride and the solid was collected by filtration to give the title compound as a pale yellow solid:

$^1$H NMR (400 MHz, $CDCl_3$) d 1.54 (s, 9H), 2.47 (d, J=0.9 Hz, 3H), 7.41 (br s, 1H), 7.76 (dd, J=2.3 and 8.8 Hz, 1H), 8.04 (s, 1H), 8.05 (d, J=8.8 Hz, 1H), 8.33 (d, J=2.4 Hz, 1H).

Step D: rac 1-[5-(2-Methylaminopyridyl)]-2-propylamine

To a solution of 2-(t-butoxycarbonylamino)-5-[1-(2-nitropropenyl)]-pyridine (0.20 g, 0.716 mmol) dissolved in THF (8 mL), cooled to 0° C., was added borane THF complex (4.30 mL, 1.0M in THF, 4.30 mmol). The ice bath was removed and $NaBH_4$ (0.0135 g, 0.358 mmol) was added and the reaction was warmed to 65° C. After 24 h the reaction was poured into ice (50 mL), acidified to pH 2 with 3N HCl and warmed to 65° C. for 2 h. The pH was adjusted to 8 with aqueous NaOH (1N) and the solvent was removed in vacuo. The aqueous layer was extracted with methylene chloride (3×75 mL) and the combined organic layers were washed with water (2×50 mL) and brine (1×50 mL), dried over $MgSO_4$, filtered and concentrated in vacuo. The residue was purified by flash column chromatography (15×150 mm column of $SiO_2$, $CH_2Cl_2/CH_2Cl_2$ saturated with $NH_3$/MeOH 60:37:3) to give the title compound an oil:

$^1$H NMR (400 MHz, $CDCl_3$) d 1.09 (d, J=6.2 Hz, 3H), 2.37–2.42 (m, 1H), 2.54 (dd, J=5.5 and 13.7 Hz, 1H), 2.90 (d, J=4.9 Hz, 3H), 3.03–3.09 (m, 1H), 4.62 (br s, 1H), 6.34–6.37 (m, 1H), 7.26–7.33 (m, 1H), 7.89–7.92 (m, 1H).

Step E: rac 3-{1-[5-(2-Methylaminopyridyl)]-2-propylamino}-6-methyl-1-(2-amino-6-methyl-5-methylcarboxamidomethylpyridinyl)-pyrazinone The title compound was prepared as the HCl salt from 1-benzyloxycarbonylmethyl-3,5-dichloro-6-methylpyrazinone and rac 1-[5-(2-methylaminopyridyl)]-2- propylamine using the procedure of EXAMPLE V, Steps C–F: MS (FAB) 451 (M+1)+; Analysis for C23H30N8O2.2.45 HCl.1.25 CH2Cl2; calc. C 45.08 H 5.45 N 17.35 found C 45.03 H 5.48 N 17.37.

EXAMPLE LVIII

Preparation of 3-(2-Methyl-2-phenyl-1-propylamino)-6-methyl-1-(2-amino-6-methyl-5-methylcarboxamidomethylpyridinyl)-pyrazinone

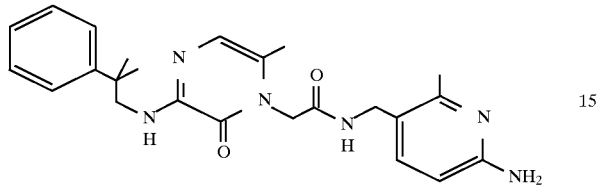

The title compound was prepared from 1-benzyloxycarbonylmethyl-3,5-dichloro-6-methylpyrazinone and 2-methyl-2-phenyl-1-propylamine using the procedure of EXAMPLE V, Steps C–F, mp 179°–181° C.: MS (FAB) 435 (M+1)+.

EXAMPLE LIX

Preparation of 3-[2-Methyl-2-(3,4-methylenedioxyphenyl)-1-propylamino]-6-methyl-1-(2-amino-6-methyl-5-methylcarboxamidomethylpyridinyl)-pyrazinone

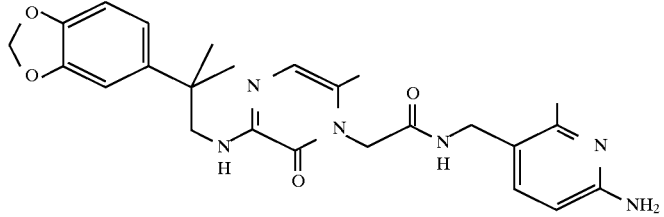

The title compound was prepared as the HCl salt from 1-benzyloxycarbonylmethyl-3,5-dichloro-6-methylpyrazinone and 2-methyl-2-(3,4-methylenedioxyphenyl)-1-propylamine (which was prepared from 3,4-methylenedioxyphenylacetonitrile using the procedure of EXAMPLE LVI, Steps A and B) using the procedure of EXAMPLE V, Steps C–F: MS (FAB) 479 (M+1)+; Analysis for C25H30N6O4.2.10 HCl.0.7 H2O; calc. C 52.88 H 5.95 N 14.80 found C 52.88 H 5.96 N 14.51.

EXAMPLE LX

Preparation of rac 3-[1-(3,4-methylenedioxyphenyl)-2-propylamino]-6-methyl-1-(2-amino-6-methyl-5-methylcarboxamidomethylpyridinyl)-pyrazinone

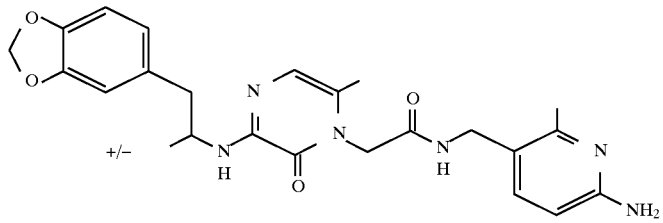

Step A: rac 1-(3,4-methylenedioxyphenyl)-2-propylamine

To a solution of 1-(3,4-methylene dioxyphenyl)-2-nitropropene (0.938 g, 4.53 mmol) dissolved in absolute ethanol (40 mL), methanol (8 mL), and HCl (4N, 4 mL) under an atmosphere of argon was added Pd/C (10%, 0.902 g). The mixture was place under a hydrogen atmosphere (balloon, 1 atm) and stirred for 14 h. The reaction was filtered through celite, washing with ethanol (200 mL), and concentrated in vacuo to give the title compound as a pale brown solid:

$^1$H NMR (400 MHz, CDCl$_3$) d 1.35 (d, J=6.6 Hz, 3H), 2.76 (dd, J=8.6 and 13.5 Hz, 1H), 3.09 (dd, J=5.9 and 13.5 Hz, 1H), 3.41–3.49 (m, 1H), 5.94 (s, 2H), 6.27–6.77 (m, 3H).

Step B: rac 3-[1-(3,4-methylenedioxyphenyl)-2-propylamino]-6-methyl-1-(2-amino-6-methyl-5-methylcarboxamidomethylpyridinyl)-pyrazinone The title compound was prepared as the HCl salt from 1-benzyloxycarbonylmethyl-3,5-dichloro-6-methylpyrazinone 1-(3,4-methylenedioxyphenyl)-2-propylamine using the procedure of EXAMPLE V, Steps C–E followed by the precedure of METHOD 4: MS (FAB) 465 (M+1)$^+$; Analysis for C24H28N6O4.2.40 HCl.0.65 EtOAc; calc. C 52.43 H 5.89 N 13.79 found C 52.39 H 5.57 N 13.82.

EXAMPLE LXI

Preparation of 3-[2-(4-Sulfonamidophenyl) ethylamino]-6-methyl-1-(2-amino-6-methyl-5-methylcarboxamidomethylpyridinyl)-pyrazinone

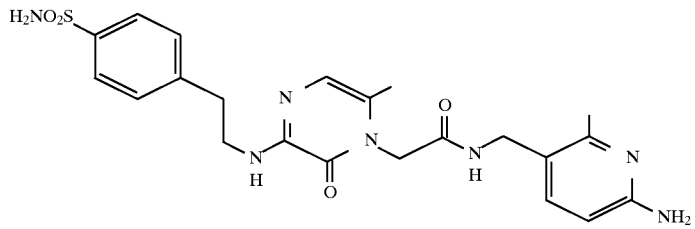

The title compound was prepared as the HCl salt from 1-benzyloxycarbonylmethyl-3,5-dichloro-6-methylpyrazinone and 4-(2-aminoethyl) benzenesulfonamide using the procedure of EXAMPLE V, Steps C–E followed by the procedure of METHOD 4, mp 214°–221° C.: MS (FAB) 486 (M+1)$^+$.

EXAMPLE LXII

Preparation of 3-[2-(3,4-Difluorophenyl) ethylamino]-6-methyl-1-(2-amino-6-methyl-5-methylcarboxamidomethylpyridinyl)-pyrazinone

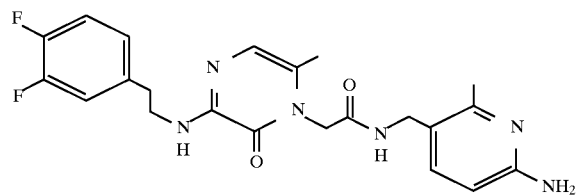

The title compound was prepared as the HCl salt from 1-benzyloxycarbonylmethyl-3,5-dichloro-6-methylpyrazinone and 2-(3,4-difluorophenyl)ethylamine using the procedure of EXAMPLE V, Steps C–E followed by the procedure of METHOD 4, mp>235° C., MS (FAB) 443 (M+1)$^+$.

EXAMPLE LXIII

Preparation of 3-(3,4-Methylenedioxybenzylamino)-6-methyl-1-(2-amino-6-methyl-5-methylcarboxamidomethylpyridinyl)-pyrazinone

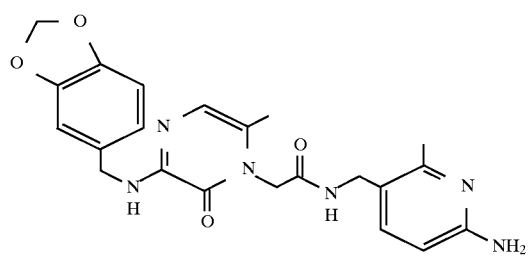

The title compound was prepared as the HCl salt from 1-benzyloxycarbonylmethyl-3,5-dichloro-6-methylpyrazinone and 3,4-methylenedioxybenzylamine using the procedure of EXAMPLE V, Steps C–E followed by the procedure of METHOD 4, mp>255° C.: MS (FAB) 437 (M+1)$^+$.

EXAMPLE LXIV

Preparation of 3-(1-Phenyl-1-cyclobutanemethylamino)-6-methyl-1-(2-amino-6-methyl-5-methylcarboxamidomethylpyridinyl)-pyrazinone

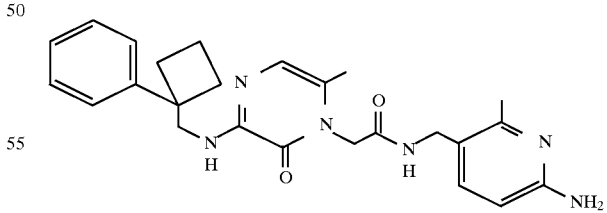

The title compound was prepared as the HCl salt 1-benzyloxycarbonylmethyl-3,5-dichloro-6-methylpyrazinone and 1-phenyl-1-cyclobutanemethylamine (which was prepared from 1-phenyl-1-cyclobutanecarbonitrile using the procedure of EXAMPLE LVI, Step B) using the procedure of EXAMPLE V, Steps C–E followed by the procedure of METHOD 4, mp 252°–259° C.: MS (FAB) 447 (M+1)$^+$.

EXAMPLE LXV

Preparation of 3-(1-Phenyl-1-cyclopropanemethylamino)-6-methyl-1-(2-amino-6-methyl-5-methylcarboxamidomethylpyridinyl)-pyrazinone

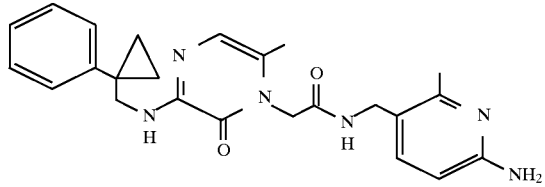

The title compound was prepared from 1-benzyloxycarbonylmethyl-3,5-dichloro-6-methylpyrazinone and 1-phenyl-1-cyclopropanemethylamine (which was prepared from 1-phenyl-1-cyclopropanecarbonitrile using the procedure of EXAMPLE LVI, Step B) using the procedure of EXAMPLE V, Steps C–E followed by the procedure of METHOD 4: MS (FAB) 433 (M+1)$^+$.

EXAMPLE LXVI

Preparation of 3-[2-(2,5-Difluorophenyl) ethylamino]-6-methyl-1-(2-amino-6-methyl-5-methylcarboxamidomethylpyridinyl)-pyrazinone

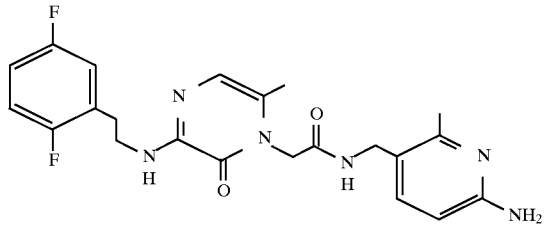

The title compound was prepared as the TFA salt from 1-benzyloxycarbonylmethyl-3,5-dichloro-6-methylpyrazinone and 2-(2,5-difluorophenyl)ethylamine using the procedure of EXAMPLE V, Steps C–F: MS (FAB) 443 (M+1)$^+$.

EXAMPLE LXVII 3-[2-(2-Pyridyl)ethylamino]-5-chloro-6-Methyl-1-[Ethyl-(2-Methylcarboxamidomethyl-4-Chlorophenoxy)-Acetamido]-2-Pyrazinone

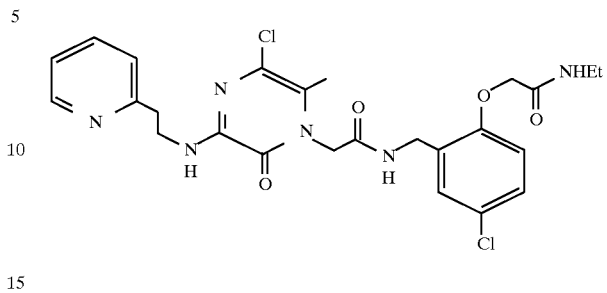

The title compound was prepared from 3,5-dichloro-6-methyl-1-[ethyl-(2-methyl-carboxamidomethyl-4-chlorophenoxy)-acetamido]-pyrazinone [which was prepared using the procedure of EXAMPLE III, Step A, from 3,5-dichloro-6-methyl-1-carboxymethylpyrazinone and ethyl-2-aminomethyl-4-chlorophenoxy)-acetamide)] and 2-(2-pyridyl)ethylamine using the procedure of EXAMPLE III, Step B, MP 207°–209° C.

EXAMPLE LXVIII

3-[2-(2-Pyridyl)ethylarnino]-6-Methyl-1-[Ethyl-(2-Methylcarboxamidomethyl-4-Chlorophenoxy)-Acetamido]-2-Pyrazinone

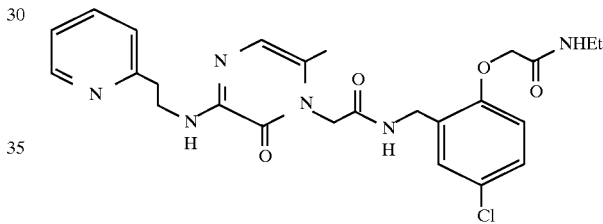

The title compound was prepared from 3-[2-(2-pyridyl) ethylamino]-6-methyl-1-carboxymethylpyrazinone and ethyl-2-aminomethyl-4-chlorophenoxy)-acetamide using the procedure of EXAMPLE V, Step F, MP 195°–197° C.

EXAMPLE LXIX

3-[2-(4-Morpholino)ethylamino]-6-Methyl-1-[cyclopropyl-(2-Methylcarboxamidomethyl-4-Chlorophenoxy)-Acetamido]-2-Pyrazinone

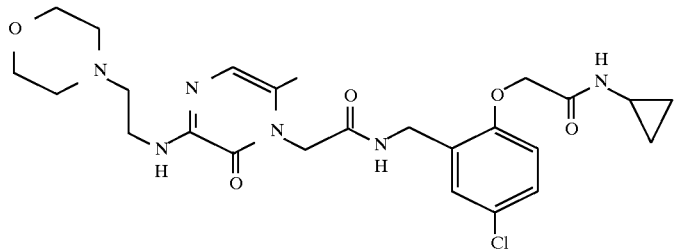

The title compound was prepared from 3-[2-(4-morpholino)ethylaminol-6-methyl-1-carboxymethylpyrazinone and cyclopropyl-2-aminomethyl-4-chlorophenoxy)-acetamide using the procedure of EXAMPLE V, Step F: Analysis for C25H33N6O5Cl.0.45 H2O; calc. C 55.49 H 6.31 N 15.53 found C 55.14 H 6.16 N 16.13

EXAMPLE LXX

3-[2-(2-Pyridyl)ethylamino]-6-Methyl-1-[cyclopropyl-(2-Methylcarboxamidomethyl-4-Chlorophenoxy)-Acetamido]-2-Pyrazinone

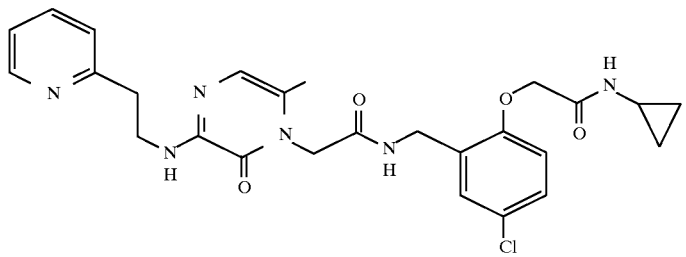

The title compound was prepared from 3-[2-(2-pyridyl)ethylamino]-6-methyl-1-carboxymethylpyrazinone and cyclopropyl-2-aminomethyl-4-chlorophenoxy)-acetamide using the procedure of EXAMPLE V, Step F, mp 196°–199° C.: MS (FAB) 525 (M+1)$^+$.

EXAMPLE LXXI

3-[2(S)-Methyl-1-butylamino]-6-Methyl-1-[cyclopropyl-(2-Methylcarboxamidomethyl-4-Chlorophenoxy)-Acetamido]-2-Pyrazinone

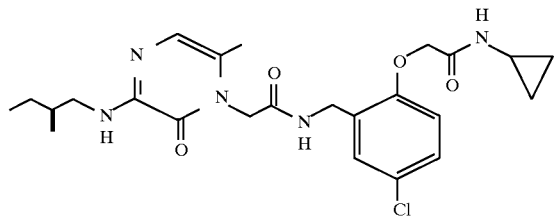

The title compound was prepared from 3-[2(S)-methyl-1-butylamino]-6-methyl-1-carboxymethylpyrazinone and cyclopropyl-2-aminomethyl-4-chlorophenoxy)-acetamide using the procedure of EXAMPLE V, Step F, mp 195°–198° C.: MS (FAB) 490 (M+1)$^+$.

EXAMPLE LXXII 3-(1-Pentylamino)-6-Methyl-1-[ethyl-(2-Methylcarboxamidomethyl-4-Chlorophenoxy)-Acetamido]-2-Pyrazinone

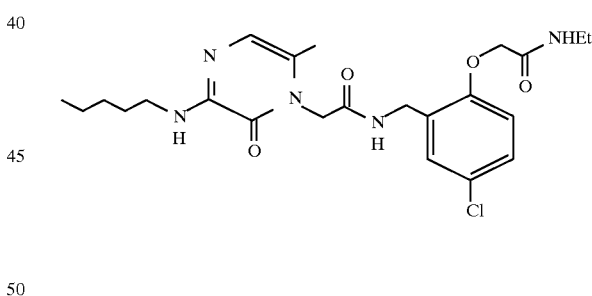

The title compound was prepared from 3-(1-pentylamino)-6-methyl-1-carboxymethylpyrazinone and ethyl-2-aminomethyl-4-chlorophenoxy)-acetamide using the procedure of EXAMPLE V, Step F, mp 125°–127° C.:

EXAMPLE LXXIII
3-(2,2-Diphenethylamino)-6-Methyl-1-[Cyclopropyl-(2-Methylcarboxamidomethyl-4-Chlorophenoxy)-Acetamido]-2-Pyrazinone

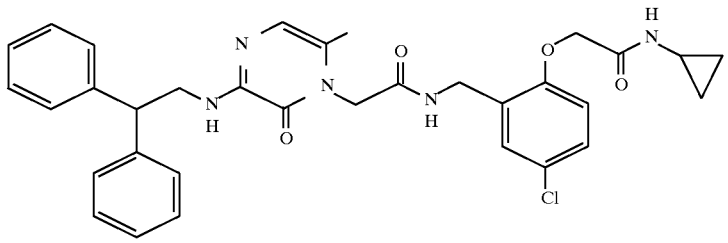

The title compound was prepared from 3-(1-pentylamino)-6-methyl-1-carboxymethylpyrazinone and cyclopropyl-2-aminomethyl-4-chlorophenoxy)-acetamide using the procedure of EXAMPLE V, Step F mp 153°–159° C.: MS (FAB) 600 (M+1)+.

EXAMPLE LXXIV
3-(Cyclohexylamino)-6-Methyl-1-[Cyclopropyl-(2-Methylcarboxamidomethyl-4-Chlorophenoxy)-Acetamido]-2-Pyrazinone

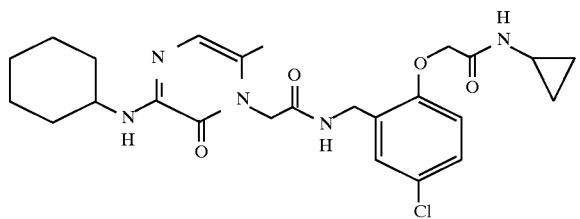

The title compound was prepared from 3-(cyclohexylamino)-6-methyl-1-carboxymethylpyrazinone and cyclopropyl-2-aminomethyl-4-chlorophenoxy)-acetamide using the procedure of EXAMPLE V, Step F, mp 114°–121° C.: MS (FAB) 502 (M+1)+.

EXAMPLE LXXV
3-[2-(2-Pyridyl)ethylamino]-6-Methyl-1-(2,5-Dichlorobenzyl-acetamido)-2-Pyrazinone

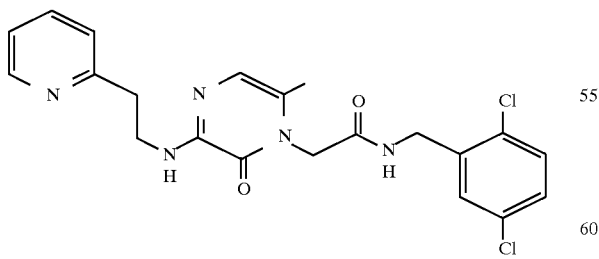

The title compound was prepared from 3-[2-(2-pyridyl)ethylamino]-6-methyl-1-carboxymethylpyrazinone and 2,5-dichlorobenzylamine using the procedure of EXAMPLE V, Step F, mp 188°–191° C.: MS (FAB) 446 (M+1)+.

EXAMPLE LXXVI
3-[2-(2-Pyridyl)ethylamino]-6-Methyl-1-(3-chlorobenzylacetamido)-2-Pyrazinone

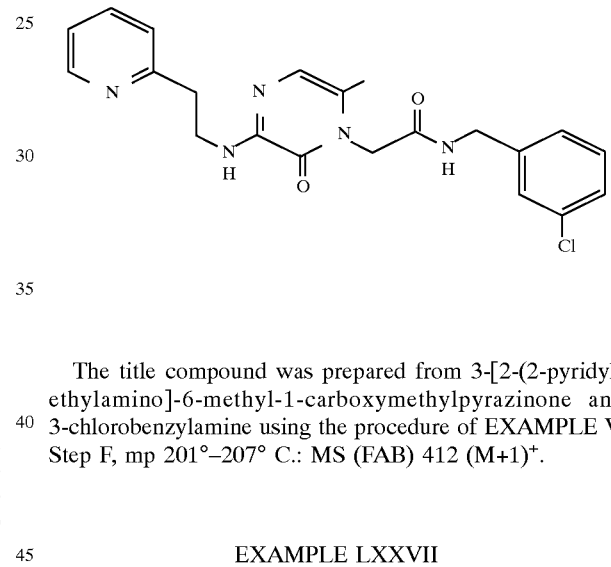

The title compound was prepared from 3-[2-(2-pyridyl)ethylamino]-6-methyl-1-carboxymethylpyrazinone and 3-chlorobenzylamine using the procedure of EXAMPLE V, Step F, mp 201°–207° C.: MS (FAB) 412 (M+1)+.

EXAMPLE LXXVII
3-[2-(2-Pyridyl)ethylaamino]-6-Methyl-1-(3-chloro-6-(cyanomethoxy)benzylacetamido)-2-Pyrazinone

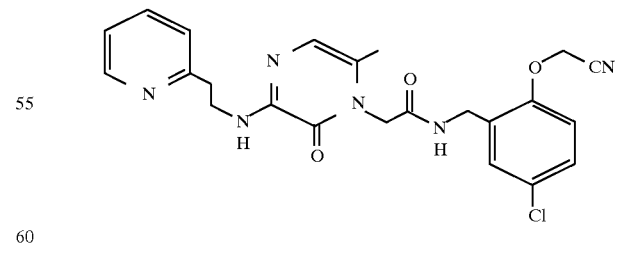

The title compound was prepared from 3-[2-(2-pyridyl)ethylamino]-6-methyl-1-carboxymethylpyrazinone and 3-chloro-6-(cyanomethoxy)benzylamine using the procedure of EXAMPLE V, Step F, mp 207°–211° C.

EXAMPLE LXXVIII

3-[2-(2-Pyridyl)ethyl amino]-6-Methyl-1-(2-fluoro-5-(trifluoromethyl)benzylacetamido)-2-Pyrazinone

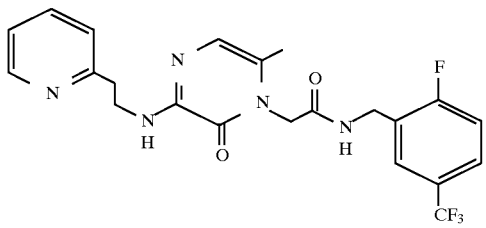

The title compound was prepared from 3-[2-(2-pyridyl)ethylamino]-6-methyl-1-carboxymethylpyrazinone and 2-fluoro-5-trifluoromethyl)benzylamine using the procedure of EXAMPLE V, Step F, mp 181°–184° C.

EXAMPLE LXXIX

3-[2-(4-Pyridyl)ethylamino]-6-Methyl-1-[Cyclopropyl-(2-Methylcarboxamidomethyl-4-Chlorophenoxy)-Acetamido]-2-Pyrazinone

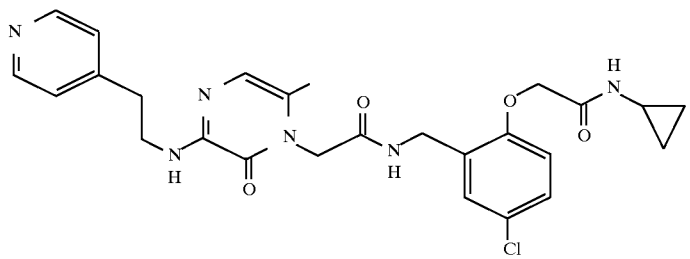

The title compound was prepared from 3-[2-(4-pyridyl)ethylamino]-6-methyl-1-carboxymethylpyrazinone and cyclopropyl-2-aminomethyl-4-chlorophenoxy)-acetamide using the procedure of EXAMPLE V, Step F, mp 190°–192.5° C.: MS (FAB) 525 (M+1)$^+$.

EXAMPLE LXXX

3-[2-(3,4-Methylenedioxyphenyl)ethylamino]-6-Methyl-1-[Cyclo-propyl-(2-Methylcarboxamidomethyl-4-Chlorophenoxy)-Acetamido]-2-Pyrazinone

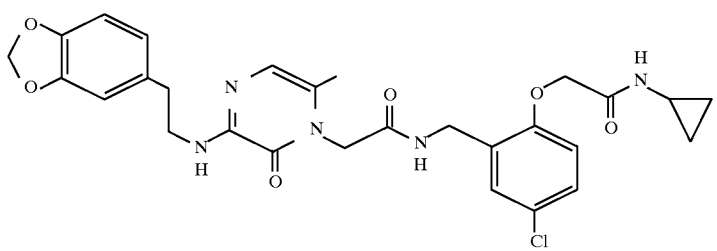

The title compound was prepared from 3-[2-(3,4-methylenedioxyphenyl)ethylamino]-6-methyl-1-carboxymethylpyrazinone and cyclopropyl-2-aminomethyl-4-chlorophenoxy)-acetamide using the procedure of EXAMPLE V, Step F, mp 202°–204° C.: MS (FAB) 568 (M+1)$^+$.

EXAMPLE LXXXI 3-(2-Phenethylamino)-6-Methyl-1-[3-Chloro-6-(Carboxymethoxy)benzylacetamido]-2-Pyrazinone

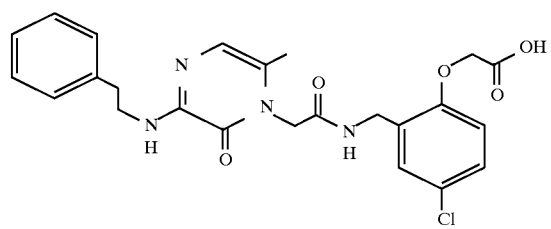

The title compound was prepared from 3-(2-phenethylamino)-6-methyl-1-carboxymethylpyrazinone and ethyl-2-aminomethyl-4-chlorophenoxyacetate using the procedure of EXAMPLE V, Step F, followed by a hydrolysis using the procedure of EXAMPLE V, Step D: MS (FAB) 485 (M+1)$^+$.

EXAMPLE LXXXII

Preparation of 3-(2-Phenylethylamino)-6-methyl-1-(2-amino-6-methyl-5-methylenecarboxamidomethylpyridinyl)-2-pyridinone

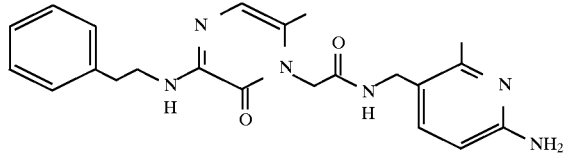

Step A: α-(Allylamino)-propionitrile hydrochloride

Concentrated HCl (20 ml, 0.24 mol)) was added to a stirred solution of allylamine (36 ml, 0.48 mol) in water (100 ml) and ethanol (60 ml) at 0° C. Potassium cyanide (15 g, 0.23 mol) and acetaldehyde (11.2 ml, 0.20 mol) were then added and the mixture was heated to reflux. After 15 h the volatiles were removed in vacuo and the residual solution was saturated with NaCl and was extracted with methylene chloride (3 times). The combined extracts were dried ($Na_2SO_4$) and evaporated in vacuo to an oil which was dissolved in 1M HCl (200 ml). The solution was evaporated in vacuo, azeotroping with 1:1 toluene/methanol to give a solid which was heated to reflux in ethyl acetate (200 ml), cooled, filtered and dried to give the title compound as the HCl salt:

$^1$H NMR (400 MHz, $CD_3OD$) d 1.72 (d, J=7.0 Hz, 3H, $CH_3$), 3.78–3.90 (m, 2H, $CH_2$), 4.63 (q, J=7.0 Hz, a-CH), 5.56–5.66 (m, 2H, CH$CH_2$), 5.91–6.02 (m, 1H, C$H$$CH_2$).

Step B: 1-Allyl-3,5-dichloro-6-methylpyrazinone

A stirred mixture of oxalyl chloride (30.5 ml, 0.35 mol) and α-(allylamino)-propionitrile hydrochloride (10.26 g, 70 mmol) in o-dichlorobenzene (100 ml) was heated to 100° C. for 15 h. The solvent was evaporated in vacuo and the residual black oil was purified by flash column chromatography on silica (eluting with 30% ethyl acetate hexanes) to give the title compound as a tan crystalline solid:

$^1$H NMR (400 Mz, $CDCl_3$) d 2.48 (s, 3H, $CH_3$), 4.75 (m, 2H, $NCH_2$), 5.18 (m, 1H, CHC$H_A$$H_B$), 5.33 (m, 1H, CHC$H_A$$H_B$), 5.85–5.92 (m, 1H, C$H$$CH_A$$H_B$).

Step C: 3,5-Dichloro-6-methyl-1-methylenecarboxypyrazinone

Ruthenium trichloride hydrate (114 mg, 0.547 mmol) was added to a stirred mixture of 1-allyl-3,5-dichloro-6-methylpyrazinone (5.45 g, 24.88 mmol) and sodium periodate (21.82 g, 0.102 mol) in water (75 ml), acetonitrile (50 ml) and carbon tetrachloride (50 ml). After 3 h the reaction mixture was extracted with methylene chloride (4 times) and the combined extracts were dried ($Na_2SO_4$) and evaporated in vacuo to a syrup. The 1H NMR ($CDCl_3$) of this material showed it to be a 1:1 mixture of the acid and the aldehyde. The crude mixture was dissolved in acetone (50 ml) and Jones Reagent (2.7M) was added until the reaction remained orange. The reaction was then extracted into ethyl acetate which was then washed with brine, dried ($Na_2SO_4$) and evaporated in vacuo to give the title compound as a tan solid:

$^1$H NMR (400 Mz, DMSO) d 2.41 (s, 3H, Me), 4.86 (s, 2H, $CH_2$).

Step D: 3-(2-Phenethylamino)-5-chloro-6-methyl-1-methylene-carboxypyrazinone

Phenethylamine (0.80 ml, 6.33 mmol) was added to a stirred solution of 3,5-dichloro-6-methyl-1-methylenecarboxypyrazinone (0.50 g, 2.11 mmol) in dioxane (6 ml) and the resulting solution was warmed to 60° C. After 16 h the reaction mixture was partitioned between methylene chloride and 10% citric acid solution. The organic layer was dried ($Na_2SO_4$) and evaporated in vacuo to give a tan solid which was purified by flash column chromatography (eluting with a methanol/chloroform/2% acetic acid gradient, 2–5% methanol) to give after azeotroping dry with toluene the title compound as a white solid:

$^1$H NMR (300 Mz, DMSO) d 2.19 (s, 3H, Me), 2.84 (t, J=7.0 Hz, 2H, Ph$CH_2$), 3.45 (q, J=7.0 Hz, 2H, C$H_2$NH), 4.70 (s, 2H, $CH_2$$CO_2$), 7.18–7.31 (m, 5H, Ph), 7.46 (br t, 1H, NH).

Step E: 3-(2-Phenethylamino)-6-methyl-1-methylene-carboxypyrazinone

Raney nickel alloy (1 g) was added to a stirred solution of 3-(2-phenethylamino)-5-chloro-6-methyl-1-methylenecarboxypyrazinone (158 mg, 0.49 mmol) in 1:1 methanol/1M NaOH (24 ml). After 2 h the reaction mixture was filtered through celite, washing with 1:1 methanol/water and the filtrate was evaporated in vacuo to a white solid. This crude product, which was contaminated by inorganic salts, was purified by preparative HPLC (C18, water/acetonitrile/0.1% TFA gradient) to give the title compound as a foam:

$^1$H NMR (400 Mz, DMSO) d 2.11 (s, 3H, Me), 2.87 (t, J=7.6 Hz, 2H, Ph$CH_2$), 3.53 (br s, 2H, C$H_2$NH), 4.68 (s, 2H, $CH_2$$CO_2$), 6.68 (s, 1H, pyrazinone H-5), 7.20–7.31 (m, 5H, Ph), 8.16 (br s, 1H, NH).

Step F: 3-(2-Phenethylamino)-6-methyl-1-(2-t-butoxycarbonyl-amino-6-methyl-5-methylenecarboxamidomethyl-pyridinyl)-pyrazinone EDC Hydrochloride (56 mg, 0.29 mmol) was added to a stirred mixture of 3-(2-phenethylamino)-6-methyl-1-methylene-carboxypyrazinone (91 mg, 0.23 mmol), HOBT (40 mg, 0.29 mmol), 5-aminomethyl-2-t-butoxycarbonylamino-6-methylpyridine (70 mg, 0.29 mmol) and N-methylmorpholine (0.13 ml, 1.17 mmol) in DMF (1 ml) and the mixture was stirred for 16 h. The reaction was diluted with ethyl acetate and was washed with water, dried ($Na_2SO_4$) and evaporated in vacuo. The crude product was purified by flash column chromatography on silica (ethylacetate/hexanes gradient, 80–100% ethyl acetate), to give the title compound:

$^1$H NMR (300 Mz, $CDCl_3$) d 1.51 (s, 9H, t-Bu), 2.26 (s, 3H, $CH_3$), 2.36 (s, 3H, $CH_3$), 2.93 (t, J=7.0 Hz, PhC$H_2$), 3.65 (q, J=7.0 Hz, Ph$CH_2$C$H_2$), 4.36 (d, J=5.6 Hz, 2H, CONHC$H_2$), 4.61 (s, 2H, $CH_2$CO), 5.91 (br t, 1H, NH), 6.65 (br t, 1H, NH), 6.77 (s, 1H, pyrazinone H-5),7.12 (s, 1H, NHBOC), 7.21–7.32 (m, 5H, Ph), 7.42 (d, J=8.5 Hz, 1H, pyridine H-3), 7.68 (d, J=8.5 Hz, 1H, pyridine H-4).

Step G: 3-(2-Phenethylamino)-6-methyl-1-(2-amino-6-methyl-5-methylenecarboxamidomethylpyridinyl)-pyrazinone HCl gas was bubbled through a stirred suspension of 3-(2-phenethyl-amino)-6-methyl-1-(2-t-butoxycarbonylamino-6-methyl-5-methylene-carboxamidomethylpyridinyl)-pyrazinone (85 mg, 0.17 mmol) in ethyl acetate (10 ml) at 0° C. until a solution had formed which was saturated with HCl. After 2 h at RT the mixture was degassed with nitrogen and filtered to give the title compound as a bis HCl salt white crystalline solid, m.p.>200° C.:

$^1$H NMR (300 Mz, $CD_3OD$) d 2.18 (s, 3H, $CH_3$),2.52 (s, 3H, $CH_3$),3.00 (t, J=7.4 Hz, Ph$CH_2$), 3.68 (t, J=7.4 Hz, Ph$CH_2$C$H_2$), 4.33 (d, J=5.4 Hz, 2H, CONHC$H_2$), 4.76 (s, 2H, $CH_2$CO), 6.55 (s, 1H, pyrazinone H-5), 6.84 (d, J=9.3 Hz, 1H, pyridine H-3), 7.23–7.31 (m, 5H, Ph), 7.86 (d, J=9.3 Hz, 1H, pyridine H-4); MS (FAB) 407 (M+1)$^+$.

IN VITRO ASSAY FOR DETERMINING PROTEINASE INHIBITION

Assays of human α-thrombin and human trypsin were performed by the methods substantially as described in Thrombosis Research, Issue No. 70, page 173 (1993) by S. D. Lewis et al.

The assays were carried out at 25° C. in 0.05M TRIS buffer pH 7.4, 0.15M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration $\leq$0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The inhibitory activity of compounds of the invention against human thrombin, represented by $K_i$, is less than 24 nM. These are selective compounds, as evidenced by their inhibitory activity against human trypsin (represented by $K_j$), which is at least 1000 nM.

The following tables illustrate additional compounds within the scope of the present invention. Inhibitory activity is represented by "*", indicating $K_i$ greater than or equal to 1 nM, or "**", indicating $K_i$ less than 1 nM.

TABLE 1

| X | Y | Ki |
|---|---|---|
| H | $NHC_2H_5$ | ** |
| H | $NHC_3H_5$ |  |
| H | $NH(CH_2)_2N(CH_3)_2$ |  |
| F | $NHC_2H_5$ |  |
| F | $NHC_3H_5$ |  |
| F | $NH(CH_2)_2N(CH_3)_2$ |  |

TABLE 2

| R | Ki |
|---|---|
| $C_3H_5$ |  |
| $C_3H_5CH_2$ |  |
| $t-C_4H_9$ | * |
| $HO_2CCH_2$ |  |
| $CF_3CH_2$ |  |
| $(CH_3)_2N(CH_2)_2$ |  |

TABLE 3

| R | Ki |
|---|---|
| $PhCH_2C(CH_3)_2$ | * |
| $PhCHCH_3$ |  |
| $PhCH_2CHCO_2H$ |  |
| $n-C_6H_{13}$ |  |

TABLE 4
| R |
|---|
| PhCH$_2$C(CH$_3$)$_2$ |
| PhCHCH$_3$ |
| PhCH$_2$CHCO$_2$H |
| n-C$_6$H$_{13}$ |
Additional exemplary compounds of the invention, with associated inhibitory activity of the compounds against human thrombin, (represented by Ki) are shown below. As in the tables above, inhibitory activity is represented by "*", indicating Ki greater than or equal to 1 nM, or "**", indicating Ki less than 1 nM.
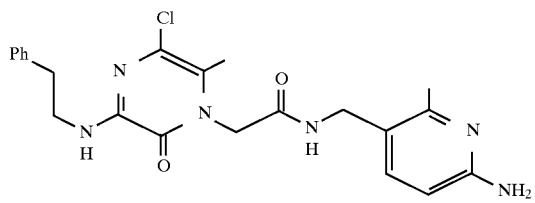 *
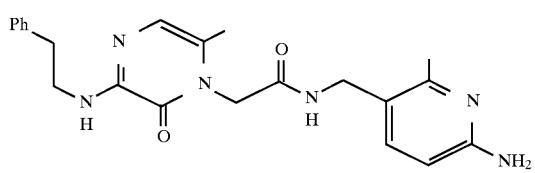 **
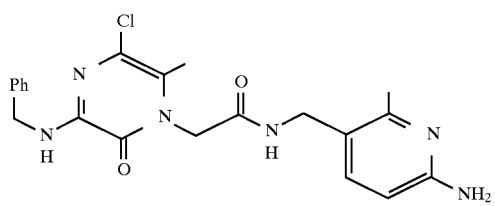 *
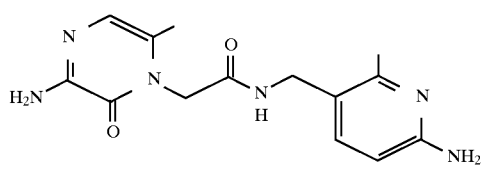 *

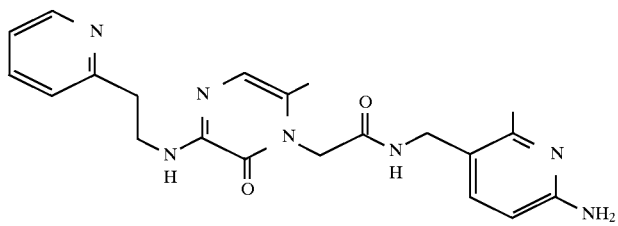 **
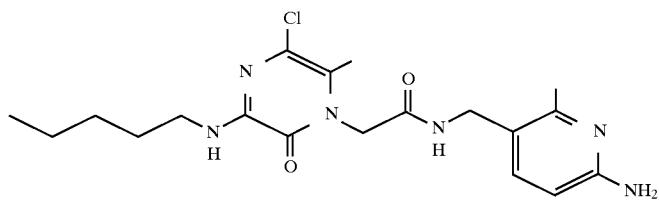 *
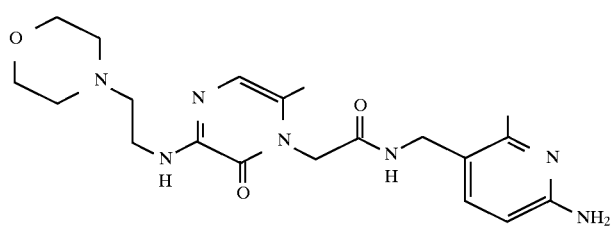 *
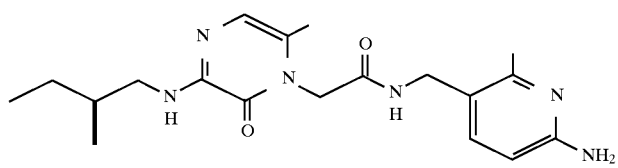 *
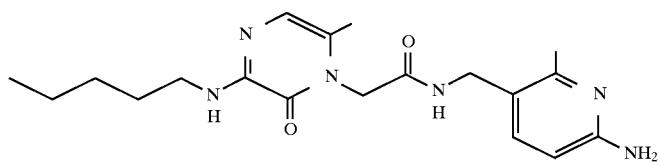 *
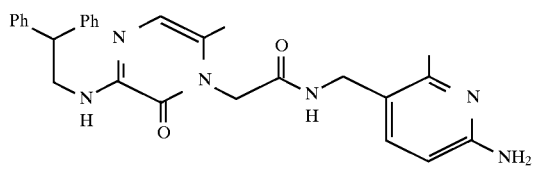 **
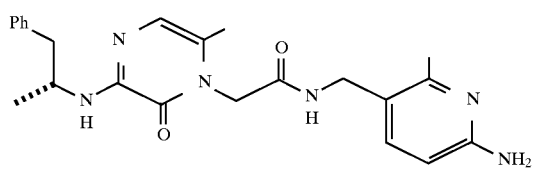 **
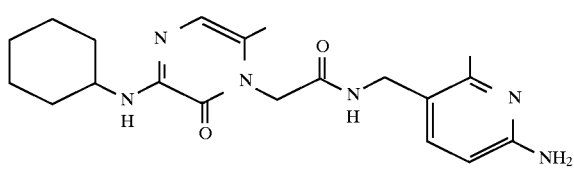 *

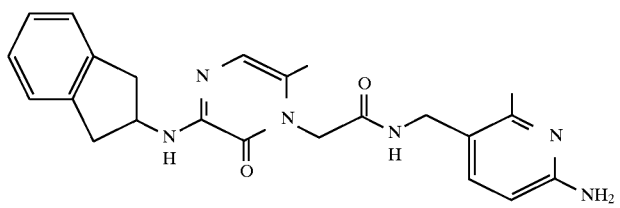
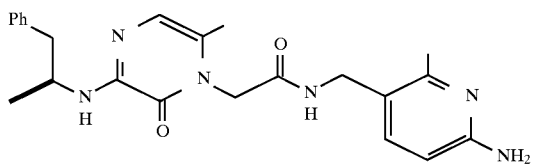
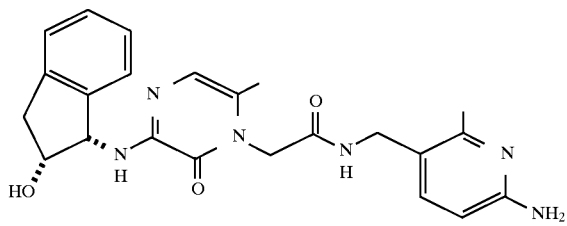
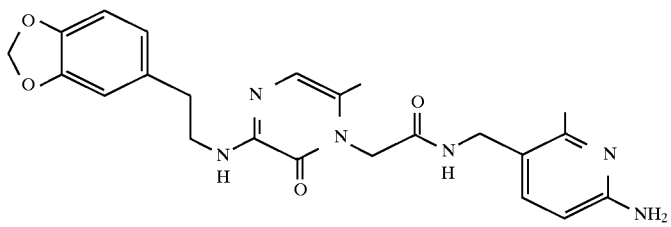
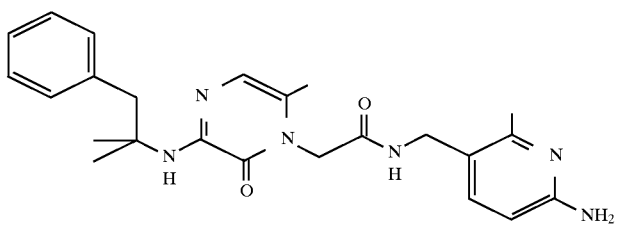
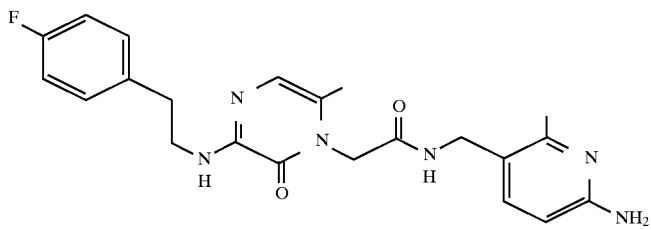
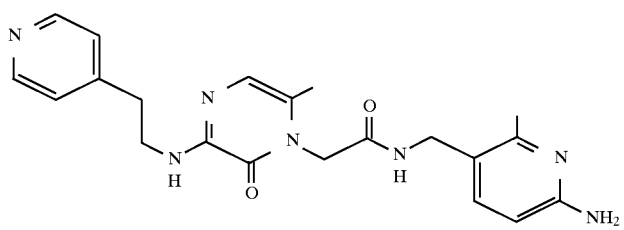

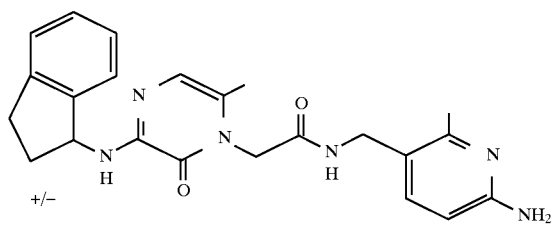
\*
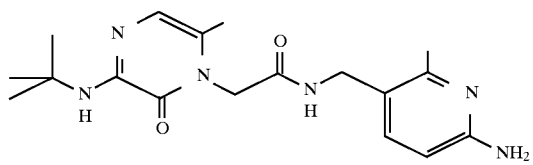
\*
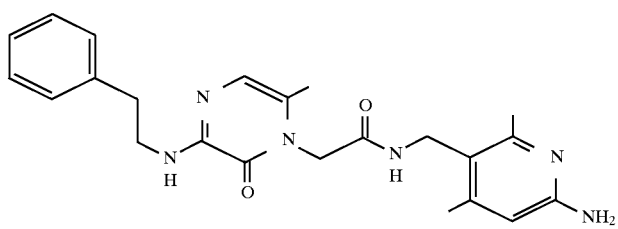
\*\*
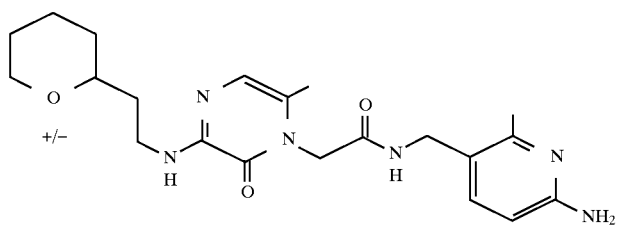
\*
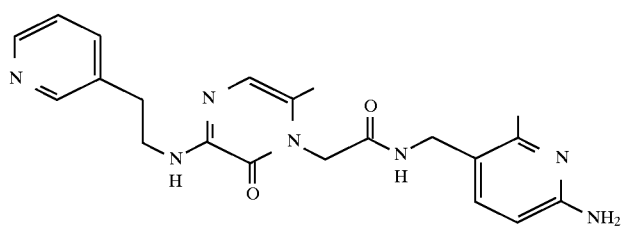
\*\*
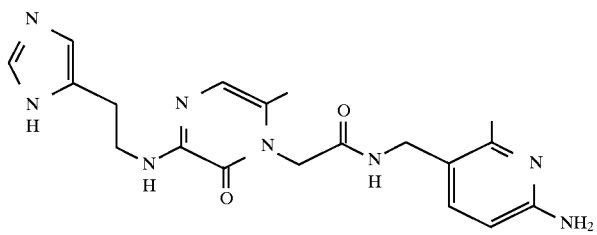
\*
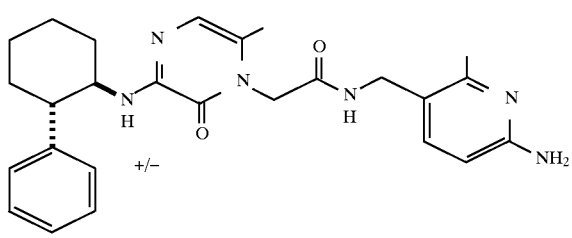
\*

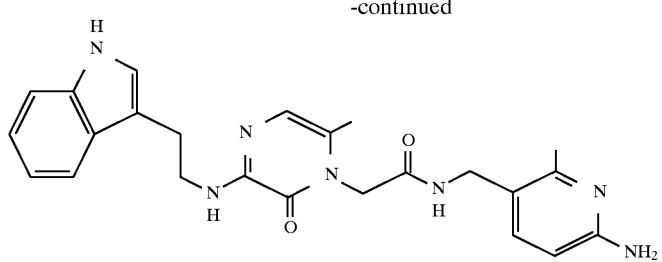
*
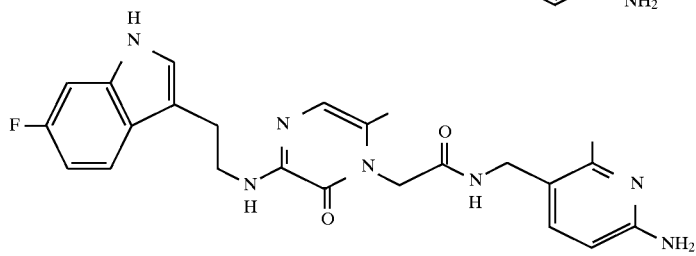
*
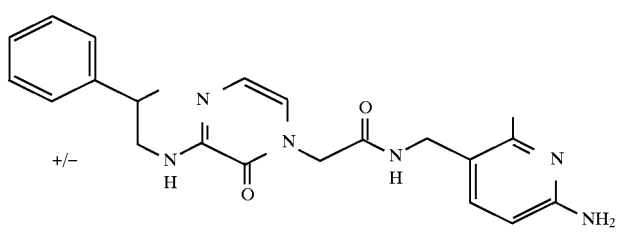
*
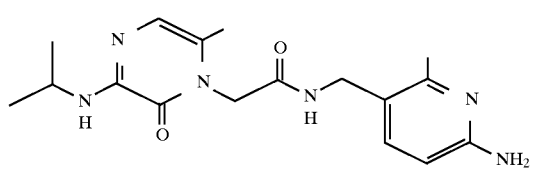
*
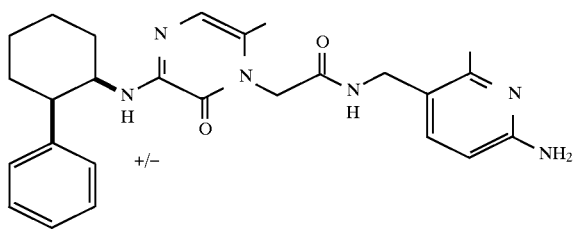
*
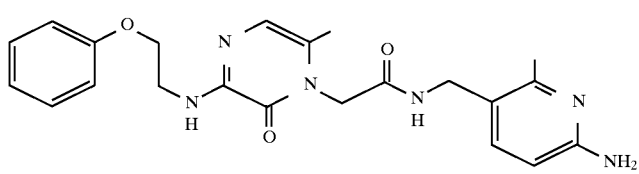
*
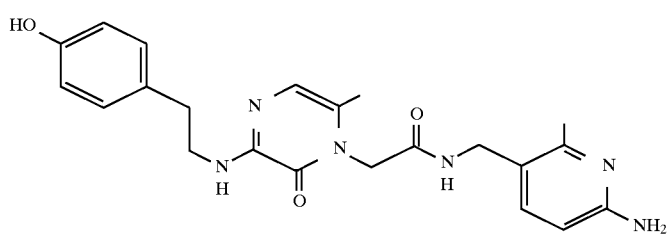
*
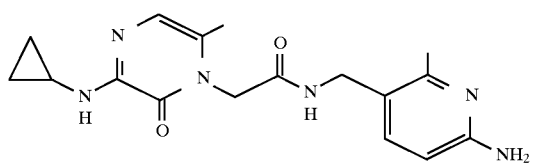
*

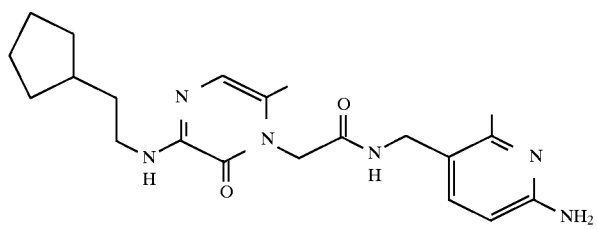
*
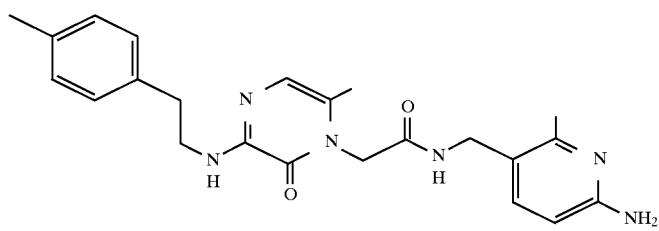
**
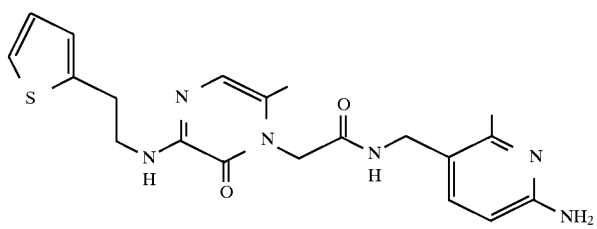
*
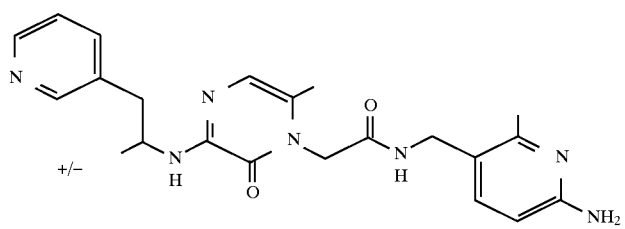
**
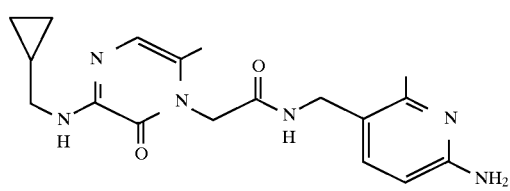
*
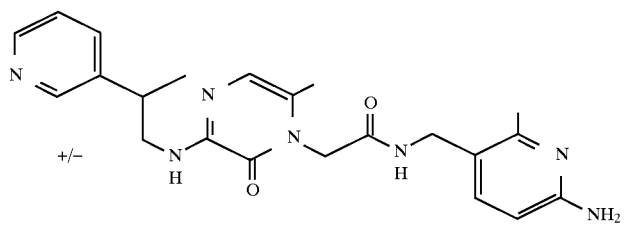
**
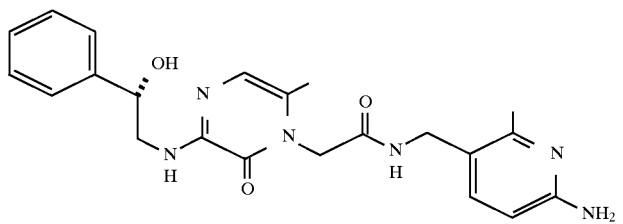
*

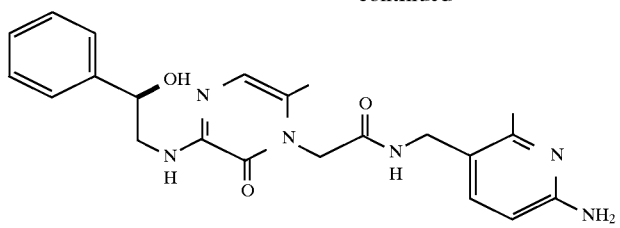
*
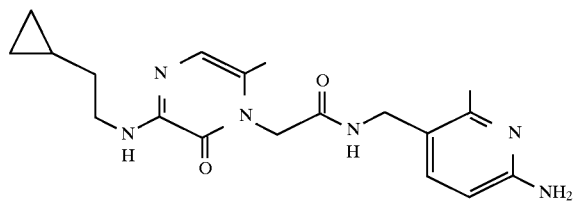
*
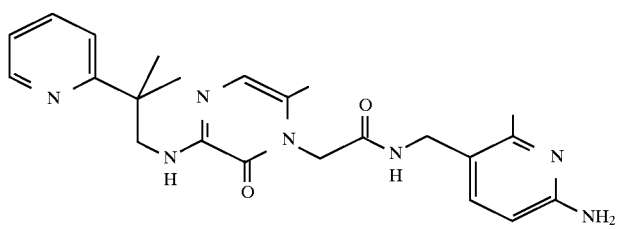
**
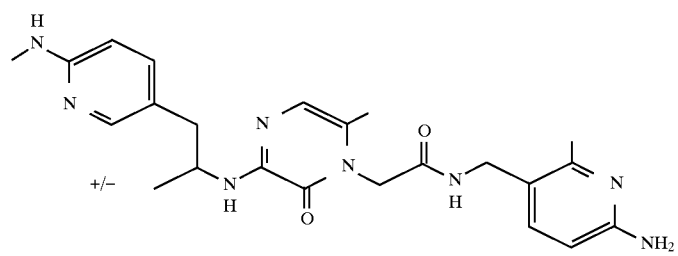
*
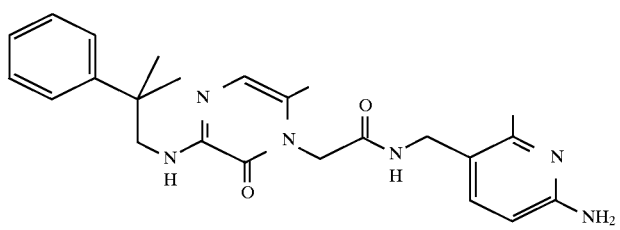
*
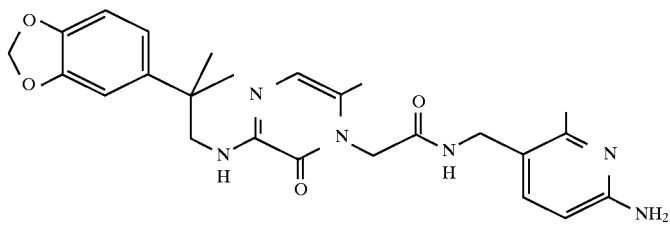
**
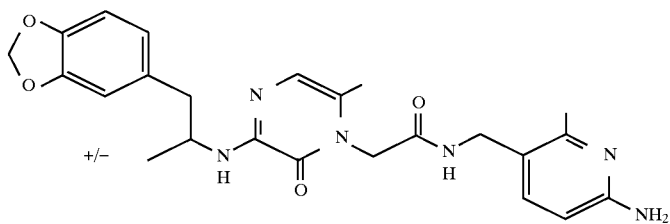
**

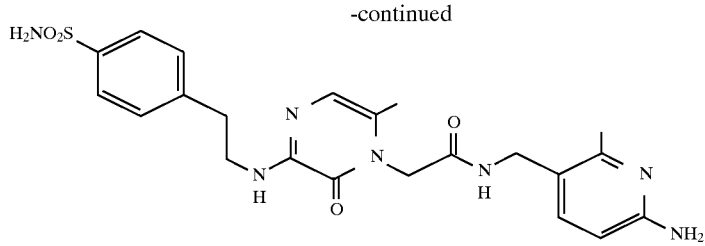
\*
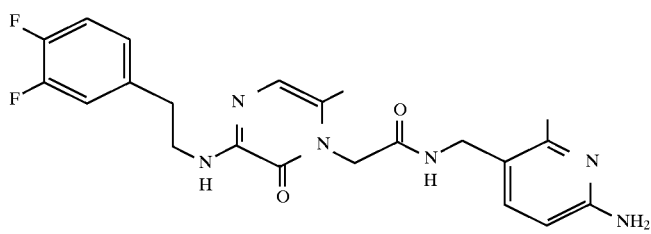
\*\*
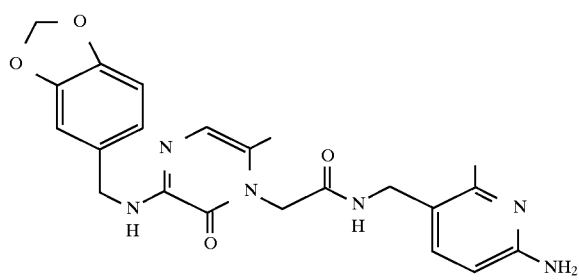
\*
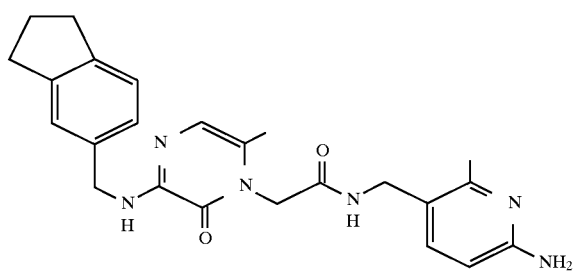
\*
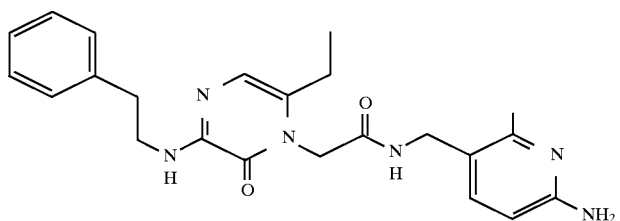
\*
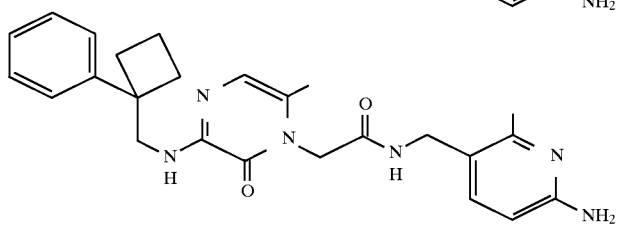
\*\*
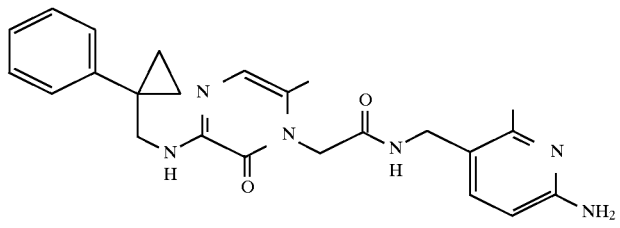
\*\*

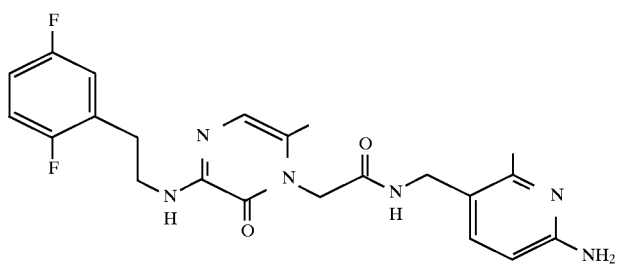
**
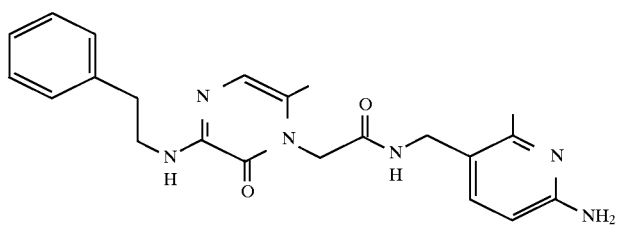
*
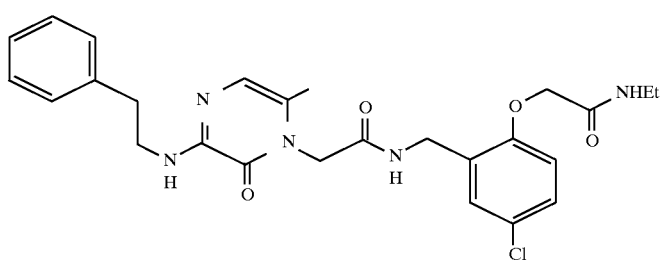
**
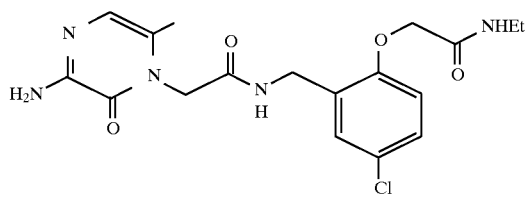
*
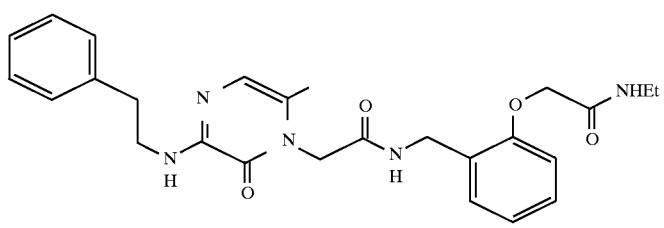
**
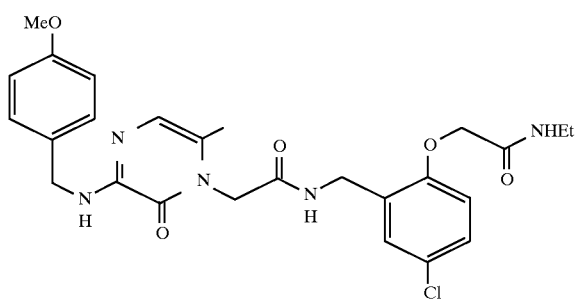
**

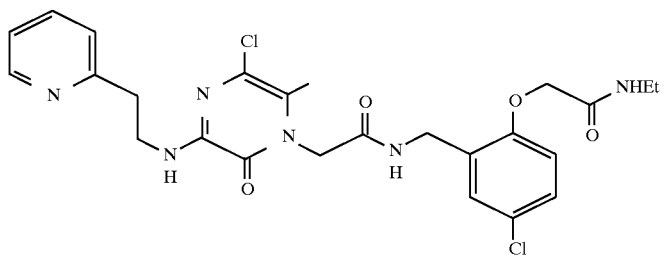
**
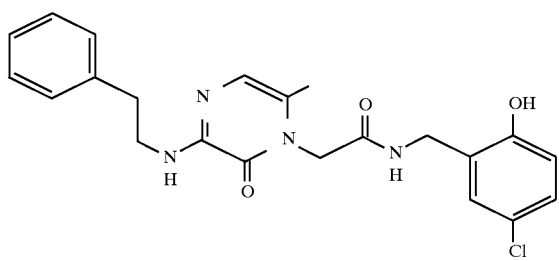
*
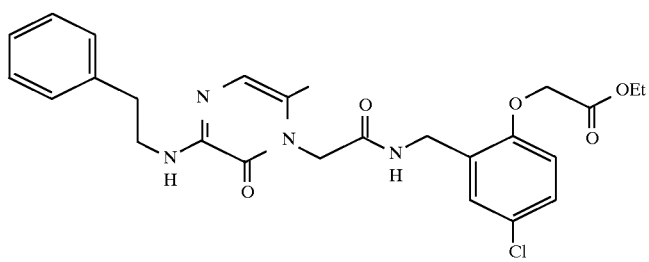
**
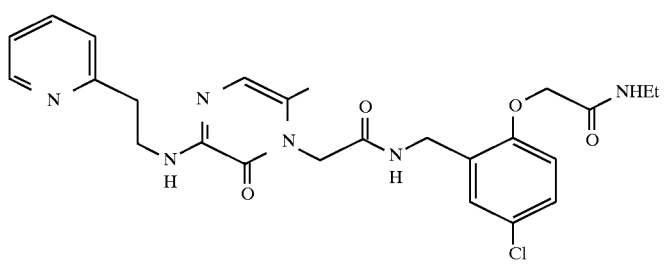
**
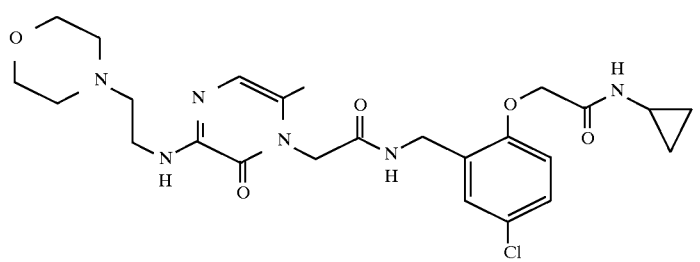
*
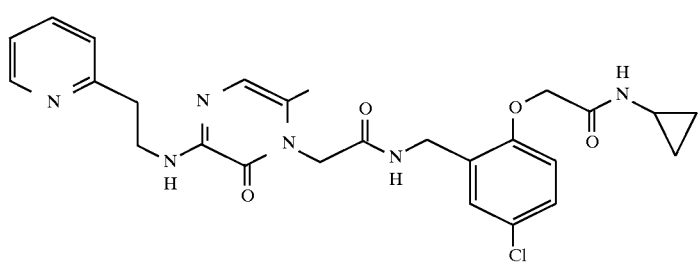
**

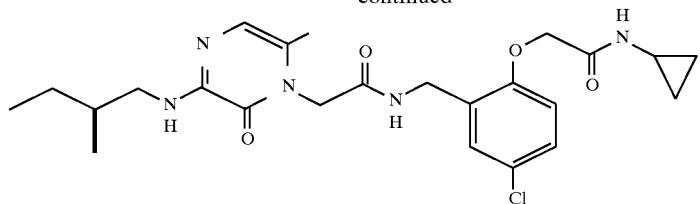 **
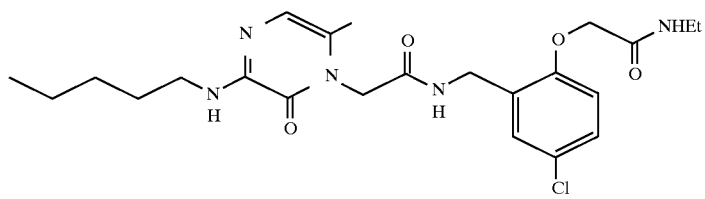 **
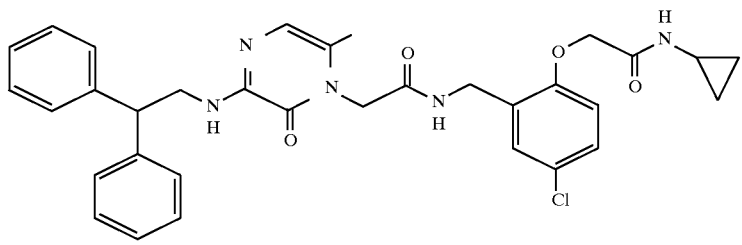 **
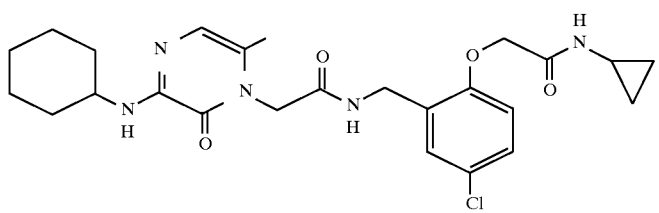 *
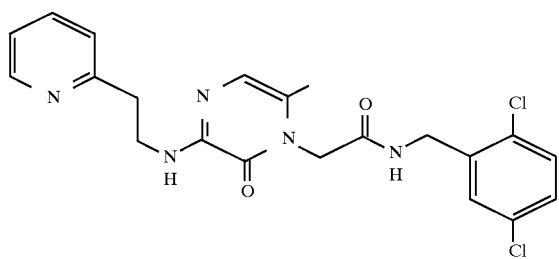 **
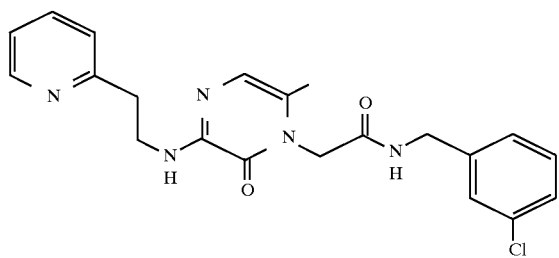 *
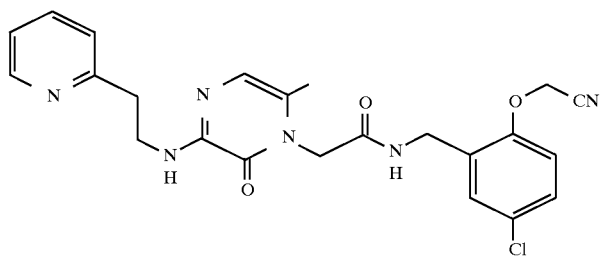 **

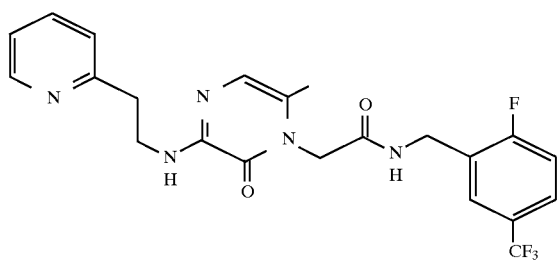
*
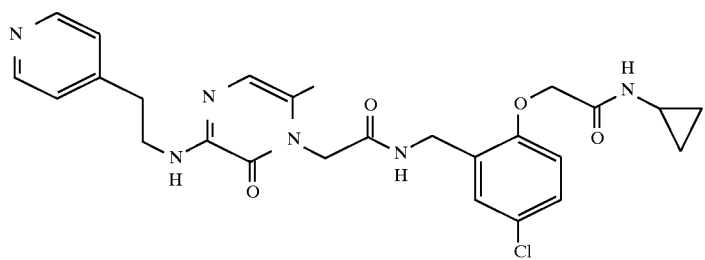
**
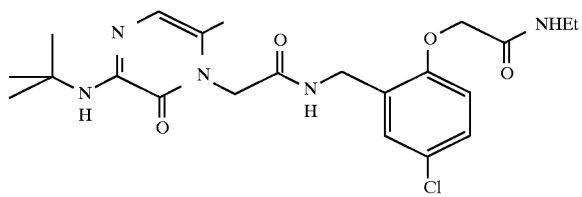
*
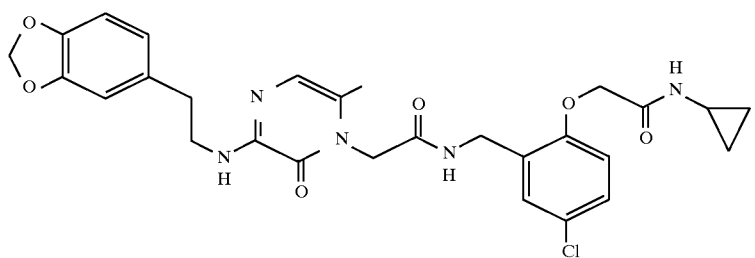
**
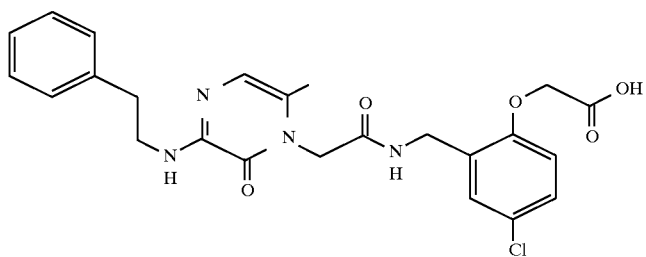
*
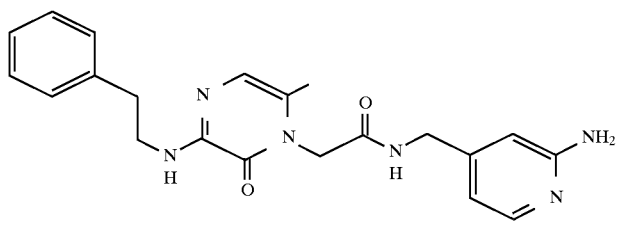
*

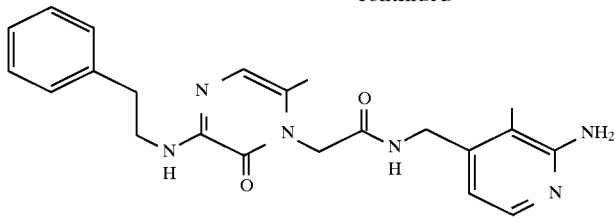

EXAMPLE LXXXIII

In Vivo Studies to Measure Thrombotic Occlusions

Studies of 3 (2-Phenylethylarnino)-6-methyl-1-(2-amino-6-following rat ferric chloride assay substantially as described in *Thrombosis Research*, No. 60, page 269(1990) by Kurtz et al were used to determine in vivo activity of the thrombin inhibitors of the invention. Male Sprague-Dawley rats (b)ody weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery is exposed and a 1.3 mm diameter Doppler flow probe was placed on the vessel. Body temperature was maintained at 37° C. using a heat lamp.

6 rats were randomized to continuous intravenous infusions of saline or test compound administered via the tail vein. Test compound was administered at a rate of 10 μg/kg/min. Treatment infusions were initiated 60 min before the placement of a 3 mm square piece of Whatman No. 1 filter paper saturated with 35% $FeCl_3$ onto the exposed carotid artery distal to the flow probe. Treatment infusions were continued for an additional 90 minutes after the application of $FeCl_3$ (total infusion duration 150 minutes) if thrombotic occlusions did not occur, or were terminated 30 minutes after thrombotic occlusion of the vessel. Time to occlusion was defined as the time from application of $FeCl_3$ to thrombotic occlusion of the vessel. At the termination of the study (90 minutes after application of $FeCl_3$ in animals which did not occlude, or at 30 minutes after thrombotic occlusion), 3 ml blood samples were drawn by cardiac puncture into 0.3 ml of 3.8% sodium citrate.

The results of the study showed that the tested compound was fully efficacious. None of the rats treated with the test compound showed evidence of thrombotic occlusion.

EXAMPLE LXXXIV

Tablet Preparation

Tablets containing 25.0, 50.0, and 100.0 mg., respectively, of the following active compounds are prepared as illustrated below (compositions A–I):

3-(2-Phenylethylamino)-6-methyl-1-(2-amino-6-methyl-5-methylenecarboxamidomethylpyridinyl)-2-pyridinone (Active I), 3-(2-Phenethylamino)-6-methyl-1-[ethyl-(2-methylene-carboxamidomethyl-4-chlorophenoxy)-acetamido]-2-pyrazinone (Active II), and 3-Amino-6-methyl-1-[ethyl-(2-methylene-carboxamidomethyl-4-chlorophenoxy)-acetamido]-2-pyrazinone (Active III).

TABLE FOR DOSES CONTAINING FROM 25–100 MG OF THE ACTIVE COMPOUND

| Component | Amount - mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Micro-crystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE LXXXV

Tablet Preparation

Exemplary compositions of 3-(2-Phenethylamino)-6-methyl-1-(2-amino-6-methyl-5-methylcarboxamidomethylpyridinyl)-pyrazinone dihydrochloride Type A monohydrate (Active IV) tablets are shown below:

| Component | 0.25 mg | 2 mg | 10 mg | 50 mg |
| --- | --- | --- | --- | --- |
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation Via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE LXXXVI

Intravenous Formulations

Intravenous formulations of 3-(2-Phenethylamino)-6-methyl-1-(2-amino-6-methyl-5-methylcarboxamidomethylpyridinyl)-pyrazinone dihydrochloride Type A monohydrate (Active IV) were prepared according to general intravenous formulation procedures.

| Component | Estimated range |
| --- | --- |
| Active IV | 0.12–0.61 mg |
| D-glucuronic acid* | 0.5–5 mg |
| Mannitol NF | 50–53 mg |
| 1N Sodium Hydroxide | q.s. pH 3.9–4.1 |
| Water for injection | q.s. 1.0 mL |

Exemplary compositions A–C are as follows:

| Component | A | B | C |
| --- | --- | --- | --- |
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the formula of the formula

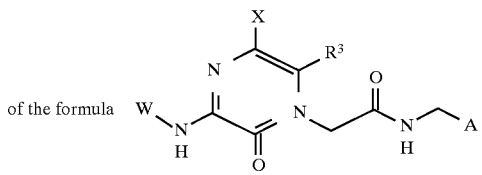

or a pharmaceutically acceptable salt thereof, wherein

A is i)

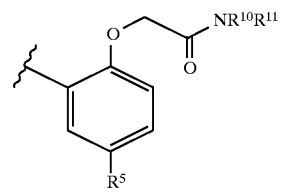

wherein
$R^5$ is H, fluoro, chloro, and
$R^{10}$ and $R^{11}$ are independently selected from
H,
$C_2H_5$,
$C_3H_5$,
$(CH_2)_2N(CH_3)_2$,
$C_3$ cycloalkyl, ii)

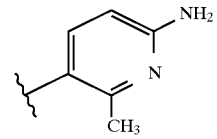

iii)

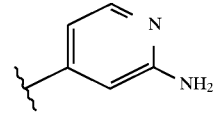

iv)

-continued
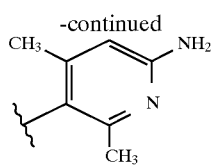
v)
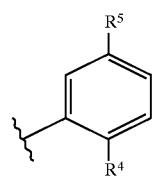
wherein R⁴ is OH, chloro, H, —OCH₂CN, fluoro, —OCH₂COOH, and R⁵ is chloro or CF₃,
vi)
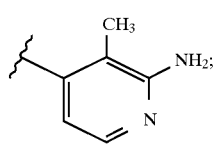
R³ is CH₃, or CH₂CH₃;
X is H or chloro; and
W is
  PhCH₂CH₂,
  (CH₃)₃C—,
  HOOCCH₂,
  CF₃CH₂,
  (CH₃)₂N(CH₂)₂,
  PhCH₂O(CH₂)₂,
  PhCH(CH₃),
  PhCH₂CH(COOH),
  CH₃(CH₂)₅,
  PhCH₂,
  H,
  CH₃(CH₂)₄,
  CH₃CH₂CH(CH₃)CH₂,
  (Ph)₂CHCH₂,
  PhCH₂CH(CH₃),
  PhCH₂C(CH₃)₂,
  PhCH(CH₃)CH₂,
  (CH₃)₂CH,
  PhCH(OH)CH₂,
  PhC(CH₃)CH₂,
  (Ph)₂CHCH₂,
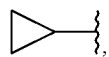
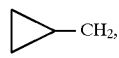
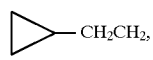
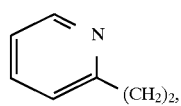
-continued
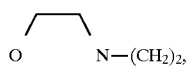
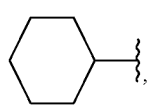
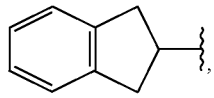
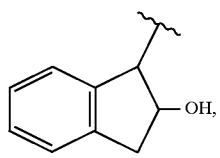
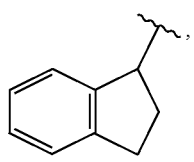
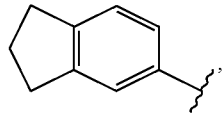
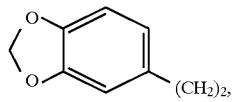
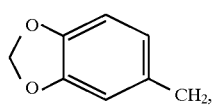
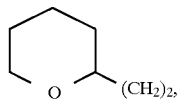
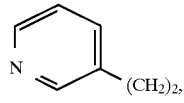
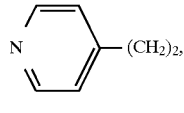
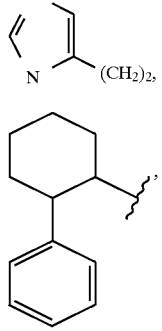

-continued
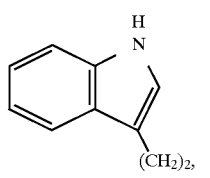
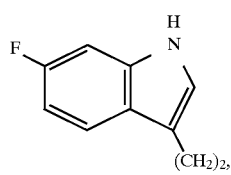
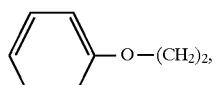
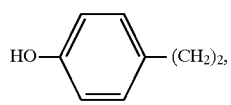
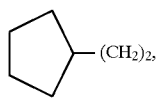
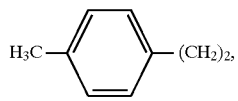
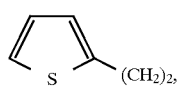
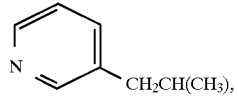
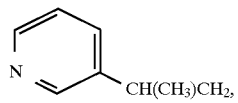
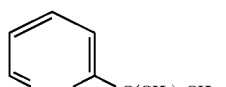
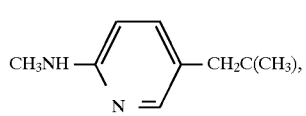
-continued
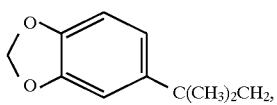
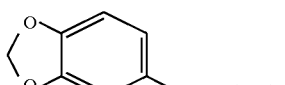
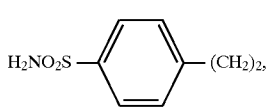
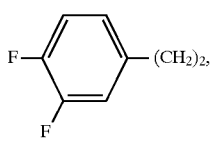
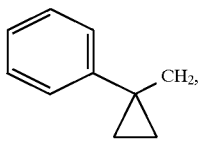
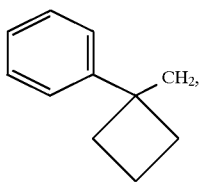
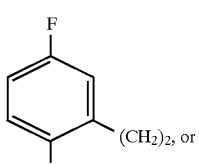
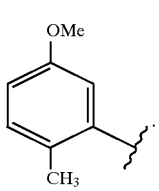
2. The compound of claim 1, or a pharmaceutically acceptable salt thereof, selected from the group consisting of:
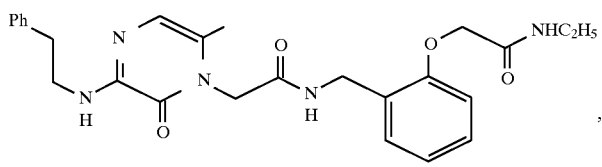

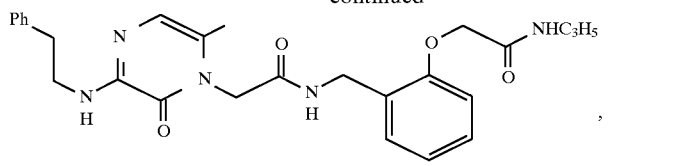
,
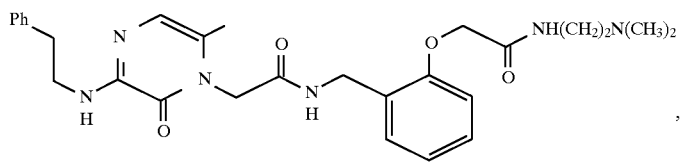
,
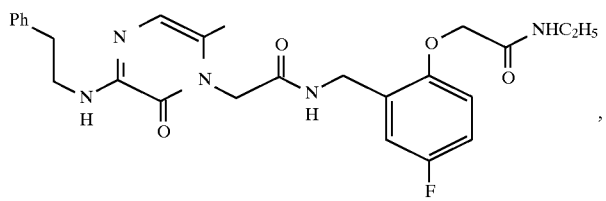
,
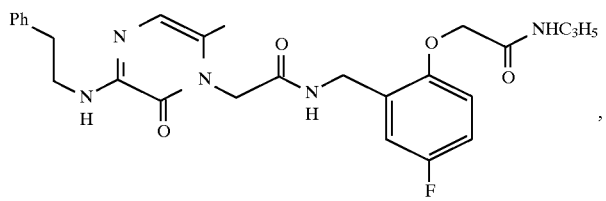
,
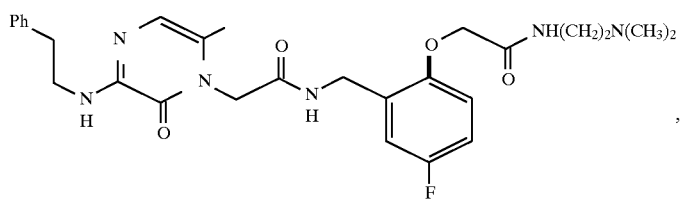
,
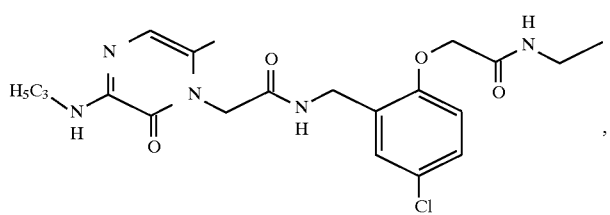
,
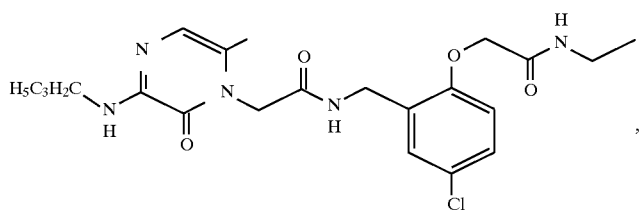
,
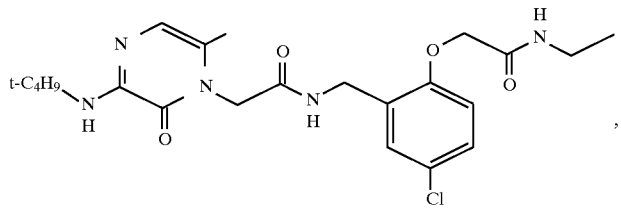
, -continued
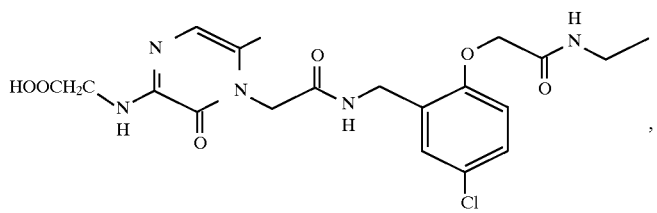
,
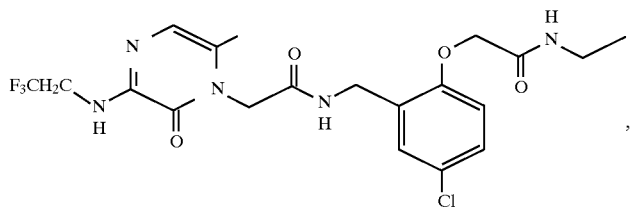
,
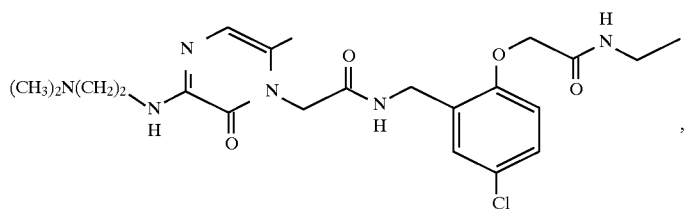
,
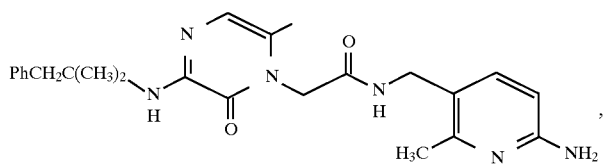
,
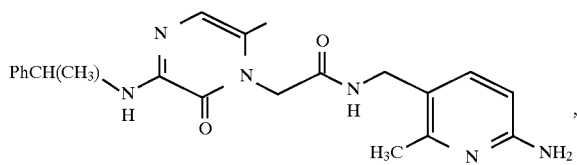
,
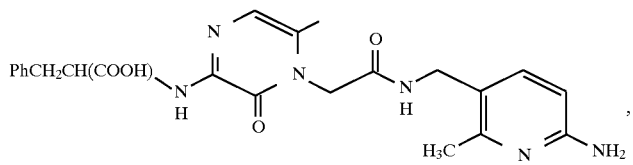
,
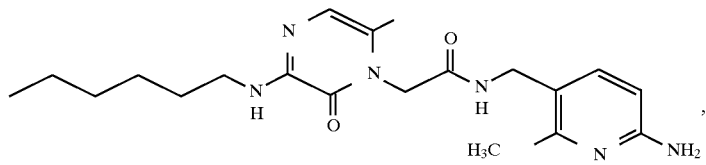
,
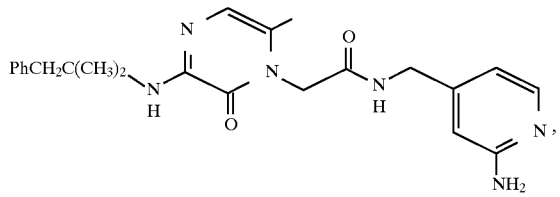
,

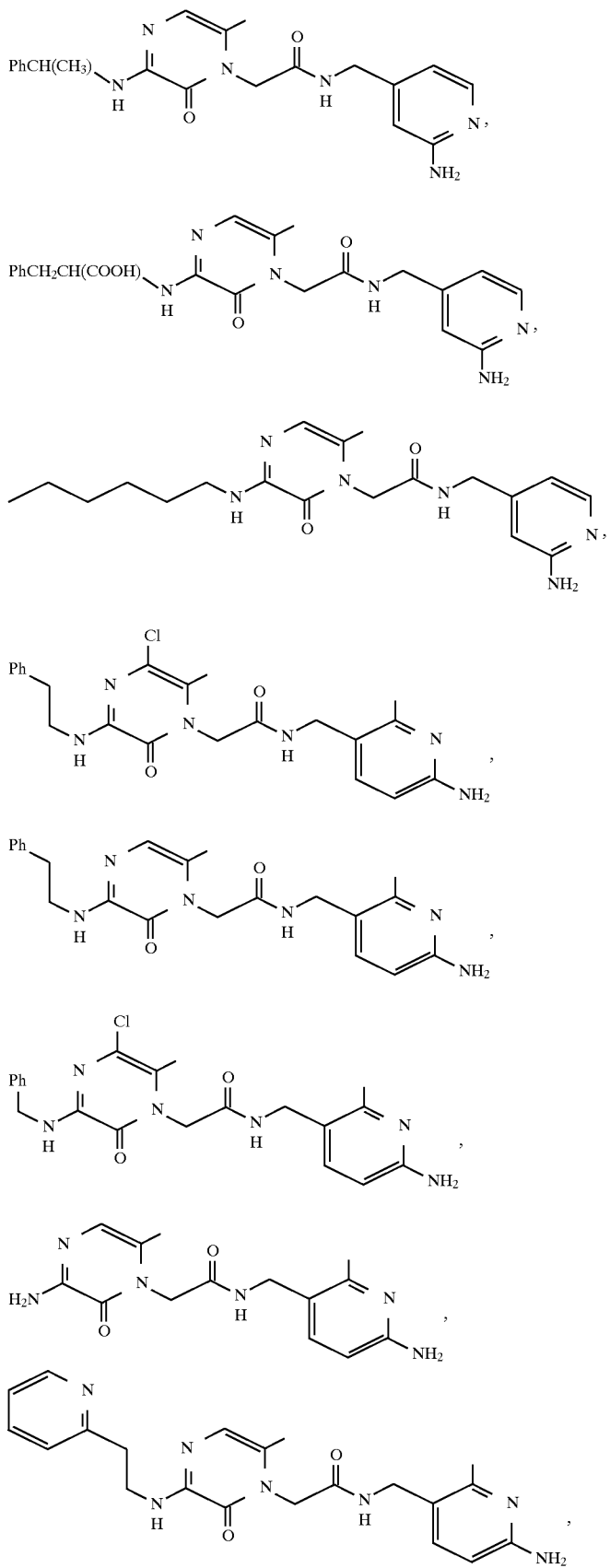

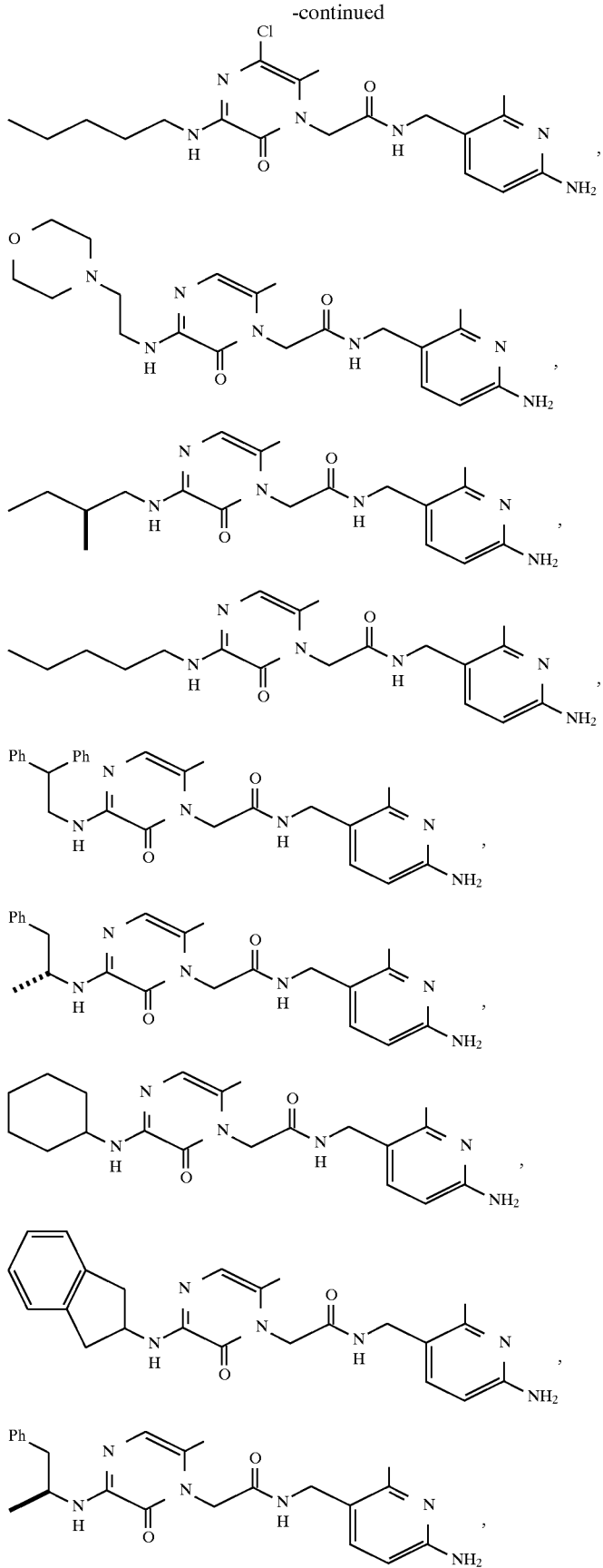

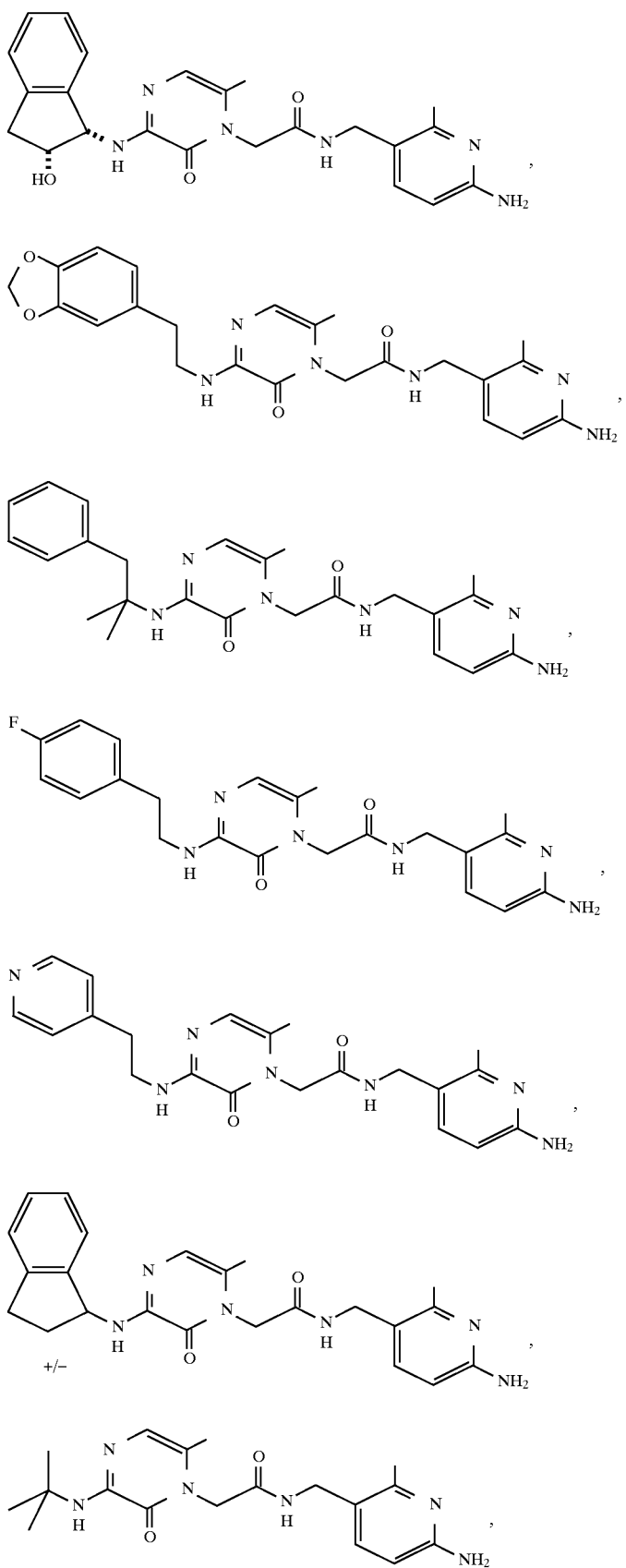

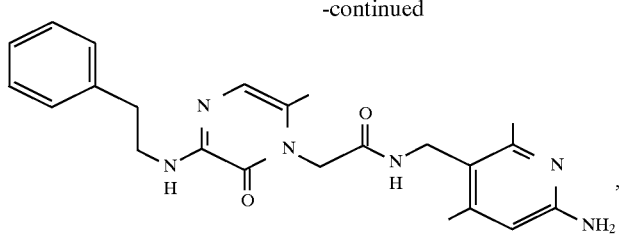,
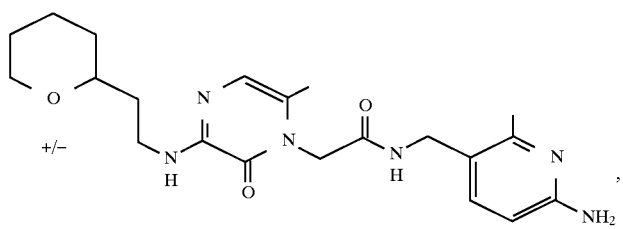,
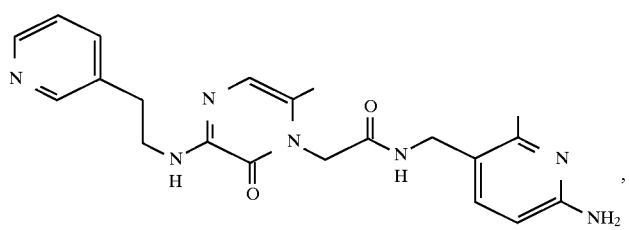,
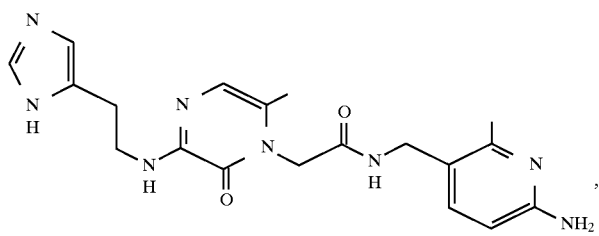,
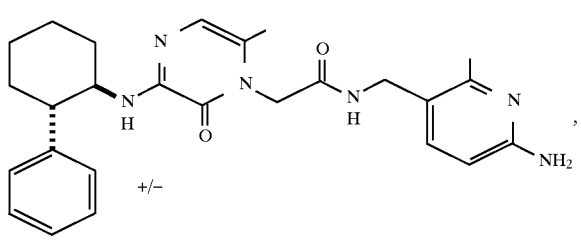,
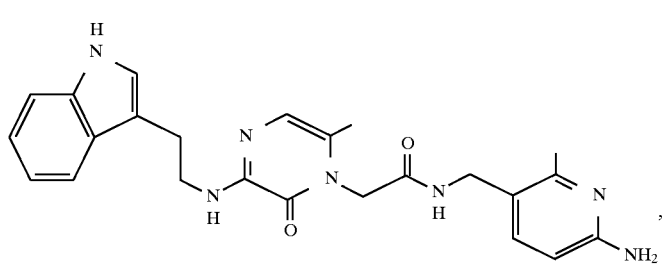,
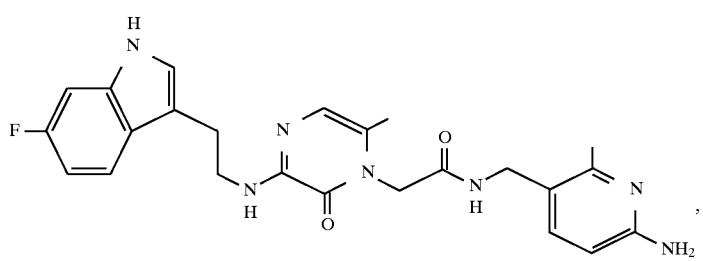,

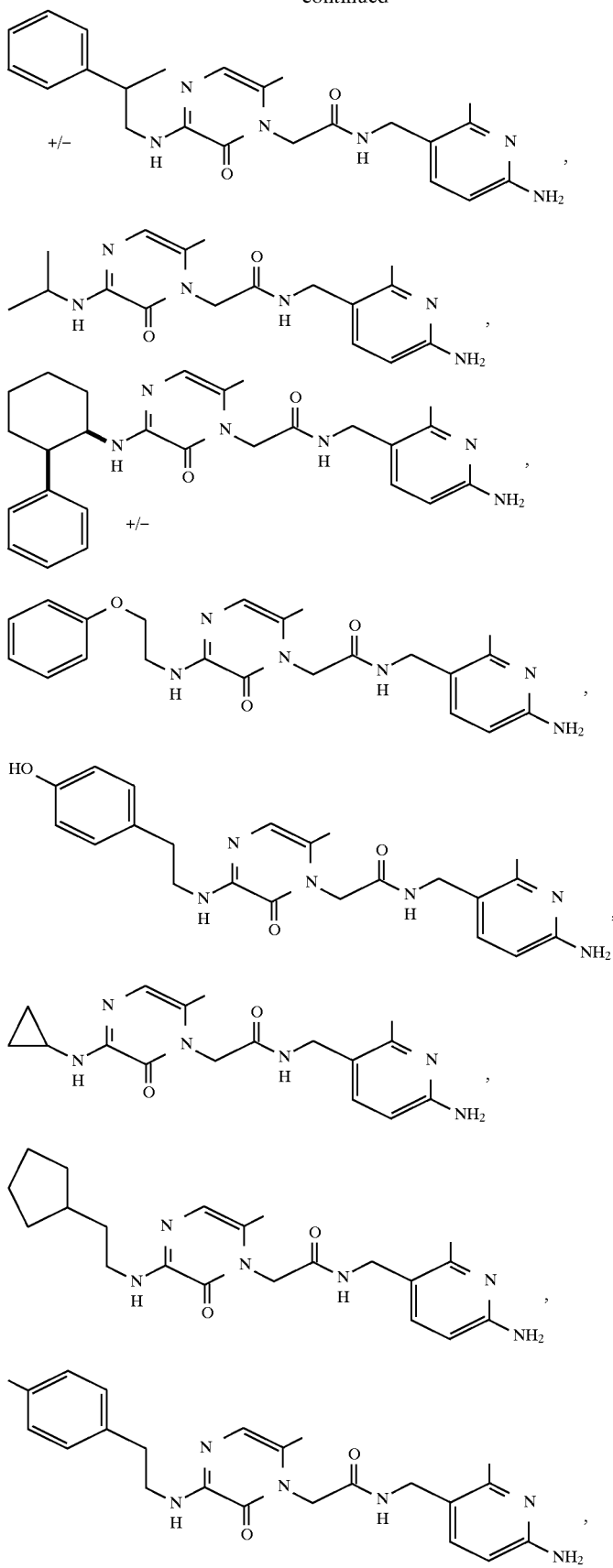

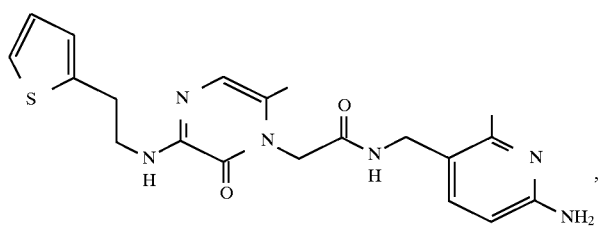
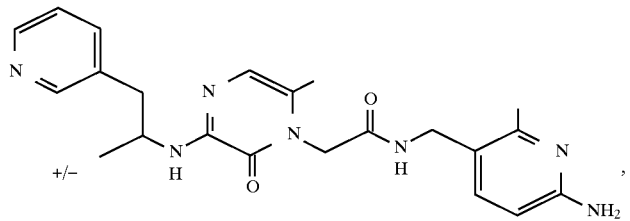
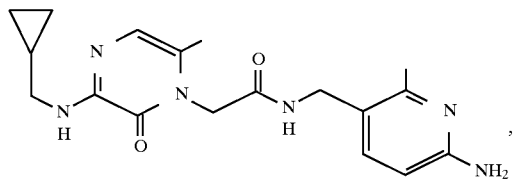
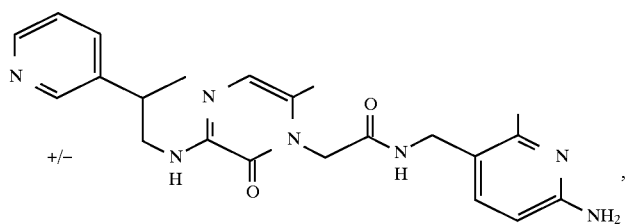
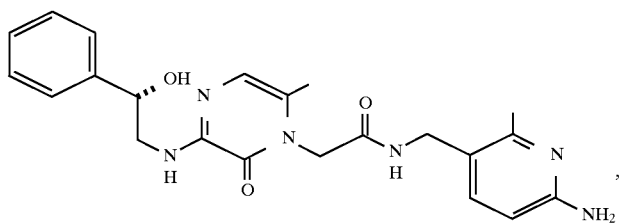
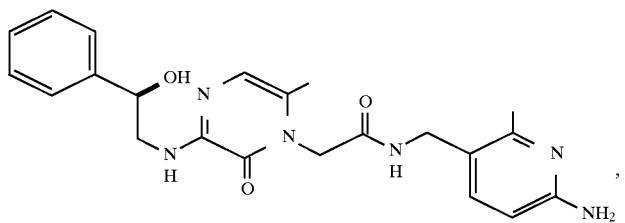
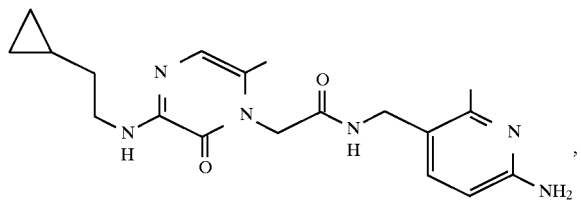

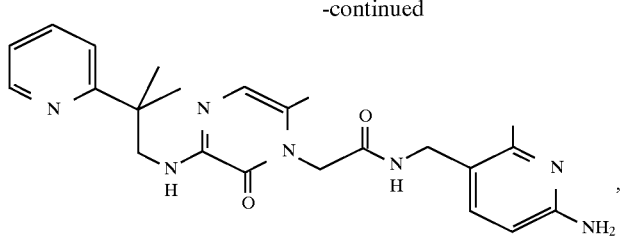,
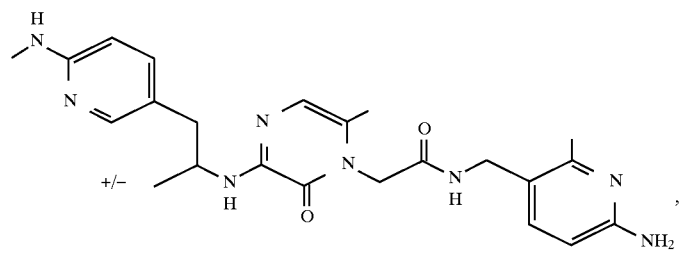,
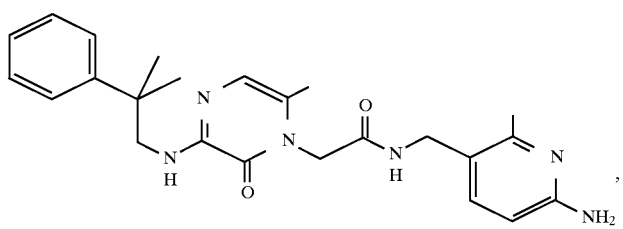,
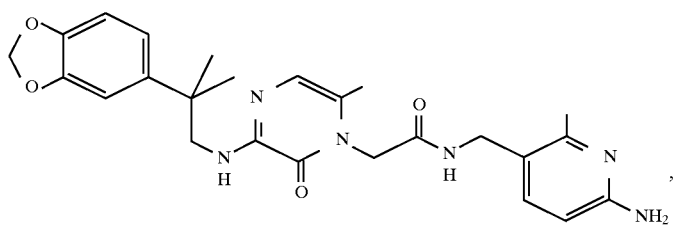,
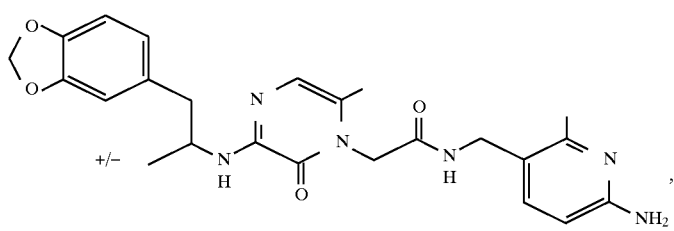,
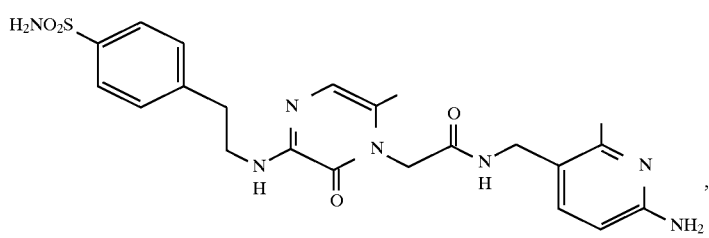,
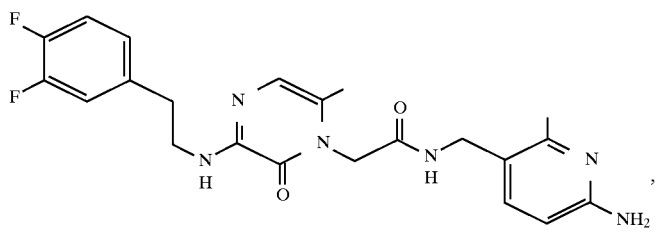, -continued
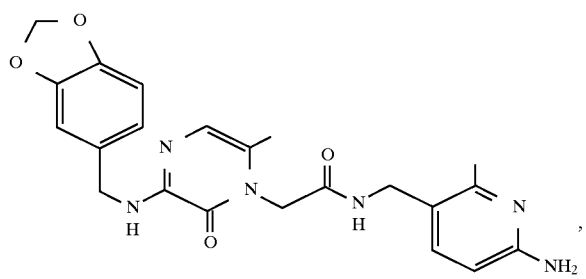
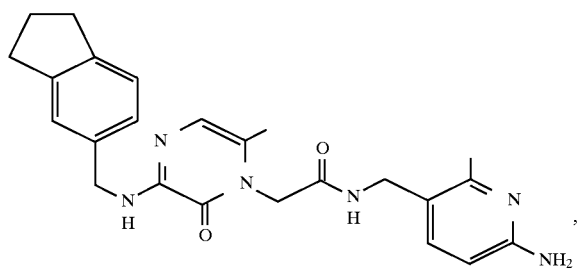
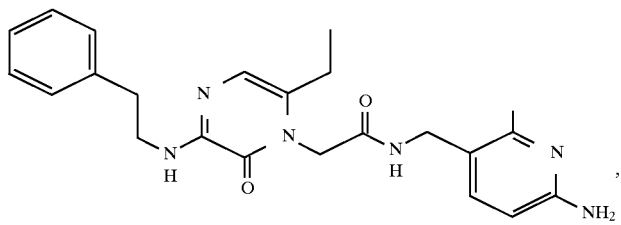
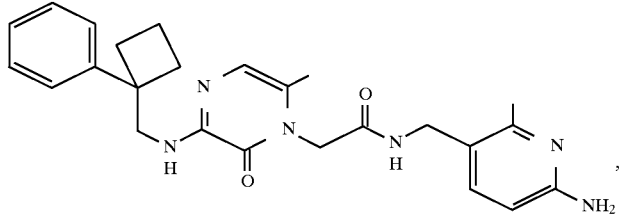
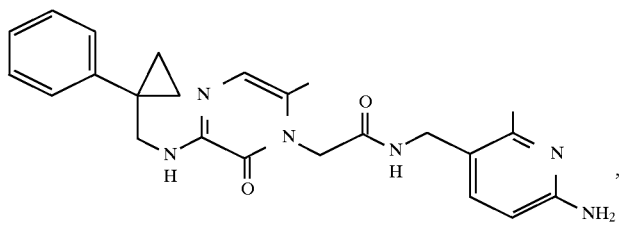
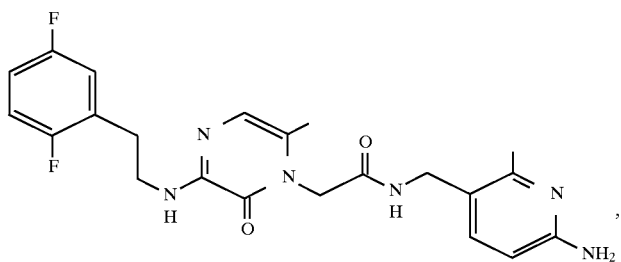

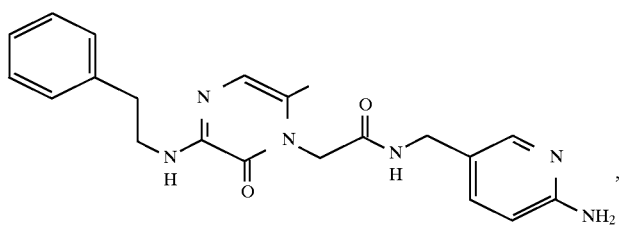
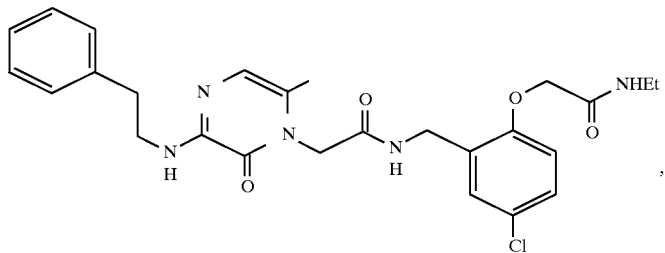
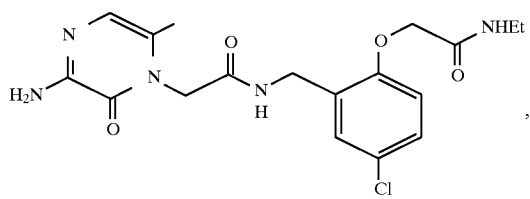
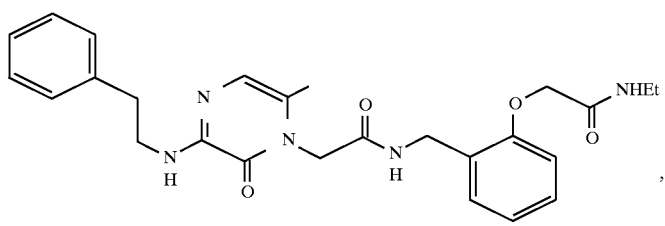
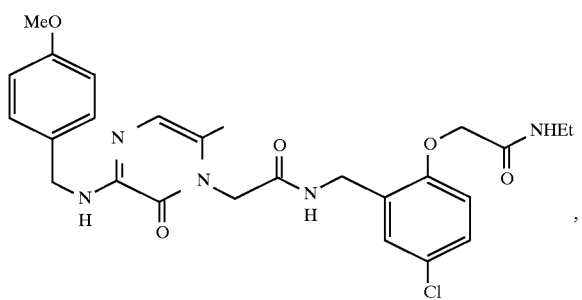
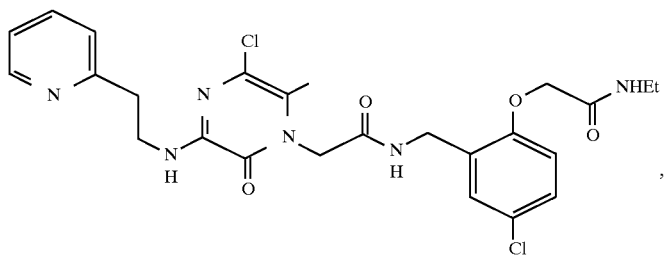

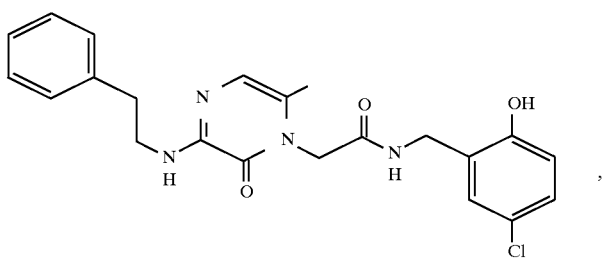,
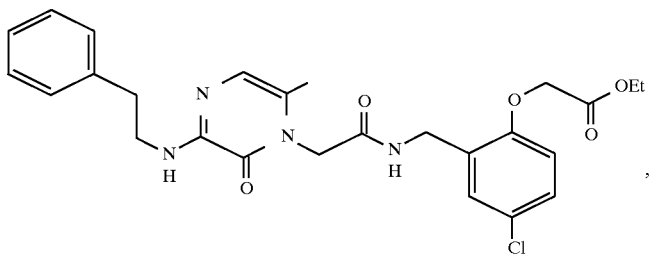,
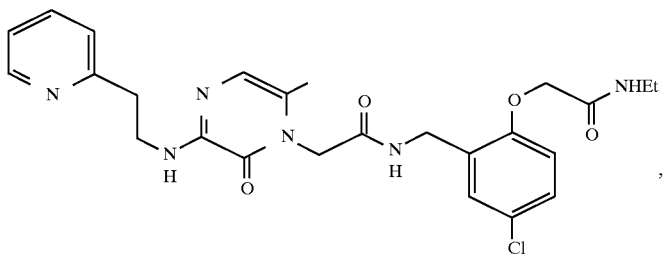,
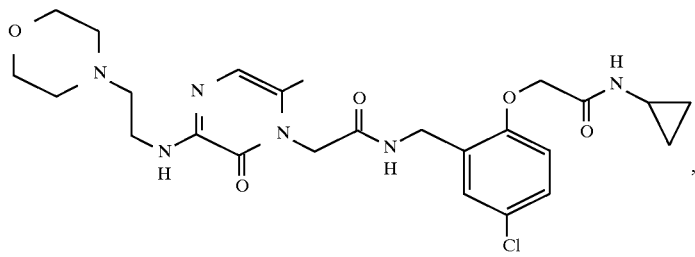,
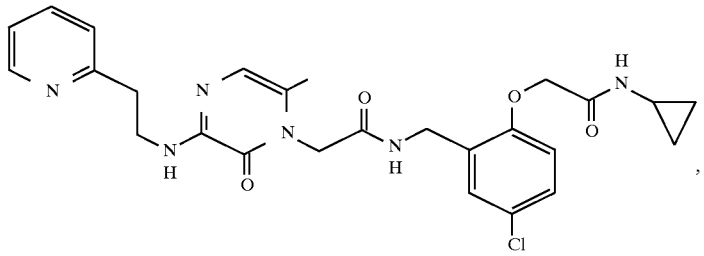,
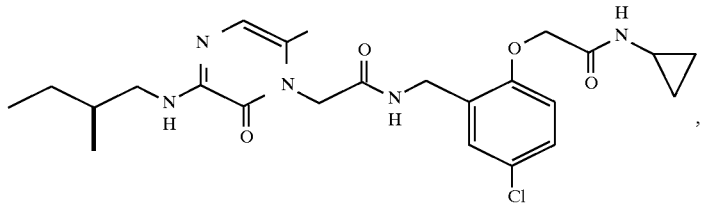,

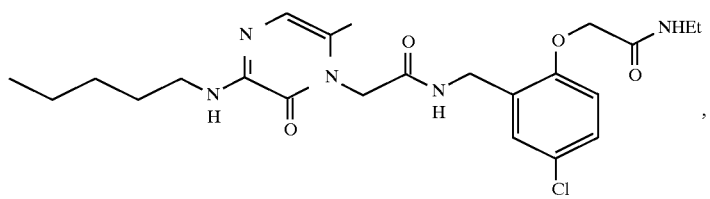,
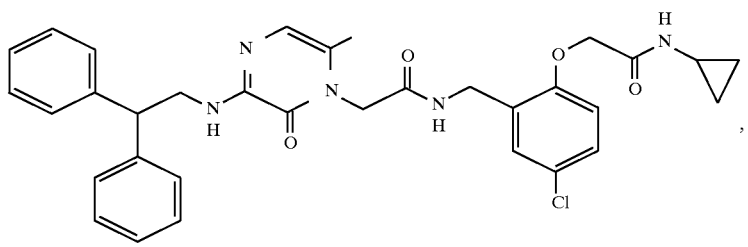,
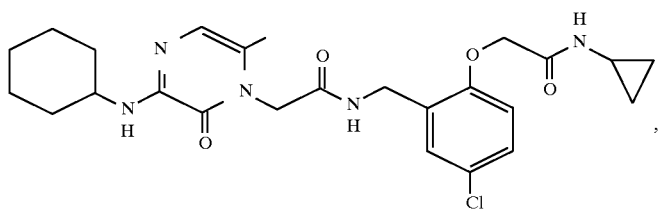,
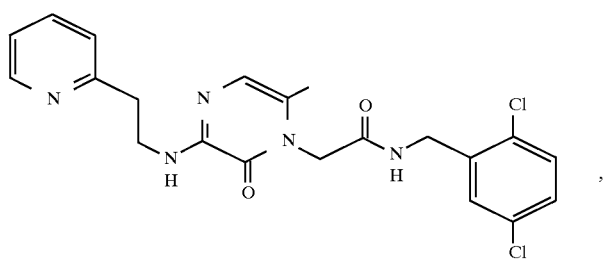,
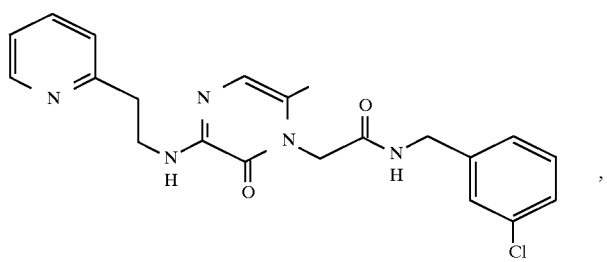,
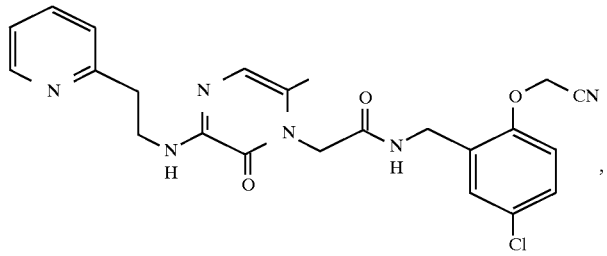,

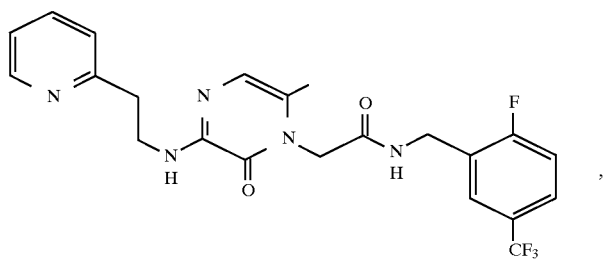
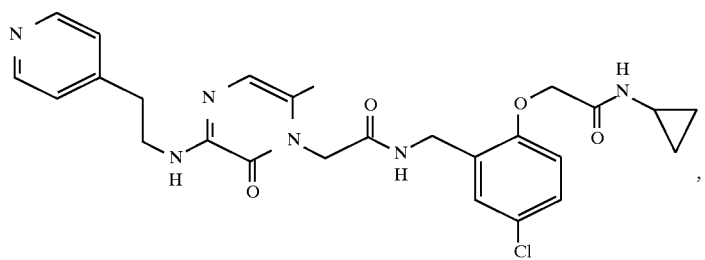
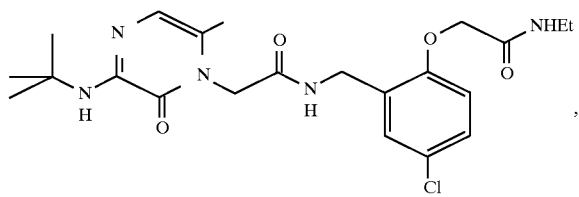
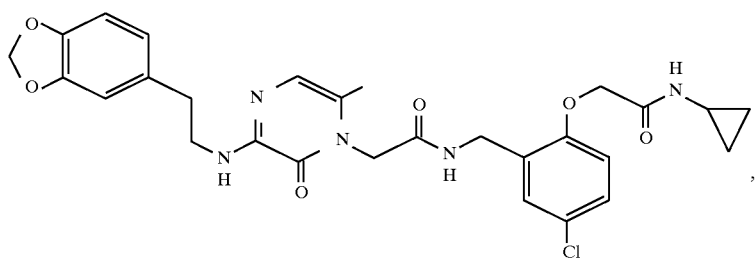
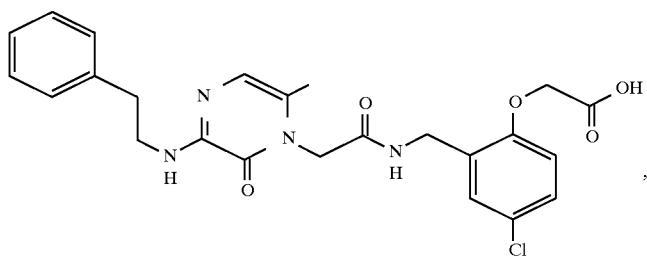
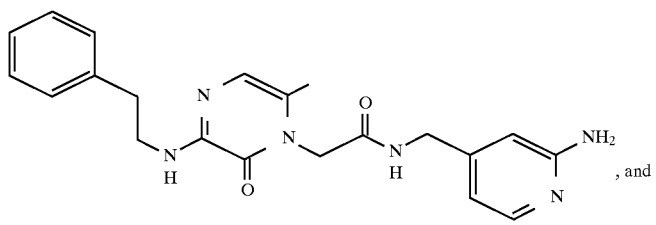
, and

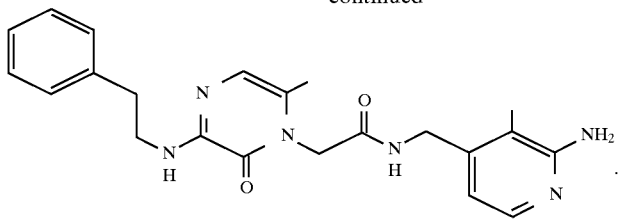
3. The compound of claim 2, or a pharmaceutically acceptable salt thereof, wherein the compound is selected from the group conistsing of
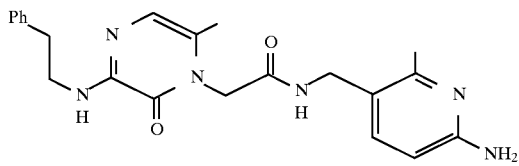
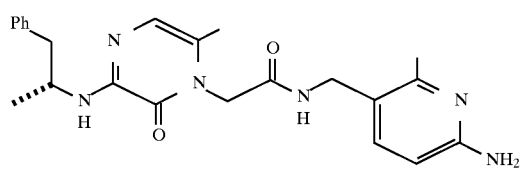
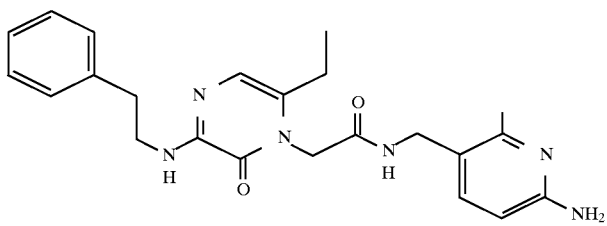
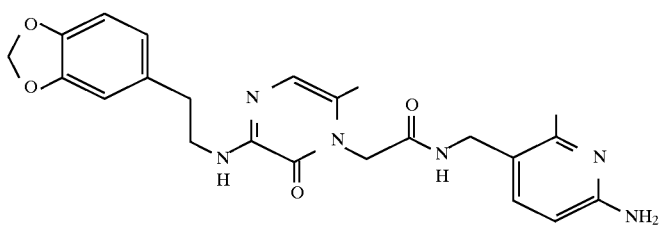
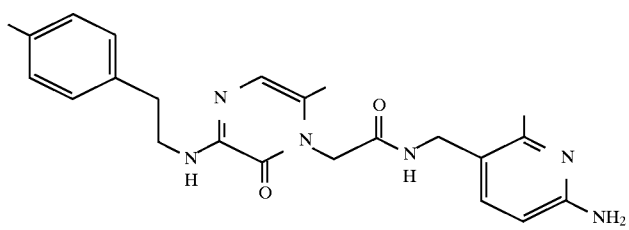
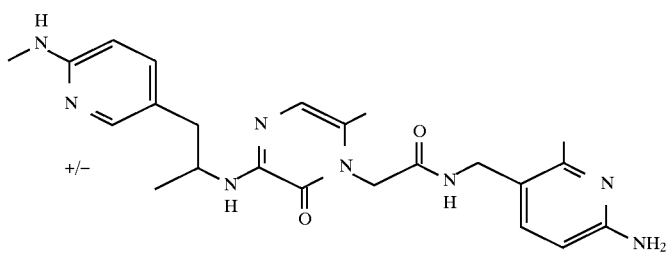

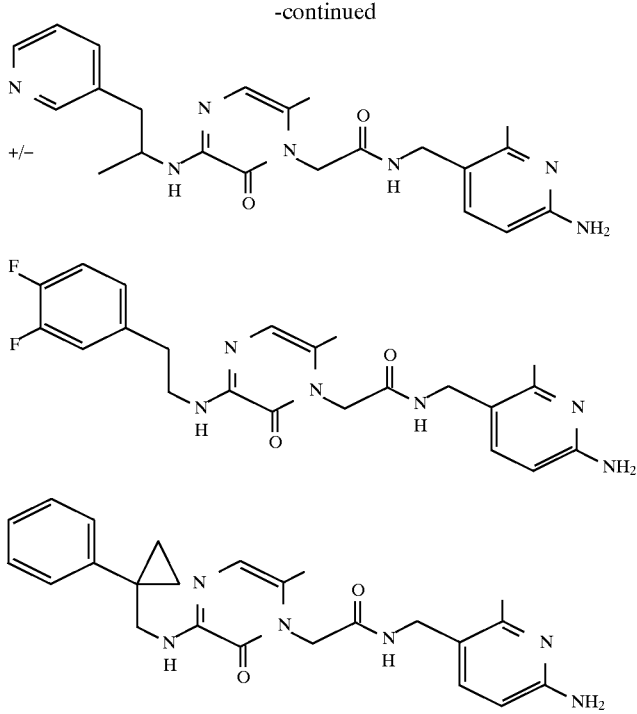

4. The compound of claim 3, or a pharmaceutically acceptable salt thereof, wherein the compound is 3-(2-Phenethylamino)-6-methyl-1-(2-amino-6-methyl-5-methylcarboxamidomethylpyridinyl)-pyrazmone.

5. The salt of claim 4 which is 3-(2-Phenethylamino)-6-methyl-1-(2-amino-6-methyl-5-methylcarboxamidomethylpyridinyl)-pyrazinone dihydrochloride.

6. The salt of claim 5 characterized by a differential scanning calorimetry curve, at a heating rate of 5° C./min in an open cup under flowing nitrogen bubbled through water at 5° C., exhibiting an endotherm with an extrapolated onset temperature of about 102° C., a peak temperature of about 112° C. and an associated heat of about 115 J/gm followed by an endotherm with an extrapolated onset temperature of about 171° C., a peak temperature of about 194° C. and an associated heat of about 83 J/gm; and an x-ray powder diffraction pattern characterized by spectral d-spacings of 13.06, 12.16, 7.40, 5.71, 4.92, 4.48, 4.40, 3.63, 3.07, 2.98, 2.86 and 2.62 Å.

7. The salt of claim 5 characterized by a differential scanning calorimetry curve, at a heating rate of 5° C./min in an open cup under flowing nitrogen bubbled through water at 5° C., exhibiting an endotherm with an extrapolated onset temperature of about 120° C., a peak temperature of about 132° C., and an associated heat of about 123 J/gm followed by an endotherm with an extrapolated onset temperature of about 160° C., a peak temperature of about 191° C. and an associated heat of about 78 J/gm; and an x-ray powder diffraction pattern characterized by spectral d-spacings of 12.98, 11.91, 7.24, 5.98, 4.90, 4.46, 4.23, 3.99, 3.75, 3.61, 3.41, 2.94, 2.85 and 2.61 Å.

8. A composition for inhibiting thrombus formation in blood comprising a compound of claim 1 and a pharmaceutically acceptable carrier.

9. A method for inhibiting thrombin in blood comprising adding to the blood an effective amount of a composition of claim 8.

10. A method for inhibiting thrombus formation in blood comprising adding to the blood an effective amount of a composition of claim 8.

11. A method for treating or preventing venous thromboembolism and pulmonary embolism in a mammal comprising administering to the mammal an effective amount of a composition of claim 8.

12. A method for treating or preventing deep vein thrombosis in a mammal an effective amount of comprising administering to the mammal a composition of claim 8.

13. A method for lowering the propensity of a device which contacts blood to clot blood which comprises coating the device with an effective amount of a composition of claim 8.

14. A process for producing 3-(2-Phenethylamino)-6-methyl-1-(2-amino-6-methyl-5-methylcarboxamidomethylpyridinyl)-pyrazinone dihydrochloride Type A monohydrate comprising the steps of:
 a) dissolving 3-(2-Phenethylamino)-6-methyl-1-(2-amino-6-methyl-5-methylcarboxamidomethylpyridinyl)-pyrazinone in acetic acid solvent and adding aqueous HCl;
 b) recovering the resultant solid phase; and
 c) removing the solvent therefrom.

15. A process of claim 14 wherein the amount of aqueous HCl is such that the final water content in the acetic acid is between 1 and 5 weight %.

16. A process for producing 3-(2-Phenethylamino)-6-methyl-1-(2-amino-6-methyl-5-methylcarboxamidomethylpyridinyl)-pyrazinone dihydrochloride Type B monohydrate comprising the steps of:
 a) dissolving 3-(2-Phenethylamino)-6-methyl-1-(2-amino-6-methyl-5-methylcarboxamidomethylpyridinyl)-pyrazinone in aqueous hydrochloric acid solvent;
 b) recovering the resultant solid phase; and
 c) removing the solvent therefrom.

17. A product prepared according to the process in steps of claim 14 comprising the steps of:
   a) dissolving 3-(2-Phenethylamino)-6-methyl-1-(2-amino-6-methyl-5-methylcarboxamidomethylpyridinyl)-pyrazinone in acetic acid solvent and adding aqueous HCl;
   b) recovering the resultant solid phase; and
   c) removing the solvent therefrom.

18. A product prepared according to the process in steps of claim 16 comprising the steps of:
   a) dissolving 3-(2-Phenethylamino)-6-methyl-1-(2-amino-6-methyl-5-methylcarboxamidomethylpyridinyl)-pyrazinone in hydrochloric acid solvent;
   b) recovering the resultant solid phase; and
   c) removing the solvent therefrom.

* * * * *